US010058603B2

(12) United States Patent
Baudoux et al.

(10) Patent No.: US 10,058,603 B2
(45) Date of Patent: Aug. 28, 2018

(54) VACCINE

(71) Applicant: GLAXOSMITHKLINE BIOLOGICALS S.A., Rixensart (BE)

(72) Inventors: Guy Baudoux, Rixensart (BE); Mathieu Boxus, Rixensart (BE); Brigitte Colau, Rixensart (BE); Martine Marchand, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 14/774,729

(22) PCT Filed: Mar. 13, 2014

(86) PCT No.: PCT/EP2014/054947
§ 371 (c)(1),
(2) Date: Sep. 11, 2015

(87) PCT Pub. No.: WO2014/140166
PCT Pub. Date: Sep. 18, 2014

(65) Prior Publication Data

US 2016/0022803 A1 Jan. 28, 2016

Related U.S. Application Data

(60) Provisional application No. 61/786,765, filed on Mar. 15, 2013.

(51) Int. Cl.
*A61K 39/125* (2006.01)
*A61K 39/12* (2006.01)
(Continued)

(52) U.S. Cl.
CPC ............ *A61K 39/125* (2013.01); *A61K 39/12* (2013.01); *A61K 39/39* (2013.01); *C07K 7/08* (2013.01);
(Continued)

(58) Field of Classification Search
None
See application file for complete search history.

(56) References Cited

U.S. PATENT DOCUMENTS 8,153,760 B2 * 4/2012 Smith .................. C07K 14/005 424/211.1
8,709,779 B2 * 4/2014 Gonzalez ............. C07K 14/005 435/235.1
(Continued)

FOREIGN PATENT DOCUMENTS

EP 0358485 A2 3/1990
WO 92/03475 A1 3/1992
(Continued)

OTHER PUBLICATIONS

Norder et al., "Picornavirus non-structural proteins as targets for new anti-virals with broad activity," Antiviral Research 89: 204-218 (2011).*
Tapparel et al., "Picornavirus and enterovirus diversity with associated human diseases," Infection Genetics and Evolution 14: 282-293 (2013).*
McCray and Werner, Different rhinovirus serotypes neutralized by antipeptide antibodies, (1987) Nature 329 (6141): 736-738.
Delpeyroux, et al., Structural Factors Modulate the Activity of Antigenic Poliovirus Sequences Expressed on Hybrid Hepatitis B Surface Antigen Particles, (1990) Journal of Virology 64(12): 6090-6100.
(Continued)

*Primary Examiner* — Janet L Andres
*Assistant Examiner* — M Franco G Salvoza
(74) *Attorney, Agent, or Firm* — Virgina G. Campen

(57) ABSTRACT

The disclosure provides immunogenic compositions comprising human picornavirus peptides derived from structural proteins of the virus, constructs comprising the peptides, the peptides themselves and their use in the prevention of picornavirus infection and disease. Particular peptides from VP4 and VP1 are disclosed.

8 Claims, 28 Drawing Sheets

Specification includes a Sequence Listing.

| **Proteins** | **Functions** |
|---|---|
| VPg | Small virus protein. |
| VP1-VP4 | Capsid proteins. |
| 2A | Protease, host protein shutoff, stimulation of the initiation of negative-strand RNA synthesis. |
| 2B | Membrane permeability, involved at the beginning of viral RNA synthesis, inhibition of protein secretion from the Golgi system. |
| 2C | Vesicle formation, directing replication complexes to cell membranes, causing disassembly of the Golgi system, and endoplasmic reticulum, NTPase. |
| 2BC | RNA binding, vesicle formation, membrane permeability (2B-2C fusion). |
| 3A | Inhibition of intracellular transport. |
| 3B | VPg, protein primer for viral RNA synthesis. |
| 3AB | Anchors VPg in membranes for the priming step of RNA synthesis, interaction of the 3D and 3CD membrane association of replication complexes(3A-3B fusion). |
| 3C | Protease, inhibits host transcription. |
| 3D | RNA-dependent RNA polymerase, VPg uridylation. |
| 3CD | Viral protein processing (3C-3D fusion). |

(51) Int. Cl.

| | |
|---|---|
| ***A61K 39/00*** | (2006.01) |
| ***C12N 7/00*** | (2006.01) |
| ***C07K 14/085*** | (2006.01) |
| ***A61K 39/39*** | (2006.01) |
| ***C07K 7/08*** | (2006.01) |
| ***C07K 14/005*** | (2006.01) |

(52) U.S. Cl.
CPC .......... *C07K 14/005* (2013.01); *C07K 14/085* (2013.01); *C12N 7/00* (2013.01); *A61K 2039/55566* (2013.01); *A61K 2039/6075* (2013.01); *A61K 2039/6081* (2013.01); *A61K 2039/64* (2013.01); *C12N 2770/32034* (2013.01); *C12N 2770/32334* (2013.01); *C12N 2770/32722* (2013.01); *C12N 2770/32734* (2013.01)

(56) References Cited

U.S. PATENT DOCUMENTS

2011/0236468 A1* 9/2011 Lorin .................. A61K 39/015
424/450
2014/0134199 A1* 5/2014 Li ......................... C07K 14/34
424/185.1

FOREIGN PATENT DOCUMENTS

| | | | | |
|---|---|---|---|---|
| WO | 2006/029887 | A2 | 3/2006 | |
| WO | 2006/078648 | A2 | 7/2006 | |
| WO | 2008/057158 | A2 | 5/2008 | |
| WO | WO 2011050384 | A2 * | 5/2011 | ............. A61K 39/12 |
| WO | 2012/138774 | A2 | 10/2012 | |
| WO | WO 2013019603 | A2 * | 2/2013 | ........... A61K 39/145 |

OTHER PUBLICATIONS

Pumpens and Grens, HBV Core Particles as a Carrier for B Cell/T Cell Epitopes, (2001) Intervirology 44(2-3): 98-114.

Pumpens, et al., Evaluation of HBs, HBc, and frCP Virus-Like Particles for Expression of Human Papillomavirus 16 E7 Oncoprotein Epitopes, (2002) Intervirology 45(1): 24-32.

Vietheer, et al., Immunizations with chimeric hepatitis B virus-like particles to induce potential anti-hepatitis C virus neutralizing antibodies, (2007) Antiviral Therapy 12(4): 477-487.

Zhang, et al., Enhanced Immunogenicity of Modified Hepatitis B Virus Core Particle Fused with Multiepitopes of Foot-and-Mouth Disease Virus, (2007) Scandinavian Journal of Immunology 65(4): 320-328.

Katpally, et al., Antibodies to the Buried N Terminus of Rhinovirus VP4 Exhibit Cross-Serotypic Neutralization, (2009) Journal of Virology 83(14): 7040-7048.

Miao, et al., Monoclonal Antibodies to VP1 Recognize a Broad Range of Enteroviruses, (2009) Journal of Clinical Microbiology 47(10): 3108-3113.

Liu, et al., Combined peptides of human enterovirus 71 protect against virus infection in mice, (2010) Vaccine 28(46): 7444-7451.

Eldmayr, et al., Antibodies induced with recombinant VP1 from human rhinovirus exhibit cross-neutralisation, (2011) European Respiratory Journal 37(1): 44-52.

Kotiw, et al., Immunological Response to Parental Vaccination with Recombinant Hepatitis B Virus Surface Antigen Virus-Like Particles Expressing Helicobacter pylori KatA Epitopes in a Murine H. pylori Challenge Model, (2012) Clinical and Vaccine Immunology 19(2): 268-276.

Roose, et al., Hepatitis B core-based virus-like particles to present heterologous epitopes, (2013) Expert Review of Vaccines 12(2): 183-198.

* cited by examiner

Figure 1

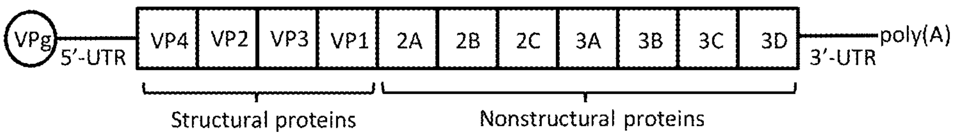

| **Proteins** | **Functions** |
|---|---|
| VPg | Small virus protein. |
| VP1-VP4 | Capsid proteins. |
| 2A | Protease, host protein shutoff, stimulation of the initiation of negative-strand RNA synthesis. |
| 2B | Membrane permeability, involved at the beginning of viral RNA synthesis, inhibition of protein secretion from the Golgi system. |
| 2C | Vesicle formation, directing replication complexes to cell membranes, causing disassembly of the Golgi system, and endoplasmic reticulum, NTPase. |
| 2BC | RNA binding, vesicle formation, membrane permeability (2B-2C fusion). |
| 3A | Inhibition of intracellular transport. |
| 3B | VPg, protein primer for viral RNA synthesis. |
| 3AB | Anchors VPg in membranes for the priming step of RNA synthesis, interaction of the 3D and 3CD membrane association of replication complexes(3A-3B fusion). |
| 3C | Protease, inhibits host transcription. |
| 3D | RNA-dependent RNA polymerase, VPg uridylation. |
| 3CD | Viral protein processing (3C-3D fusion). |

Figure 5
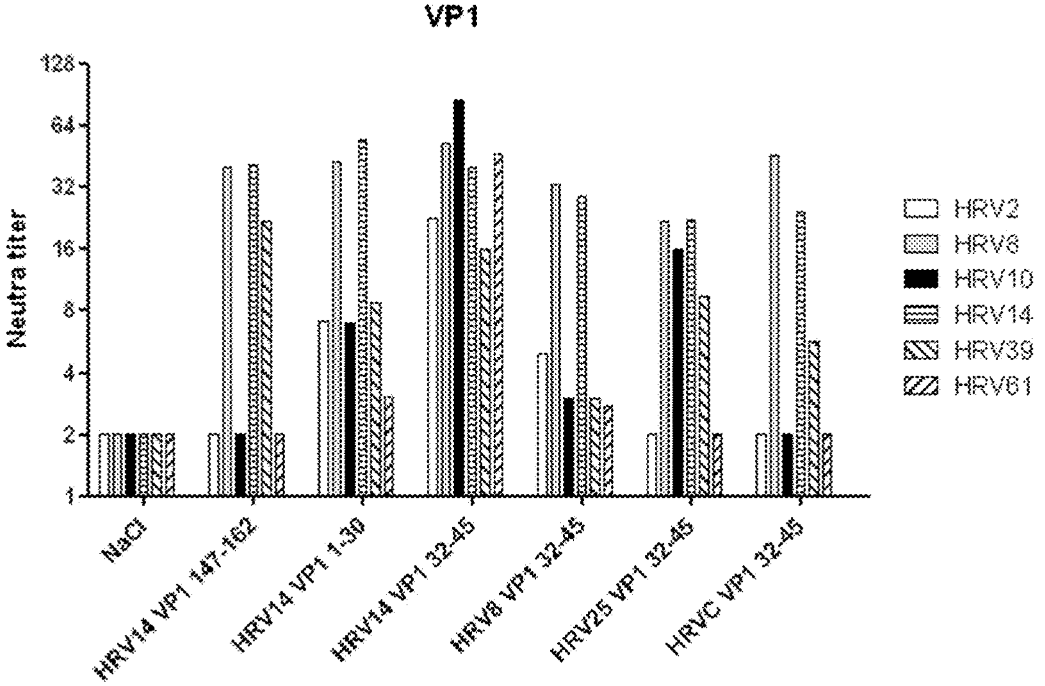
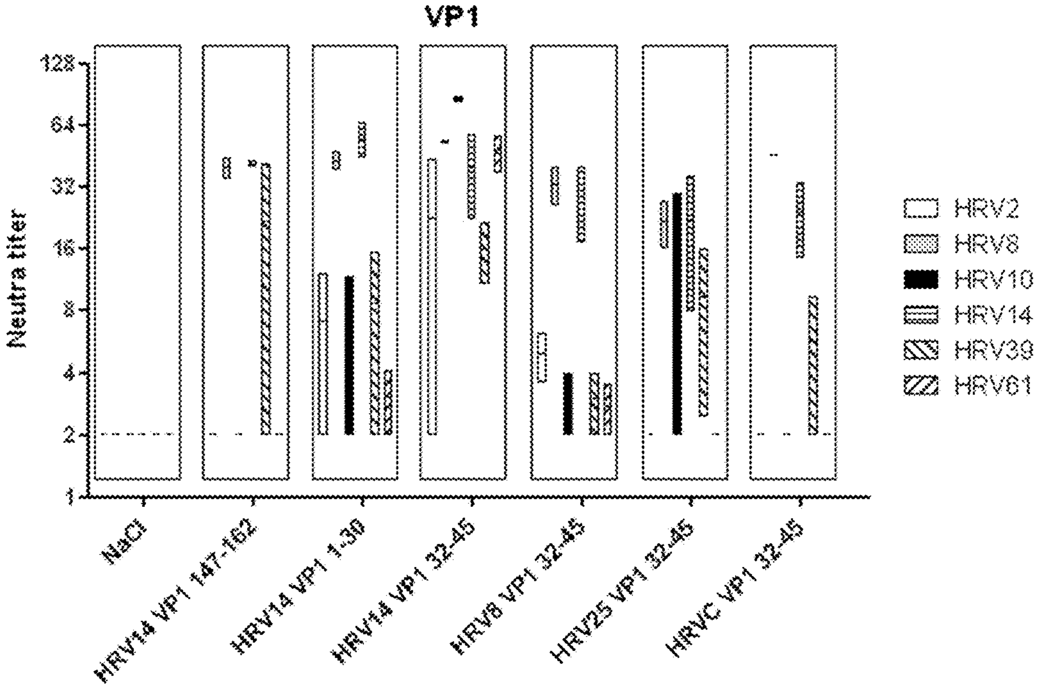
In the 2 versions of Figure 5 above, the first shows classical bars (= mean) and the second shows floating bars (min and max = titers of the 2 animals + mean)

Figure 6
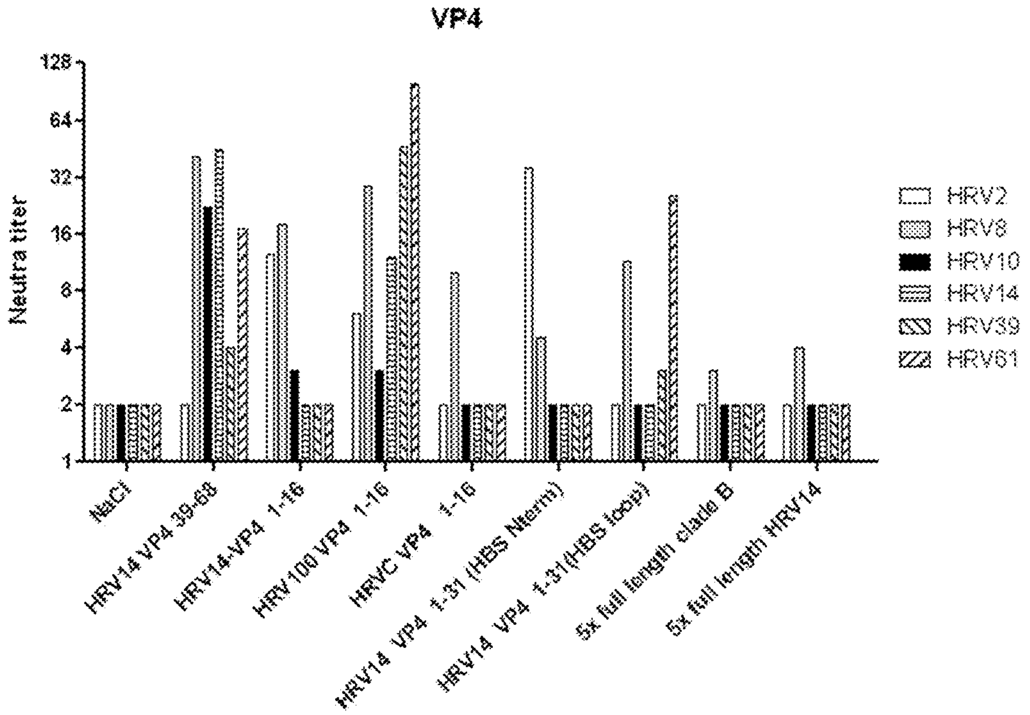
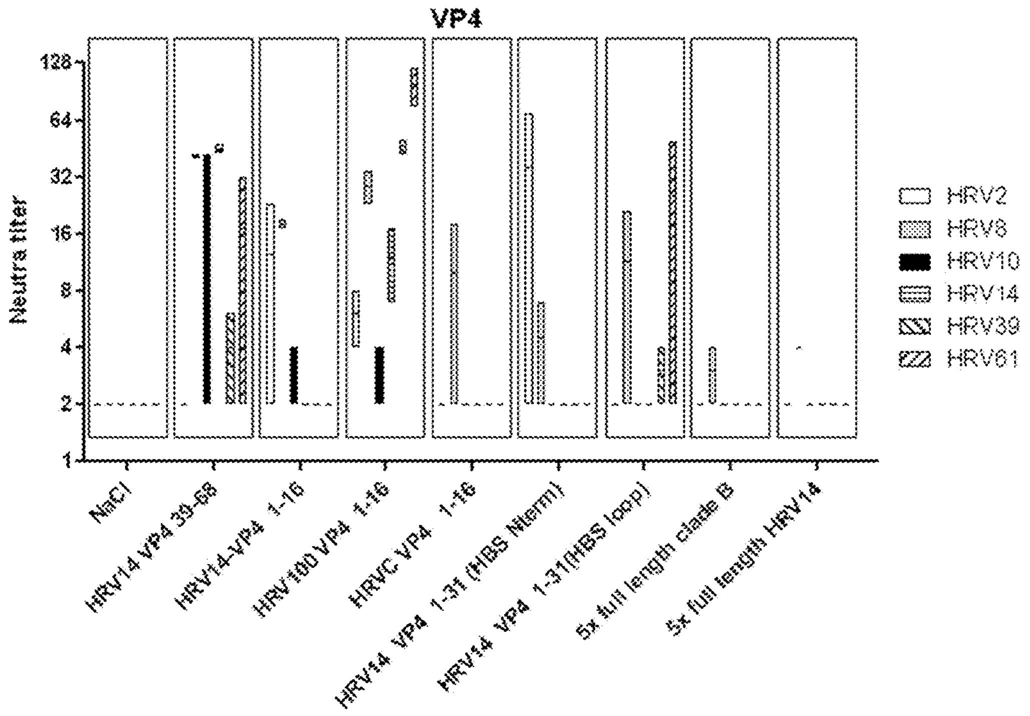
In the 2 versions of Figure 6 above, the first shows classical bars (= mean) and the second shows floating bars (min and max = titers of the 2 animals + mean)

FIG. 8A

| | | | | | | |
|---|---|---|---|---|---|---|
| hrv1_A_B9V432 | : | PLLDAAETGHTSNV | : | 14 | (SEQ ID NO:16) |
| hrv1b_A_P12916 | : | PLLDAAETGHTSNV | : | 14 | (SEQ ID NO:16) |
| hrv2_A_P04936 | : | PALDAAETGHTSSV | : | 14 | (SEQ ID NO: 2) |
| hrv7_A_A5GZF2 | : | PALDAAETGHTSSV | : | 14 | (SEQ ID NO: 2) |
| hrv8_A_B9V434 | : | PALDAAETGHTSSV | : | 14 | (SEQ ID NO: 2) |
| hrv9_A_B9V435 | : | PALDAAETGHTSNV | : | 14 | (SEQ ID NO:17) |
| hrv10_A_A5GZE7 | : | PILDAAETGHTSSV | : | 14 | (SEQ ID NO:18) |
| hrv11_A_A7KC06 | : | PALDAAETGHTSKV | : | 14 | (SEQ ID NO:19) |
| hrv12_A_A7KC07 | : | PALDAAETGHTSQT | : | 14 | (SEQ ID NO:20) |
| hrv13_A_B9V437 | : | PALDAAETGHTSSV | : | 14 | (SEQ ID NO: 2) |
| hrv15_A_A5GZE2 | : | PALDAAETGHTSSV | : | 14 | (SEQ ID NO: 2) |
| hrv16_A_Q82122 | : | PVLDAAETGHTNKI | : | 14 | (SEQ ID NO:11) |
| hrv18_A_B9V439 | : | PALDAAETGHTSNV | : | 14 | (SEQ ID NO:17) |
| hrv19_A_B9V440 | : | PALDAAETGHTSNV | : | 14 | (SEQ ID NO:17) |
| hrv20_A_B9V441 | : | PALDAAETGHTNQV | : | 14 | (SEQ ID NO:22) |
| hrv21_A_B9V442 | : | PALDAAETGHTSNV | : | 14 | (SEQ ID NO:17) |
| hrv22_A_B9V443 | : | PALDAAETGHTSNV | : | 14 | (SEQ ID NO:17) |
| hrv23_A_A5GZE6 | : | PALDAAETGHTSNV | : | 14 | (SEQ ID NO:17) |
| hrv24_A_A7KC08 | : | PALDAAETGHTSSV | : | 14 | (SEQ ID NO: 2) |
| hrv25_A_B9V444 | : | PILDAAETGHTSNV | : | 14 | (SEQ ID NO: 3) |
| hrv28_A_A5GZF7 | : | PALDAAETGHTSQT | : | 14 | (SEQ ID NO:20) |
| hrv29_A_B9V446 | : | PILDAAETGHTSNV | : | 14 | (SEQ ID NO: 3) |
| hrv30_A_A5GZG1 | : | PALDAAETGHTSNV | : | 14 | (SEQ ID NO:17) |
| hrv31_A_B9V447 | : | PILDAAETGHTSNV | : | 14 | (SEQ ID NO: 3) |
| hrv32_A_B9V448 | : | PALDAAETGHTSNV | : | 14 | (SEQ ID NO:17) |
| hrv33_A_B9V449 | : | PALDAAETGHTNNV | : | 14 | (SEQ ID NO:23) |
| hrv34_A_A5GZF0 | : | PALDAAETGHTSSV | : | 14 | (SEQ ID NO: 2) |
| hrv36_A_A5GZF4 | : | PALDAAETGHTSSV | : | 14 | (SEQ ID NO: 2) |
| hrv38_A_A5GZE4 | : | PALDAAETGHTSNV | : | 14 | (SEQ ID NO:17) |
| hrv39_A_Q5XLP5 | : | TALDAAETGHTSSI | : | 14 | (SEQ ID NO:24) |
| hrv40_A_B9V450 | : | PALDAAETGHTSNI | : | 14 | (SEQ ID NO:25) |
| hrv41_A_A5GZE0 | : | PALDAAETGHTSNV | : | 14 | (SEQ ID NO:17) |
| hrv43_A_B9V452 | : | PALDAAETGHTSQV | : | 14 | (SEQ ID NO:26) |
| hrv44_A_A5GZE8 | : | PILDAAETGHTSNV | : | 14 | (SEQ ID NO: 3) |
| hrv45_A_B9V453 | : | PALDAAETGHTSSV | : | 14 | (SEQ ID NO: 2) |
| hrv46_A_A5GZF5 | : | PALDAAETGHTSQI | : | 14 | (SEQ ID NO:27) |
| hrv47_A_B9V454 | : | PILDAAETGHTSNV | : | 14 | (SEQ ID NO: 3) |
| hrv49_A_A5GZE5 | : | PALDAAETGHTSNV | : | 14 | (SEQ ID NO:17) |
| hrv50_A_B9V456 | : | PALDAAETGHTSNV | : | 14 | (SEQ ID NO:17) |
| hrv51_A_B9V457 | : | PALDAAETGHTSQV | : | 14 | (SEQ ID NO:26) |

FIG. 8B

| | | | | | | |
|---|---|---|---|---|---|---|
| hrv53_A_A5GZF6 | : | PALDAAETGHTSQT | : | 14 | (SEQ ID NO:20) |
| hrv54_A_B9V459 | : | PALDAAETGHTSGI | : | 14 | (SEQ ID NO:28) |
| hrv55_A_A5GZG0 | : | PVLDAAETGHTSNV | : | 14 | (SEQ ID NO:29) |
| hrv56_A_B9V461 | : | PALDAAETGHTSAI | : | 14 | (SEQ ID NO:30) |
| hrv57_A_B9V462 | : | PALDAAETGHTSNV | : | 14 | (SEQ ID NO:17) |
| hrv58_A_B9V463 | : | PALDAAETGHTSSV | : | 14 | (SEQ ID NO: 2) |
| hrv59_A_A5GZE9 | : | PALDAAETGHTSSI | : | 14 | (SEQ ID NO:31) |
| hrv60_A_B9V464 | : | PALDAAETGHTSNV | : | 14 | (SEQ ID NO:17) |
| hrv61_A_B9V465 | : | PVLDAAETGHTSNV | : | 14 | (SEQ ID NO:29) |
| hrv62_A_B9V466 | : | PILDAAETGHTSNV | : | 14 | (SEQ ID NO: 3) |
| hrv63_A_B9V467 | : | PVLDAAETGHTSSI | : | 14 | (SEQ ID NO:32) |
| hrv64_A_A7KC09 | : | PALDAAETGHTSNV | : | 14 | (SEQ ID NO:17) |
| hrv65_A_B9V468 | : | PALDAAETGHTSQV | : | 14 | (SEQ ID NO:26) |
| hrv66_A_B9V469 | : | PILDAAETGHTSKV | : | 14 | (SEQ ID NO:33) |
| hrv67_A_B9V470 | : | PALDAAETGHTSSV | : | 14 | (SEQ ID NO: 2) |
| hrv68_A_B9V471 | : | PALDAAETGHTNQV | : | 14 | (SEQ ID NO:22) |
| hrv71_A_B9V473 | : | PALDAAETGHTNQV | : | 14 | (SEQ ID NO:22) |
| hrv73_A_A5GZE1 | : | PALDAAETGHTSGV | : | 14 | (SEQ ID NO:34) |
| hrv74_A_A5GZE3 | : | PALDAAETGHTSNV | : | 14 | (SEQ ID NO:17) |
| hrv75_A_A5GZF9 | : | PALDAAETGHTSHV | : | 14 | (SEQ ID NO:35) |
| hrv76_A_A5GZF1 | : | PALDAAETGHTSSV | : | 14 | (SEQ ID NO: 2) |
| hrv77_A_B9V475 | : | PILDAAETGHTSSV | : | 14 | (SEQ ID NO:18) |
| hrv78_A_A7KC10 | : | PVLDAAETGHTNQV | : | 14 | (SEQ ID NO:36) |
| hrv80_A_B9V477 | : | PTLDAAETGHTSQV | : | 14 | (SEQ ID NO:37) |
| hrv81_A_B9V478 | : | PVLDAAETGHTSNI | : | 14 | (SEQ ID NO:38) |
| hrv82_A_B9V481 | : | PALDAAETGHTSTV | : | 14 | (SEQ ID NO:39) |
| hrv85_A_B9V484 | : | PALDAAETGHTSSI | : | 14 | (SEQ ID NO:31) |
| hrv88_A_A5GZF3 | : | PALDAAETGHTSSV | : | 14 | (SEQ ID NO: 2) |
| hrv89_A_B9V486 | : | PALDAAETGHTSSV | : | 14 | (SEQ ID NO: 2) |
| hrv90_A_B9V488 | : | PALDAAETGHTSDV | : | 14 | (SEQ ID NO:40) |
| hrv94_A_A7KC11 | : | PALDAAETGHTSNV | : | 14 | (SEQ ID NO:17) |
| hrv95_A_B9V491 | : | PALDAAETGHTSSV | : | 14 | (SEQ ID NO: 2) |
| hrv96_A_B9V492 | : | PVLDAAETGHTSNV | : | 14 | (SEQ ID NO:29) |
| hrv98_A_B9V494 | : | PTLDAAETGHTSGI | : | 14 | (SEQ ID NO:41) |
| hrv100_A_B9V496 | : | PILDAAETGHTSNV | : | 14 | (SEQ ID NO: 3) |
| hrv_A_A101 | : | PVLDAAETGHTSQT | : | 14 | (SEQ ID NO:42) |
| hrv_A_AMS323 | : | PALDAAETGHTNQV | : | 14 | (SEQ ID NO:22) |
| hrv_A_CU107 | : | PALDAAETGHTSQT | : | 14 | (SEQ ID NO:20) |
| hrv_A_CU150 | : | PVLDAAETGHTSNI | : | 14 | (SEQ ID NO:38) |
| hrv_A_N13 | : | PILDAAETGHTSNV | : | 14 | (SEQ ID NO: 3) |
| hrvA_A_A101v1 | : | PALDAAETGHTNQT | : | 14 | (SEQ ID NO:43) |
| hrvA_A_A5GZF8 | : | PALDAAETGHTSTV | : | 14 | (SEQ ID NO:39) |

FIG. 9

| | | | | | | |
|---|---|---|---|---|---|---|
| | | | | | | * |
| hrv3_B_A5GZD4 | : | PALTANETGATLPT | : | 14 | (SEQ ID NO:44) | |
| hrv4_B_A5GZD9 | : | PALTANETGATLPT | : | 14 | (SEQ ID NO:44) | |
| hrv5_B_B9V433 | : | PSLTANETGATLPT | : | 14 | (SEQ ID NO:45) | |
| hrv6_B_A5GZD5 | : | PILTANETGATMPT | : | 14 | (SEQ ID NO:46) | |
| hrv14_B_P03303 | : | PILTANETGATMPV | : | 14 | (SEQ ID NO: 1) | |
| hrv17_B_A7KC12 | : | PALSANETGATLPT | : | 14 | (SEQ ID NO:47) | |
| hrv26_B_B9V445 | : | PALTANETGATMPT | : | 14 | (SEQ ID NO:48) | |
| hrv27_B_A7KC13 | : | PTLSASETGTTLPT | : | 14 | (SEQ ID NO:49) | |
| hrv35_B_A5GZD6 | : | PMLTANETGASMPV | : | 14 | (SEQ ID NO:50) | |
| hrv35_B_B9V4A8 | : | PTLTANETGASMPV | : | 14 | (SEQ ID NO:51) | |
| hrv37_B_A7KC15 | : | PTLTANETGATMPT | : | 14 | (SEQ ID NO:52) | |
| hrv42_B_B9V451 | : | PSLTANETGATLPT | : | 14 | (SEQ ID NO:45) | |
| hrv48_B_A5GZD7 | : | PALSANETGATLPT | : | 14 | (SEQ ID NO:47) | |
| hrv52_B_A7KC16 | : | PALSASETGATLPT | : | 14 | (SEQ ID NO:53) | |
| hrv69_B_B9V472 | : | PALSASETGATLPT | : | 14 | (SEQ ID NO:53) | |
| hrv70_B_A5GZD8 | : | PALSANETGATLPT | : | 14 | (SEQ ID NO:47) | |
| hrv72_B_B9V474 | : | PTLTANETGATMPT | : | 14 | (SEQ ID NO:52) | |
| hrv79_B_B9V476 | : | PTLTANETGATMPT | : | 14 | (SEQ ID NO:52) | |
| hrv83_B_B9V482 | : | PILTANETGATMPT | : | 14 | (SEQ ID NO:46) | |
| hrv84_B_B9V483 | : | PTLSASETGATLQT | : | 14 | (SEQ ID NO:54) | |
| hrv86_B_B9V485 | : | PSLSANETGATMPT | : | 14 | (SEQ ID NO:55) | |
| hrv91_B_B9V489 | : | PALSANETGATLPT | : | 14 | (SEQ ID NO:47) | |
| hrv92_B_B9V490 | : | PTLTANETGATMPT | : | 14 | (SEQ ID NO:52) | |
| hrv93_B_A7KC17 | : | PTLSASETGATLPT | : | 14 | (SEQ ID NO:56) | |
| hrv97_B_B9V493 | : | PTLSASETGATLPT | : | 14 | (SEQ ID NO:56) | |
| hrv99_B_B9V495 | : | PALTANETGATLPT | : | 14 | (SEQ ID NO:44) | |
| hrv_B_CU003 | : | PALSASETGATLPT | : | 14 | (SEQ ID NO:53) | |
| hrv_B_CU211 | : | PTLTANETGASMPV | : | 14 | (SEQ ID NO:51) | |

FIG. 10

```
                                    *
hrv_C_C15       : SILGAMEIGASSNA : 14  (SEQ ID NO:57)
hrv_C_024       : SALGAMEIGASSTT : 14  (SEQ ID NO:58)
hrv_C_025       : TALSAMEIGASSDV : 14  (SEQ ID NO:59)
hrv_C_026       : QALGAVEIGATADV : 14  (SEQ ID NO: 4)
hrv_C_CL170085  : TALSAMEIGASSDV : 14  (SEQ ID NO:59)
hrv_C_CU072     : TALGAMEIGASSDA : 14  (SEQ ID NO:60)
hrv_C_CU184     : QTLGALEIGATAEI : 14  (SEQ ID NO:61)
hrv_C_N10       : SALNAMEVGVTPDV : 14  (SEQ ID NO:62)
hrv_C_N4        : SALGAMEIGASSSV : 14  (SEQ ID NO:63)
hrv_C_NAT001    : QTLGALEIGATAEI : 14  (SEQ ID NO:61)
hrv_C_NAT045    : TVLNAMEIGVTPDA : 14  (SEQ ID NO:64)
hrv_C_NY074     : QALGALEIGATADV : 14  (SEQ ID NO:65)
hrv_C_QCE       : QALGALEIGATADL : 14  (SEQ ID NO:66)
hrv_C_QPM       : QALGAVEIGATADV : 14  (SEQ ID NO: 4)
```

FIG. 11A

```
hrv1_A_B9V432    : GAQVSRQNVGTHSTQN : 16  (SEQ ID NO:6)
hrv1b_A_P12916   : GAQVSRQNVGTHSTQN : 16  (SEQ ID NO:6)
hrv2_A_P04936    : GAQVSRQNVGTHSTQN : 16  (SEQ ID NO:6)
hrv7_A_A5GZF2    : GAQVSRQNVGTHSTQN : 16  (SEQ ID NO:6)
hrv8_A_B9V434    : GAQVSRQNVGTHSTQN : 16  (SEQ ID NO:6)
hrv9_A_B9V435    : GAQVSRQNVGTHSTQN : 16  (SEQ ID NO:6)
hrv10_A_A5GZE7   : GAQVSRQNVGTHSTQN : 16  (SEQ ID NO:6)
hrv11_A_A7KC06   : GAQVSRQNVGTHSTQN : 16  (SEQ ID NO:6)
hrv12_A_A7KC07   : GAQVSRQNVGTHSTQN : 16  (SEQ ID NO:6)
hrv13_A_B9V437   : GAQVSRQNVGTHSTQN : 16  (SEQ ID NO:6)
hrv15_A_A5GZE2   : GAQVSRQNVGTHSTQN : 16  (SEQ ID NO:6)
hrv16_A_Q82122   : GAQVSRQNVGTHSTQN : 16  (SEQ ID NO:6)
hrv18_A_B9V439   : GAQVSRQNVGTHSTQN : 16  (SEQ ID NO:6)
hrv19_A_B9V440   : GAQVSRQNVGTHSTQN : 16  (SEQ ID NO:6)
hrv20_A_B9V441   : GAQVSRQNVGTHSTQN : 16  (SEQ ID NO:6)
hrv21_A_B9V442   : GTQVSRQNVGTHSTQN : 16  (SEQ ID NO:177)
hrv22_A_B9V443   : GAQVSRQNVGTHSTQN : 16  (SEQ ID NO:6)
hrv23_A_A5GZE6   : GAQVSRQNVGTHSTQN : 16  (SEQ ID NO:6)
hrv24_A_A7KC08   : GAQVSRQNVGTHSTQN : 16  (SEQ ID NO:6)
hrv25_A_B9V444   : GAQVSRQNVGTHSTQN : 16  (SEQ ID NO:6)
hrv28_A_A5GZF7   : GAQVSRQNVGTHTTQN : 16  (SEQ ID NO:178)
hrv29_A_B9V446   : GAQVSRQNVGTHSTQN : 16  (SEQ ID NO:6)
hrv30_A_A5GZG1   : GAQVSRQNVGTHSTQN : 16  (SEQ ID NO:6)
hrv31_A_B9V447   : GAQVSRQNVGTHSTQN : 16  (SEQ ID NO:6)
hrv32_A_B9V448   : GAQVSRQNVGTHSTQN : 16  (SEQ ID NO:6)
hrv33_A_B9V449   : GAQVSRQNVGTHSTQN : 16  (SEQ ID NO:6)
hrv34_A_A5GZF0   : GAQVSRQNVGTHSTQN : 16  (SEQ ID NO:6)
hrv36_A_A5GZF4   : GAQVSRQNVGTHSTQN : 16  (SEQ ID NO:6)
hrv38_A_A5GZE4   : GAQVSRQNVGTHSTQN : 16  (SEQ ID NO:6)
hrv39_A_Q5XLP5   : GAQVSRQNVGTHSTQN : 16  (SEQ ID NO:6)
hrv40_A_B9V450   : GAQVSRQNVGTHSTQN : 16  (SEQ ID NO:6)
hrv41_A_A5GZE0   : GAQVSRQNVGTHSTQN : 16  (SEQ ID NO:6)
hrv43_A_B9V452   : GAQVSRQNVGTHSTQN : 16  (SEQ ID NO:6)
hrv44_A_A5GZE8   : GAQVSRQNVGTHSTQN : 16  (SEQ ID NO:6)
hrv45_A_B9V453   : GAQVSRQNVGTHSTQN : 16  (SEQ ID NO:6)
hrv46_A_A5GZF5   : GAQVSRQNVGTHSTQN : 16  (SEQ ID NO:6)
hrv47_A_B9V454   : GAQVSRQNVGTHSTQN : 16  (SEQ ID NO:6)
hrv49_A_A5GZE5   : GAQVSRQNVGTHSTQN : 16  (SEQ ID NO:6)
hrv50_A_B9V456   : GAQVSRQNVGTHSTQN : 16  (SEQ ID NO:6)
hrv51_A_B9V457   : GAQVSRQNVGTHSTQN : 16  (SEQ ID NO:6)
hrv53_A_A5GZF6   : GAQVSRQNVGTHSTQN : 16  (SEQ ID NO:6)
hrv54_A_B9V459   : GAQVSRQNVGTHSTQN : 16  (SEQ ID NO:6)
hrv55_A_A5GZG0   : GAQVSRQNVGTHSTQN : 16  (SEQ ID NO:6)
hrv56_A_B9V461   : GAQVSRQNVGTHSTQN : 16  (SEQ ID NO:6)
hrv57_A_B9V462   : GAQVSRQNVGTHSTQN : 16  (SEQ ID NO:6)
hrv58_A_B9V463   : GAQVSRQNVGTHSTQN : 16  (SEQ ID NO:6)
hrv59_A_A5GZE9   : GAQVSRQNVGTHSTQN : 16  (SEQ ID NO:6)
```

FIG. 11B

| | | | |
|---|---|---|---|
| hrv60_A_B9V464 | GAQVSRQNVGTHSTQN | 16 | (SEQ ID NO:6) |
| hrv61_A_B9V465 | GAQVSRQNVGTHSTQN | 16 | (SEQ ID NO:6) |
| hrv62_A_B9V466 | GAQVSRQNVGTHSTQN | 16 | (SEQ ID NO:6) |
| hrv63_A_B9V467 | GAQVSRQNVGTHSTQN | 16 | (SEQ ID NO:6) |
| hrv64_A_A7KC09 | GAQVSRQNVGTHSTQN | 16 | (SEQ ID NO:6) |
| hrv65_A_B9V468 | GAQVSRQNVGTHSTQN | 16 | (SEQ ID NO:6) |
| hrv66_A_B9V469 | GAQVSRQNVGTHSTQN | 16 | (SEQ ID NO:6) |
| hrv67_A_B9V470 | GAQVSRQNVGTHSTQN | 16 | (SEQ ID NO:6) |
| hrv68_A_B9V471 | GAQVSRQNVGTHSTQN | 16 | (SEQ ID NO:6) |
| hrv71_A_B9V473 | GAQVSRQNVGTHSTQN | 16 | (SEQ ID NO:6) |
| hrv73_A_A5GZE1 | GAQVSRQNVGTHSTQN | 16 | (SEQ ID NO:6) |
| hrv74_A_A5GZE3 | GAQVSRQNVGTHSTQN | 16 | (SEQ ID NO:6) |
| hrv75_A_A5GZF9 | GAQVSRQNVGTHSTQN | 16 | (SEQ ID NO:6) |
| hrv76_A_A5GZF1 | GAQVSRQNVGTHSTQN | 16 | (SEQ ID NO:6) |
| hrv77_A_B9V475 | GAQVSRQNVGTHSTQN | 16 | (SEQ ID NO:6) |
| hrv78_A_A7KC10 | GAQVSRQNVGTHSTQN | 16 | (SEQ ID NO:6) |
| hrv80_A_B9V477 | GAQVSRQNVGTHSTQN | 16 | (SEQ ID NO:6) |
| hrv81_A_B9V478 | GAQVSRQNVGTHSTQN | 16 | (SEQ ID NO:6) |
| hrv82_A_B9V481 | GAQVSRQNVGTHSTQN | 16 | (SEQ ID NO:6) |
| hrv85_A_B9V484 | GAQVSRQNVGTHSTQN | 16 | (SEQ ID NO:6) |
| hrv88_A_A5GZF3 | GAQVSRQNVGTHSTQN | 16 | (SEQ ID NO:6) |
| hrv89_A_B9V486 | GAQVSRQNVGTHSTQN | 16 | (SEQ ID NO:6) |
| hrv90_A_B9V488 | GAQVSRQNVGTHSTQN | 16 | (SEQ ID NO:6) |
| hrv94_A_A7KC11 | GAQVSRQNVGTHSTQN | 16 | (SEQ ID NO:6) |
| hrv95_A_B9V491 | GAQVSRQNVGTHSTQN | 16 | (SEQ ID NO:6) |
| hrv96_A_B9V492 | GAQVSRQNVGTHSTQN | 16 | (SEQ ID NO:6) |
| hrv98_A_B9V494 | GAQVSRQNVGTHSTQN | 16 | (SEQ ID NO:6) |
| hrv100_A_B9V496 | GAQVSRQNVGTHSTQN | 16 | (SEQ ID NO:6) |
| hrv_A_A101 | GAQVSRQNVGTHSTQN | 16 | (SEQ ID NO:6) |
| hrv_A_AMS323 | GAQVSRQNVGTHSTQN | 16 | (SEQ ID NO:6) |
| hrv_A_CU107 | GAQVSRQNVGTHLTHN | 16 | (SEQ ID NO:67) |
| hrv_A_CU150 | GAQVPRQKVGTHSTQN | 16 | (SEQ ID NO:68) |
| hrv_A_N13 | GAQVSRQNVGTHSTQN | 16 | (SEQ ID NO:6) |
| hrvA_A_A101v1 | GAQVSRQNVGTHSTQN | 16 | (SEQ ID NO:6) |
| hrvA_A_A5GZF8 | GAQVSRQNVGTHSTQN | 16 | (SEQ ID NO:6) |

FIG. 12

```
hrv3_B_A5GZD4   : GAQVSTQKSGSHENQN : 16  (SEQ ID NO:5)
hrv4_B_A5GZD9   : GAQVSTQKSGSHENQN : 16  (SEQ ID NO:5)
hrv5_B_B9V433   : GAQVSTQKSGSHENQN : 16  (SEQ ID NO:5)
hrv6_B_A5GZD5   : GAQVSTQKSGSHENQN : 16  (SEQ ID NO:5)
hrv14_B_P03303  : GAQVSTQKSGSHENQN : 16  (SEQ ID NO:5)
hrv17_B_A7KC12  : GAQVSTQKSGSHENQN : 16  (SEQ ID NO:5)
hrv26_B_B9V445  : GAQVSTQKSGSHENQN : 16  (SEQ ID NO:5)
hrv27_B_A7KC13  : GAQVSTQKSGSHENQN : 16  (SEQ ID NO:5)
hrv35_B_A5GZD6  : GAQVSTQKSGSHENQN : 16  (SEQ ID NO:5)
hrv37_B_A7KC15  : GAQVSTQKSGSHENQN : 16  (SEQ ID NO:5)
hrv42_B_B9V451  : GAQVSTQKSGSHENQN : 16  (SEQ ID NO:5)
hrv48_B_A5GZD7  : GAQVSTQKTGSHENQN : 16  (SEQ ID NO:69)
hrv52_B_A7KC16  : GAQVSTQKSGSHENQN : 16  (SEQ ID NO:5)
hrv69_B_B9V472  : GAQVSTQKSGSHENQN : 16  (SEQ ID NO:5)
hrv70_B_A5GZD8  : GAQVSTQRSGSHENQN : 16  (SEQ ID NO:70)
hrv72_B_B9V474  : GAQVSTQKSGSHENQN : 16  (SEQ ID NO:5)
hrv79_B_B9V476  : GAQVSTQKSGSHENQN : 16  (SEQ ID NO:5)
hrv83_B_B9V482  : GAQVSTQKSGSHENQN : 16  (SEQ ID NO:5)
hrv84_B_B9V483  : GAQVSTQKSGSHENQN : 16  (SEQ ID NO:5)
hrv86_B_B9V485  : GAQVSTQRSGSHENQN : 16  (SEQ ID NO:70)
hrv91_B_B9V489  : GAQVSTQKSGSHENQN : 16  (SEQ ID NO:5)
hrv92_B_B9V490  : GAQVSTQKSGSHENQN : 16  (SEQ ID NO:5)
hrv93_B_A7KC1   : GAQISTQKSGSHENQN : 16  (SEQ ID NO:71)
hrv97_B_B9V493  : GAQVSTQKSGSHENQN : 16  (SEQ ID NO:5)
hrv99_B_B9V495  : GAQVSTQKSGSHENQN : 16  (SEQ ID NO:5)
hrv_B_CU003     : GAQVSTQKSGSHENQN : 16  (SEQ ID NO:5)
hrv_B_CU211     : GAQVSTQKSGSHENQN : 16  (SEQ ID NO:5)
```

FIG. 13

```
hrv_C_C15       : GAQVSRQNNGTHENGV : 16  (SEQ ID NO:72)
hrv_C_024       : GAQVSKQNVGSHENSV : 16  (SEQ ID NO:73)
hrv_C_025       : GAQVSKQNVGSHESGI : 16  (SEQ ID NO:74)
hrv_C_026       : GAQVSRQSVGSHETMI : 16  (SEQ ID NO:7)
hrv_C_CL170085  : GAQVSKQNVGSHESGI : 16  (SEQ ID NO:74)
hrv_C_CU072     : GAQVSKQNVGSHENTV : 16  (SEQ ID NO:75)
hrv_C_CU184     : GAQVSRQSVGSHETMI : 16  (SEQ ID NO:7)
hrv_C_N10       : GAQVSRQKVGSHDNAI : 16  (SEQ ID NO:76)
hrv_C_N4        : GAQVSKQNTGSHESAI : 16  (SEQ ID NO:77)
hrv_C_NAT001    : GAQVSRQSVGSHETMI : 16  (SEQ ID NO:7)
hrv_C_NAT045    : GAQVSKQNVGSHENSV : 16  (SEQ ID NO:73)
hrv_C_NY074     : GAQVSKQSVGAHETMV : 16  (SEQ ID NO:78)
hrv_C_QCE       : GAQVSRQSVGSHETMI : 16  (SEQ ID NO:7)
hrv_C_QPM       : GAQVSRQSVGSHETMI : 16  (SEQ ID NO:7)
```

FIG. 14A

```
                        *        20         *        40         *        60         *        80         *       100         *       120
HRV14_B    :G----------LGDELEEVIVEKTK--------------QTVASISSGP-KHTQKVPILTANETGATMPVLPSDSIETRTTYMHFNGSETDVECFLGRAACVHVTEIQNKDATGID---- 91
(SEQ ID NO:79)

HRV100_A   :N-------------PVENYVEGVLN-----------EVLVVPNIRESHP-STSNSAPILDAAETGHTSNVQPEDTVETRYVQTSQTRDEMSIESFLGRSGCIHTSTITV-SKMKN----- 89
(SEQ ID NO:80)

HRV25_A    :N-------------PIENYVDQVLN-----------EVLVVPNIKESHP-STSNSAPILDAAETGHTSNVQPEDTIETRYVQTTQTRDEMSIESFLGRSGCVHTSTIET-KLK------- 87
(SEQ ID NO:81)

HRV8_A     :N-------------PIEQFTEAVLN-----------EVLVVPNTQASNG-SIANSAPALDAAETGHTSSVQPEDLIETRYVITDQTRHETSLESFLGRAGCIKIIALELDHDNYD----- 90
(SEQ ID NO:82)

HRV_C_026  :N-------------PVEEFVEHTLK-----------EVLVVPDTQASGP-VHTTKPQALGAVEIGATADVGPETLIETRYVMNDNTNAEATVENFLGRSALWANLKLNQ----------- 84
(SEQ ID NO:83)

COXA16G10  :G------------DGIADMIDQAVTSRVGRALTSLQVEPTAANTNASEHRLGTGLVPALQAAETGASSNAQDENLIETRCVLNHHSTQETTIGNFFSRAGLVSIITMPTTGTQNTDG---105
(SEQ ID NO:84)

ENTERO71   :G------------DRVADVIESSIGDSVSRALTRALPAPTGQDTQVSSHRLDTGKVPALQAAEIGASSNASDESMIETRCVLNSHSTAETTLDSFFSRAGLVGEIDLPLEGTTNPNG---105
(SEQ ID NO:85)

ENTERO68   :A------------AEAAYQIESIIK--------------TATDTVKSEISAELGVVPSLNAVETGASSNTEPEEAIQTRTVINQHGVSETLVENFLSRAALVSKRSFEYKNHTSSKARTD 94
(SEQ ID NO:86)

ENTERO70   :E------------QAATTQIGEIVK--------------TVANTVESDIKAELGVIPSLNAVETGATSNTEPEEAIQTRTVINMHGTAECLVENFLGRSALVCMRSFEYKNHSTSTSSIQ 94
(SEQ ID NO:87)

POL1M      :GLGQMLESMIDNTVRETVGAATSRD--------------ALPNTEASGP-THSKEIPALTAVETGATNPLVPSDTVQTRHVVQHRSRSESSIESFFARGACVTIMTVDNPASTTNKDK--103
(SEQ ID NO:88)

POL2L      :GLGDLIEGVVEGVTRNALTPLTPAN--------------NLPDTQSSGP-AHSKETPALTAVETGATNPLVPSDTVQTRHVIQKRTRSESTVESFFARGACVAIIEVDNDAPTKRASK--103
(SEQ ID NO:89)

POL323sp|P:GVDDLITEVAQNAL--ALSLPKPQS--------------NLPDTKASGP-AHSKEVPTLTAVETGATNPLVPSDTVQTRHVIQQRSRSESTIESFFARGACVAIIEVDNEQPATNVQK--101
(SEQ ID NO:90)
```

FIG. 14B

```
                     *        20         *        40         *        60         *        80         *       100         *       120
COXA24EH24:GIEETIDTVISNALQLSQPKPQKQL--------------TAQSTPSTSG-VNSQEVPALTAVETGVSGQAIPSDVIETRHVVNYKTRSESTLESFFGRSACVTMLEVENFNATTEADKK-104
(SEQ ID NO:91)

ECHO12    :G-------------DVEEAVNRAVA--------------RVADTLPTGP-RNSESIPALTAAETGHTSQVVPGDTMQTRHVKNYHSRTESSVENFLCRAACVYITKYKTK-DSDPVQ--- 88
(SEQ ID NO:92)

ECHO3     :G-------------DVEEAIDRAVA--------------RVADTMPTGP-RNTESVPALTAVETGHTSQVVPGDTMQTRHVKNYHSRTESSIENFLCRAACVYITTYKSA-GGTPTE--- 88
(SEQ ID NO:93)

COXA9-Grig:G-------------DVEEAIERARC--------------TVADTMRTGP-SNSASVPALTAVETGHTSQVTPSDTMQTRHVKNYHSRSESTVENFLGRSACVYMEEYKTT-DKHVNK--- 88
(SEQ ID NO:94)

ECHO11    :G-------------DVVEAIEGAVA--------------RVADTISNGP-TNSQAVPALTAVETGHTSQVVPSDTMQTRHVKNYHSRSESTIENFLSRSACVYMGEYYTT-NTDETK--- 88
(SEQ ID NO:95)

ECHO19    :G-------------DVVKAIEGAVS--------------RVADTISSGP-SNSQAVPALTAVETGHTSQVVPSDTMQTRHVKNYHSRSESSIENFLSRSACVYMGEYKTK-ASEETK--- 88
(SEQ ID NO:96)

ECHO7     :G-------------DTETAIDNAIA--------------RVADTVASGP-SNSTSIPALTAVETGHTSQVEPSDTMQTRHVKNYHSRSESTVENFLSRSACVYIEEYYTK-DQDNVN--- 88
(SEQ ID NO:97)

ECHO32    :N-------------DPATAIEGAVR--------------RVADTIQSGP-SNSERVPALTAVETGHTAQVTPSDTMQTRHVHNFHTRSESSIENFLSRAACVYIGKYSSN-ATTQDE--- 88
(SEQ ID NO:98)

COXB1Japan:G-------------PVEESVERAMV--------------RVADTVSSKP-TNSESIPALTAAETGHTSQVVPSDTMQTRHVKNYHSRSESSIENFLCRSACVYYATYNNNS--EKG---- 86
(SEQ ID NO:99)

COXB3-Nan :G-------------PVEDAITAAIG--------------RVADTVGTGP-TNSEAIPALTAAETGHTSQVVPGDTMQTRHVKNYHSRSESTIENFLCRSACVYFTEYKNSG--AKR---- 86
(SEQ ID NO:100)

COXB5Peter:G-------------PPGEAVERAIA--------------RVADTISSGP-VNSESIPALTAAETGHTSQVVPADTMQTRHVKNYHSRSESTVENFLCRSACVYYTTYKNHG--TDGD--- 87
(SEQ ID NO:101)

COXB6Schmi:S-------------PVEGAIERAIA--------------RVADTMPSGP-TNSEAVPALTAVETGHTSQVVPSDNMQTRHVKNYHSRSETSVENFLCRSACVYFTTYKNQT--GATN--- 87
(SEQ ID NO:102)
```

Fig. 14C

```
                         *        20         *        40         *        60         *        80         *       100         *       120
COXB2-O1   :S-------------PVEESIERSIG--------------RVADTIGSGP-SNSEAIPVLTAVETGHTSQVTPSDTMQTRHVHNYHSRSESSVENFLARSACVFYTTYTNSKNAAKEK--- 89
(SEQ ID NO:103)

COXB4-E2   :G-------------PTEESVERAMG--------------RVADTIARGP-SNSEQIPALTAVETGHTSQVDPSDTMQTRHVHNYHSRSESSIENFLCRSACVIYIKYSSAE-SNNLK--- 88
(SEQ ID NO:104)

ECHO13     :G-------------DKASEVT-------------------VSDTQPSGP-SNSVSIPMLTAAETGHTSQAVPSDTIQTRCVLNRHKRSESSIENFLCRSACVYYTTYDTH-GDAADA--- 83
(SEQ ID NO:105)

ENTERO69   :N-------------DQHNGAI-------------------VANTTASGP-SNSESIPALTAAETGHTSQVVPSDTIQTRHVKNYHSRSESTIENFLCRSACVYYTTYNTQ-GEQAHD--- 83
(SEQ ID NO:106)

ECHO21     :N-------------DPAQAVLSAIG--------------RVADTVASGP-SNSERVPVLTAAETGHTSQVVPSDTIQTRHVVNFHTRSESTIENFMCRSACVYIARYGTEKQGEQIS--- 89
(SEQ ID NO:107)

ECHO30     :N-------------DPESALNRAVG--------------RVADTIASGP-VNTEQIPALTAVETGHTSQVVPSDTMQTRHVVNYHTRSESSIENFMGRAACVYIAQYATEKVNDELD--- 89
(SEQ ID NO:108)

ECHO25     :N-------------DPATAIVRSVE--------------RVADTIASGP-MNSERVPALTAVETGHTSQVVPSDTMQTRHVVNHHIRSESSIENFLSRSACVYIDVYGTKENGD-IK--- 88
(SEQ ID NO:109)

ECHO29     :N-------------EPSSAIERAIV--------------RVADTMASGP-ANSEQIPALTAAETGHTSQVVPSDTMQTRHVCNYHTRSESSIENFLCRAACVYIVSYKTQ-GDEQTD--- 88
(SEQ ID NO:110)

ECHO6      :N-------------DVQNAVERSIV--------------RVADTLPSGP-SNSESIPALTAAETGHTSQVVPSDTIQTRHVRNFHVRSESSVENFLSRSACVYIVEYKTQ-DTTPDK--- 88
(SEQ ID NO:111)

ECHO20     :G-------------DVHDAVVGAMT--------------RVADTISSGP-SNSESVPALTAAETGHTSQVVPSDTMQTRHVRNFHTRSESSIENFMSRSACVYYTKYKTK-DPDPTE--- 88
(SEQ ID NO:112)

ECHO24     :G-------------DVCEEVERAIT--------------RVADTVGRGP-ANTESVPALTAVETGHTSQVVPGDTMQTRHVKNFHTRSESSVENFMCRAACVYYVDYHTQ-NDSEDE--- 88
(SEQ ID NO:113)
```

Fig. 14D

```
                        *        20         *        40         *        60         *        80         *       100         *       120
ECHO4      :G-------------DVQDAVTGAIV--------------RVADTLHTGP-TNNEAIPNLTAVETGHTSQVTPGDTMQTRHVINMHTRSESSIENFLARAACVYYLNYQTG-SGPGTQ--- 88
(SEQ ID NO:114)

ECHO16     :G-------------EPGKAIESAIS--------------RVADTISSGP-TNSEQVPALTAAETGHTSQVVPGDTIQTRHVKNYHSRSESTIENFLCRSACVHIARYEAGANANNE---- 88
(SEQ ID NO:115)

ECHO31     :G-------------DTEHAVESAIS--------------RVADTISSGP-SNTVAIPALTAAETGHTSQVTPSDNLQTRHVKNYHSRSESTIENFLCRSACVHIASYNAYGDVGSD---- 88
(SEQ ID NO:116)

ECHO14     :N-------------DPEQAIDRALA--------------RVADTVRSGP-SNSEQIPALTAVETGHTSQVVPSDTMQTRHVKNYHSRSESTIENFLCRSACVHIATYKAKGGAGDV---- 88
(SEQ ID NO:117)

ECHO15     :G-------------DDQHKTN------------------TVTDTEQSGP-SNSERVPALTAVETGHTSQVVPSDTVQTRHVRNYHSRTESTLENFLGRSACVHIDTYKAKGEKGSS---- 84
(SEQ ID NO:118)

ECHO2      :G-------------DEVKHEP------------------TVANTTASGP-SNSQQVPALTAVETGHTSQVVPSDTIQTRHVHNYHSRTESTLENFLGRSACVHIDSYKTKGVTGES---- 84
(SEQ ID NO:119)

ECHO18     :G-------------DNQ------DR--------------TVANTQPSGP-SNSTEIPALTAVETGHTSQVDPSDTIQTRHVVNFHSRSESTIENFMGRAACVFMDQYKINGEETST---- 82
(SEQ ID NO:120)

ECHO17     :G-------------DVEDSVNRAVV--------------RVADTMPSGP-SNSQAVPALTAAETGHTSQVVPGDNIQTRHVHNYHSRTESSIENFFGRSACVVVKTYKMGQKVVAT---- 88
(SEQ ID NO:121)

ECHO27     :G-------------DDARTVS---------------------NTQKSQP-SNSEQVPALTAVETGHTSQVEPSDTVQTRHVVNSHSRTESTIENFFGRAACVRVREYSIGHDLAAD---- 81
(SEQ ID NO:122)

ECHO26     :G-------------DDPPHSIS--N--------------TVANTNPSGP-TNSERIPALTAAETGHTSQVVPSDTVQTRCVKNFHTRSESSIENFLCRSACAHMSSYEAFPTTTQDGT-- 88
(SEQ ID NO:123)

ECHO1-Bry  :G-------------DVQNAVEGAMV--------------RVADTVSTSA-TNSEQVPNLTAVETGHTSQVVPGDTMQTRHVVNKHVRSESTIENFLARSACVYFLEYETGTKTDSNA--- 89
(SEQ ID NO:124)
```

Fig. 15

```
                                *          20          *          40          *          60
HRV14_B      : MGAQVSTQKSGSHENQNILTNGSNQTFTVINYYKDAASTSSAGQSLSMDPSKFTEPVKDLMLKGAPALN : 69 (SEQ ID NO:125)
HRV100_A     : MGAQVSRQNVGTHSTQNTVSNGSSLNYFNINYFKDAASSGASKLEFSQDPSKFTDPVKDVLEKGIPTLQ : 69 (SEQ ID NO:126)
HRV25_A      : MGAQVSRQNVGTHSTQNSVSNGSSLNYFNINYFKDAASSGASKLEFSQDPSKFTDPVKDVLEKGIPTLQ : 69 (SEQ ID NO:127)
HRV8_A       : MGAQVSRQNVGTHSTQNAVSGGSSLNYFNINYFKDAASSGASRLDFSQDPSKFTDPVKDVLTKGIPTLQ : 69 (SEQ ID NO:128)
HRV_C_026    : MGAQVSRQSVGSHETMIHAGTGAVVKYFNVNYYKDAASSGLTKQDFSQDPSKFTQPVADILSN--PALM : 67 (SEQ ID NO:129)
COXA16-G10   : MGSQVSTQRSGSHENSNSASEGSTINYTTINYYKDAYAASAGRQDMSQDPKKFTDPVMDVIHEMAPPLK : 69 (SEQ ID NO:130)
ENTERO71     : MGSQVSTQRSGSHENSNSATEGSTINYTTINYYKDSYAATAGKQSLKQDPDKFANPVKDIFTEMAAPLK : 69 (SEQ ID NO:131)
ENTERO68     : MGAQVTRQQTGTHENANIATNGSHITYNQINFYKDSYAASASKQDFSQDPSKFTEPVVEGLKAGAPVLK : 69 (SEQ ID NO:132)
ENTERO70     : MGAQVSRQQTGTHENANVATGGSSITYNQINFYKDSYAASASKQDFSQDPSKFTEPVAEALKAGAPVLK : 69 (SEQ ID NO:133)
POL1M        : MGAQVSSQKVGAHENSNRAYGGSTINYTTINYYRDSASNAASKQDFSQDPSKFTEPIKDVLIKTAPMLN : 69 (SEQ ID NO:134)
POL2L        : MGAQVSSQKVGAHENSNRAYGGSTINYTTINYYRDSASNAASKQDFAQDPSKFTEPIKDVLIKTAPTLN : 69 (SEQ ID NO:135)
POL3-23sp|P  : MGAQVSSQKVGAHENSNRAYGGSTINYTTINYYKDSASNAASKQDYSQDPSKFTEPLKDVLIKTAPALN : 69 (SEQ ID NO:136)
COXA24-EH24  : MGAQVSSQKVGAHENTNVATGGSTVNYTTINYYKDSASNAASKLDFSQDPSKFTEPVKDIMLKSAPALN : 69 (SEQ ID NO:137)
ECHO12       : MGAQVSTQKTGAHETGLSASGNSIIHYTNINYYKDAASNSANRQDFTQDPGKYTEPVKDIMIKSMPALN : 69 (SEQ ID NO:138)
ECHO3        : MGAQVSTQKTGAHETGLTASGNSTIHYTNINYYKDAASNSANRQDFTQDPSKFTEPMKDVMIKSLPALN : 69 (SEQ ID NO:139)
COXA9-Grig   : MGAQVSTQKTGAHETSLSAAGNSIIHYTNINYYKDAASNSANRQDFTQDPSKFTEPVKDVMIKSLPALN : 69 (SEQ ID NO:140)
ECHO11       : MGAQVSTQKTGAHETGLNASGSSIIHYTNINYYKDAASNSANRQDFTQDPGKFTEPVKDIMIKSMPALN : 69 (SEQ ID NO:141)
ECHO19       : MGAQVSTQKTGAHETGLNASGNSIIHYTNINYYKDAASNSANRQDFTQDPGKFTEPVKDIMIKSMPALN : 69 (SEQ ID NO:142)
ECHO7        : MGAQVSTQKTGAHETGLNASGNSIIHYTNINYYKDAASNSANRQDFTQDPGKFTEPVKDIMIKTMPALN : 69 (SEQ ID NO:143)
ECHO32       : MGAQVSTQKTGAHETGLSASGSSIIHYTNINYYKDAASNSANRQDFSQDPSKFTEPVKDIMIKSMPALN : 69 (SEQ ID NO:144)
COXB1-Japan  : MGAQVSTQKTGAHETGLNASGNSIIHYTNINYYKDAASNSANRQDFTQDPGKFTEPVKDIMIKSMPALN : 69 (SEQ ID NO:142)
COXB3-Nan    : MGAQVSTQKTGAHETRLNASGNSIIHYTNINYYKDAASNSANRQDFTQDPGKFTEPVKDIMIKSLPALN : 69 (SEQ ID NO:145)
COXB5-Peter  : MGAQVSTQKTGAHETGLRASGNSIIHYTNINYYKDAASNSANRQEFAQDPGKFTEPVKDIMIKSMPALN : 69 (SEQ ID NO:146)
COXB6-Schmi  : MGAQVSTQKTGAHETALNAQGNSVIHYTNINYYKDAASNSANRQDFTQDPSKFTEPVKDVMIKSLPALN : 69 (SEQ ID NO:147)
COXB2-O1     : MGAQVSTQKTGAHETGLSASGGSIIHYTNINYYKDAASNSANRQDFTQDPGKFTEPVKDIMIKSMPALN : 69 (SEQ ID NO:148)
COXB4-E2     : MGAQVSTQKTGAHETSLSATGNSIIHYTNINYYKDAASNSANRQDFTQDPSKFTEPVKDVMIKSLPALN : 69 (SEQ ID NO:149)
ECHO13       : MGAQVSTQKTGAHETGLNASGNSVIHYTNINYYKDAASNSANRQDFTQDPSKFAEPMKDVMIKTLPALN : 69 (SEQ ID NO:150)
ENTERO69     : MGAQVSTQKTGAHETGLNASGNSIIHYTNINYYKDAASNSANRQDFTQDPSKFAEPMKDVMIKTLPALN : 69 (SEQ ID NO:151)
ECHO21       : MGAQVSTQKTGAHETSLNASGNSVIHYTNINYYKDSASNSANRQDFTQDPSKFTEPVKDVMIKSLPALN : 69 (SEQ ID NO:152)
ECHO30       : MGAQVSTQKTGAHETGLNASGNSTIHYTNINYYKDSASNSLNRQDFTQDPSKFTEPVKDVMVKTLPALN : 69 (SEQ ID NO:153)
ECHO25       : MGAQVSTQKTGAHETGLSANGNSVIHYTNINYYKDAASNSANRQDFSQDPSKFTEPMKDVMIKSLPALN : 69 (SEQ ID NO:154)
ECHO29       : MGAQVSTQKTGAHETGLNASGNSIIHYTNINYYKDAASNSANRQDFSQDPSKFTEPVKDVMIKTLPALN : 69 (SEQ ID NO:155)
ECHO6        : MGAQVSTQKTGAHETGLSASGNSIIHYTNINYYKDAASNSANRQDFTQDPGKFTEPVKDIMAKTLPALN : 69 (SEQ ID NO:156)
ECHO20       : MGAQVSTQKTGAHETGLNASGNSIIHYTNINYYKDAASNSANRQDFTQDPSKFTEPVKDVMIKSLPALN : 69 (SEQ ID NO:157)
ECHO24       : MGAQVSTQKTGAHETSLSASGNSIIHYTNINYYKDAASNSANRQDFSQDPSKFTEPMKDIMVKSLPALN : 69 (SEQ ID NO:158)
ECHO4        : MGAQVSTQKTGAHETGLNASGSSIIHYTNINYYKDAASNSANRQDFTQDPSKFTEPVKDIMIKSLPALN : 69 (SEQ ID NO:159)
ECHO16       : MGAQVSTQKTGAHETLLEAAQGATINYTNINYYKDAASNSANRQDFSQDPSKFTEPVKDIMIKSMPALN : 69 (SEQ ID NO:160)
ECHO31       : MGAQVSTQKTGAHETLLEAAQGATINYTNINYYKDAASNSANRQDFTQDPGKFTEPVKDLMIKSMPALN : 69 (SEQ ID NO:161)
ECHO14       : MGAQVSTQKTGAHETGLNAQGNSVIHYTNINYYKDAASNSANRQDFQQDPGKFTEPMKDIMIKSLPALN : 69 (SEQ ID NO:162)
ECHO15       : MGAQVSTQKTGAHETSLNTGNSSIIHYTNINYYKDAASNSSNRQDMDQDPSKFTEPVMDIMVKSLPALN : 69 (SEQ ID NO:163)
ECHO2        : MGAQVSSQKVGAHETKLNTGNNSTINYTNINYYKDAASNSSNRQTLEQDPSKFTEPVLDVMVKSLPALN : 69 (SEQ ID NO:164)
ECHO18       : MGAQVSTQKTGAHETSLSAKGNSIIHYTNINFYKDAASSASNRQDIQQDPGKFTDPVKDLMIKTLPALN : 69 (SEQ ID NO:165)
ECHO17       : MGAQVSTQKTGAHETGLNASGNSVIHYTNINYYKDAASNSANRQDFTQDPSKFTEPVKDIMIKSMPALN : 69 (SEQ ID NO:166)
ECHO27       : MGAQVSTQKTGAHETSVNATGSSIVHYTNINFYKDAASNSSNRQDMSQDPAKFTEPVKDIMLKSLPALN : 69 (SEQ ID NO:167)
ECHO26       : MGAQVSTQKTGAHETSLNASGSSVIHYTNINFYKDAASNSANRQDFSQDPSKFTEPLKDVMIKSLPALN : 69 (SEQ ID NO:168)
ECHO1-Bry    : MGAQVSTQKTGAHETGLNANGNSIIHYTNINYYKDAASNSANRQDFTQDPGKFTEPVKDVMIKTLPALN : 69 (SEQ ID NO:169)
```

Fig. 16A

```
                                                          BssHII
                                                     AvrII
                                                  StuI   AscI      NcoI
     CTCACTATAGGGCGAATTGAAGGAAGGCCGTCAAGGCCTAGGCGCGCCACCATGGTTGGT
  1  ---------*---------*---------*---------*---------*---------*
     GAGTGATATCCCGCTTAACTTCCTTCCGGCAGTTCCGGATCCGCGCGGTGGTACCAACCA
                                                         M__V__G__

     GCTCAAGTTTCCACTCAAAAGTCTGGTTCCCACGAGAACCAGAACATCTTGACTAACGGT
 61  ---------*---------*---------*---------*---------*---------*
     CGAGTTCAAAGGTGAGTTTTCAGACCAAGGGTGCTCTTGGTCTTGTAGAACTGATTGCCA
     A__Q__V__S__T__Q__K__S__G__S__H__E__N__Q__N__I__L__T__N__G__

                                               BspHI   PacI
     TCCAACCAGACTTTCACTGTTATCAACTACCTCATGAATTAATTAACTGGCCTCATGGGC
121  ---------*---------*---------*---------*---------*---------*
     AGGTTGGTCTGAAAGTGACAATAGTTGATGGAGTACTTAATTAATTGACCGGAGTACCCG
     S__N__Q__T__F__T__V__I__N__Y__L__M_(SEQ ID NO:170)_

     CTTCCTTTCACTGCCCGCTTTCCAGT   (SEQ ID NO:171)
181  ---------*---------*------
     GAAGGAAAGTGACGGGCGAAAGGTCA    (SEQ ID NO:172)
```

Fig. 17A

1 ATGGTT*GGTG CTCAAGTTTC CACTCAAAAG TCTGGTTCCC ACGAGAACCA GAACATCTTG*

*61 ACTAACGGTT CCAACCAGAC TTTCACTGTT ATCAACTAC*c ccgtgaccaa cATGGAAAAC

121 ATCACCTCTG GTTTCTTGGG TCCATTATTG GTTTTACAAG CTGGTTTCTT CTTGTTGACC

181 AGAATTTTAA CTATTCCACA ATCTTTGGAC TCATGGTGGA CCTCCTTGAA CTTCTTGGGT

241 GGTTCTCCAG TTTGTTTGGG TCAAAACTCC CAATCCCCAA CTTCCAACCA TTCTCCTACT

301 TCTTGTCCAC CAATCTGTCC AGGTTACAGA TGGATGTGTT TGAGAAGATT TATCATTTTC

361 TTGTTCATCC TATTGTTGTG TTTGATCTTC CTATTGGTTT TGTTGGATTA CCAAGGTATG

421 TTACCAGTTT GTCCATTGAT CCCAGGTTCC ACTACTACCA ACACTGGTCC ATGTAAGACC

481 TGTACTACTC CAGCTCAAGG TAACTCAATG TTTCCATCTT GTTGTTGTAC CAAGCCAACC

541 GACGGTAACT GTACTTGTAT CCCAATTCCA TCTTCCTGGG CTTTCGCTAA GTACTTGTGG

601 GAATGGGCTT CCGTTAGATT CTCTTGGTTG TCTTTGTTGG TTCCATTCGT TCAATGGTTC

661 GTTGGTTTGT CCCCAACCGT CTGGTTGTCT GCTATCTGGA TGATGTGGTA CTGGGGTCCA

721 TCTTTGTACT CTATCGTCTC TCCATTCATC CCATTGTTAC CAATCTTCTT CTGTTTGTGG

781 GTCTACATTT AA (SEQ ID NO:12)

Fig. 17B

1 MV*GAQVSTQK SGSHENQNIL TNGSNQTFTV INY*pvtnMEN ITSGFLGPLL VLQAGFFLLT

61 RILTIPQSLD SWWTSLNFLG GSPVCLGQNS QSPTSNHSPT SCPPICPGYR WMCLRRFIIF

121 LFILLLCLIF LLVLLDYQGM LPVCPLIPGS TTTNTGPCKT CTTPAQGNSM FPSCCCTKPT

181 DGNCTCIPIP SSWAFAKYLW EWASVRFSWL SLLVPFVQWF VGLSPTVWLS AIWMMWYWGP

241 SLYSIVSPFI PLLPIFFCLW VYI (SEQ ID NO:13)

Fig. 18A

1 ATGGTTGAGA ACATCACTTC CGGTTTCTTG GGACCATTGT TGGTTTTGCA GGCTGGATTC

61 TTCTTATTGA CTAGAATCTT GACTATCCCA CAGTCTTTGG ACTCTTGGTG GACTTCCTTG

121 AACTTCTTGG GAGGTTCTCC AGTTTGTTTG GGACAAAACT CCCAATCTCC AACTTCTAAC

181 CACTCCCCAA CTTCATGTCC ACCAATCTGT CCAGGTTACA GATGGATGTG TTTGAGAAGA

241 TTCATCATTT TCTTGTTCAT CTTGTTGTTG TGTTTGATCT TCTTGTTGGT TTTGTTGGAC

301 TACCAGGGAA TGTTGCCAGT TTGTCCATTG ATTCCAGGTT CCACTACTAC AAACACTGGT

361 CCATGTAAGA CTTGTACTAC TCCAGCTCAG GGAAACTCTA TGTTCCCATC CTGTTGTTGT

421 ACTAAGCCAA CTGACGGTAA CTGTACTTGT ATCCCAATTC CATCCTCTTG GGCTTTCGCT

481 AAGTACTTGT GGGAATGGGC TTCTGTTAGA TTCTCCTGGT TGTCCTTGTT GGTTCCATTC

541 GTTCAGTGGT TCGTTGGTTT GTCTCCAACT GTTTGGTTGT CCGCTATCTG GATGATGTGG

601 TACTGGGGAC CATCTTTGTA CTCCATCGTT TCCCCATTCA TCCCATTGTT GCCAATCTTT

661 TTCTGTTTGT GGGTTTACAT CTAG (SEQ ID NO:14)

Fig. 18B

1 MVENITSGFL GPLLVLQAGF FLLTRILTIP QSLDSWWTSL NFLGGSPVCL GQNSQSPTSN

61 HSPTSCPPIC PGYRWMCLRR FIIFLFILLL CLIFLLVLLD YQGMLPVCPL IPGSTTTNTG

121 PCKTCTTPAQ GNSMFPSCCC TKPTDGNCTC IPIPSSWAFA KYLWEWASVR FSWLSLLVPF

181 VQWFVGLSPT VWLSAIWMMW YWGPSLYSIV SPFIPLLPIF FCLWVYI (SEQ ID NO:15)

FIG. 19

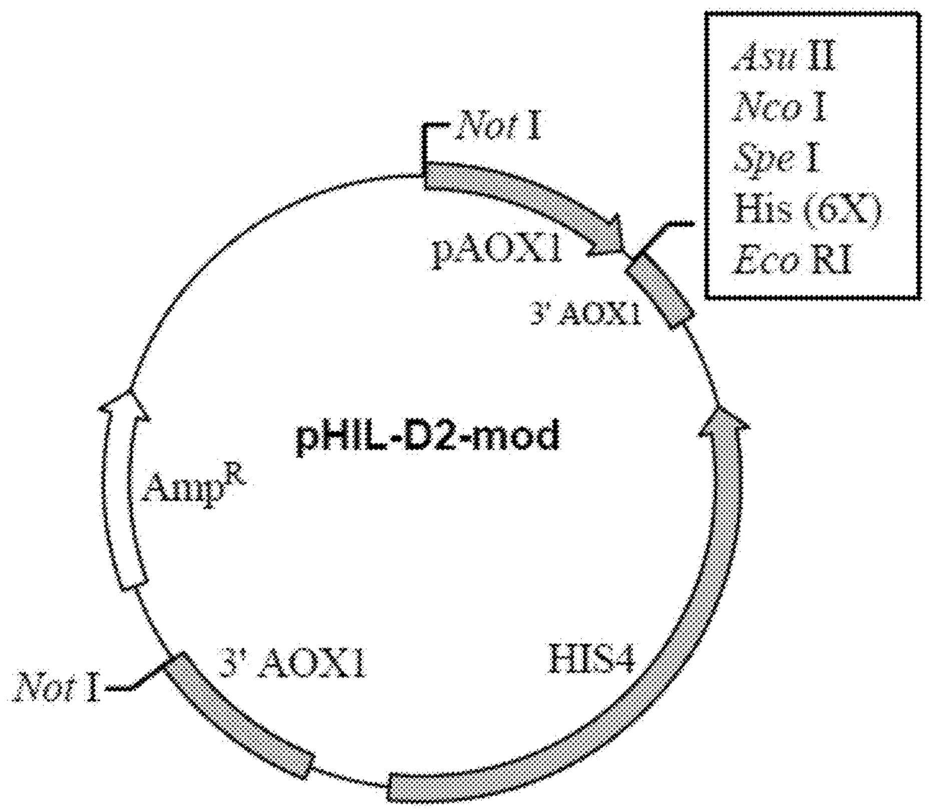

Native ATG start codon of AOX1 gene:

*Asu* II
TTCGAAACG.ATG (SEQ ID NO:173)

*Eco*RI cloning site in PHIL-D2 vector (Invitrogen):

*Asu*II
TTCGAAACG*AGGAATTC*.ATG (SEQ ID NO:174)
Extraneous sequences in the 5'UTR are in italics MCS POLYLINKER in PHIL-D2-mod:

*Asu*II *Nco* I *Spe*I *Eco*R I
TTCGAA.ACC.ATGGCCGCGGACTAGT.GGC.CAC.CAT.CAC.CAT.CAC.CAT.TAA.CGCGAATTC (SEQ ID NO:175)
Thr . Ser . Gly. His. His. His. His. His. His (SEQ ID NO:176)

Figure 20: Plasmid map of PHIL-D2mod/VP4-S recombinant vector
Integration was performed by cutting recombinant plasmid with NotI restriction enzyme. *NotI* fragment containing the VP4-S expression cassette plus the selection marker were used to transform GS115 strain.
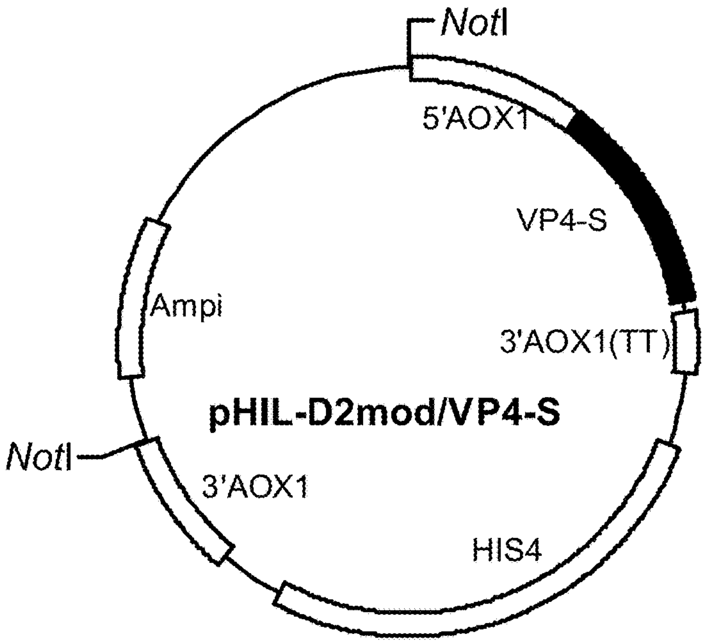

Figure 21: Plasmid map of PHIL-D2mod/S recombinant vector
Integration was performed by cutting recombinant plasmid with *NotI* restriction enzyme. *NotI* fragment containing the S expression cassette plus the selection marker was used to transform GS115 strain.
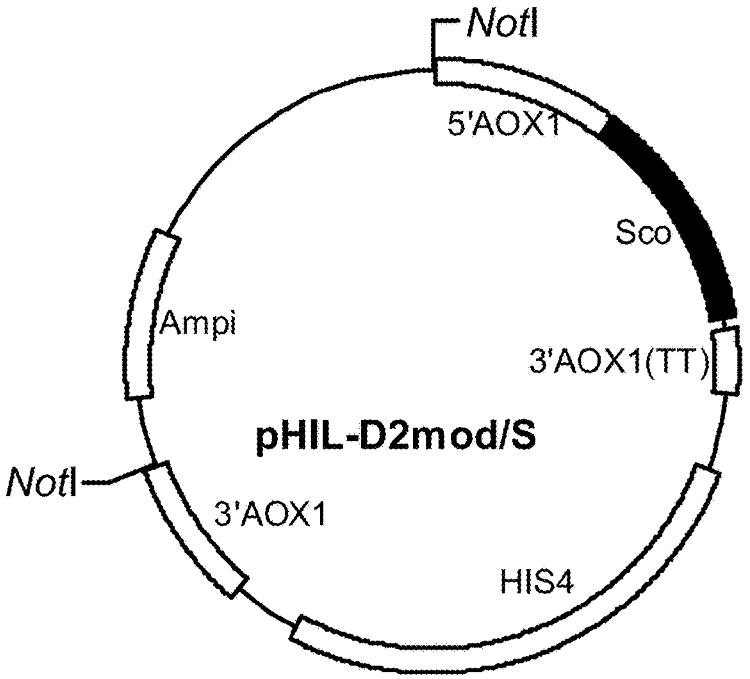

Figure 22: CsCl gradient analysis
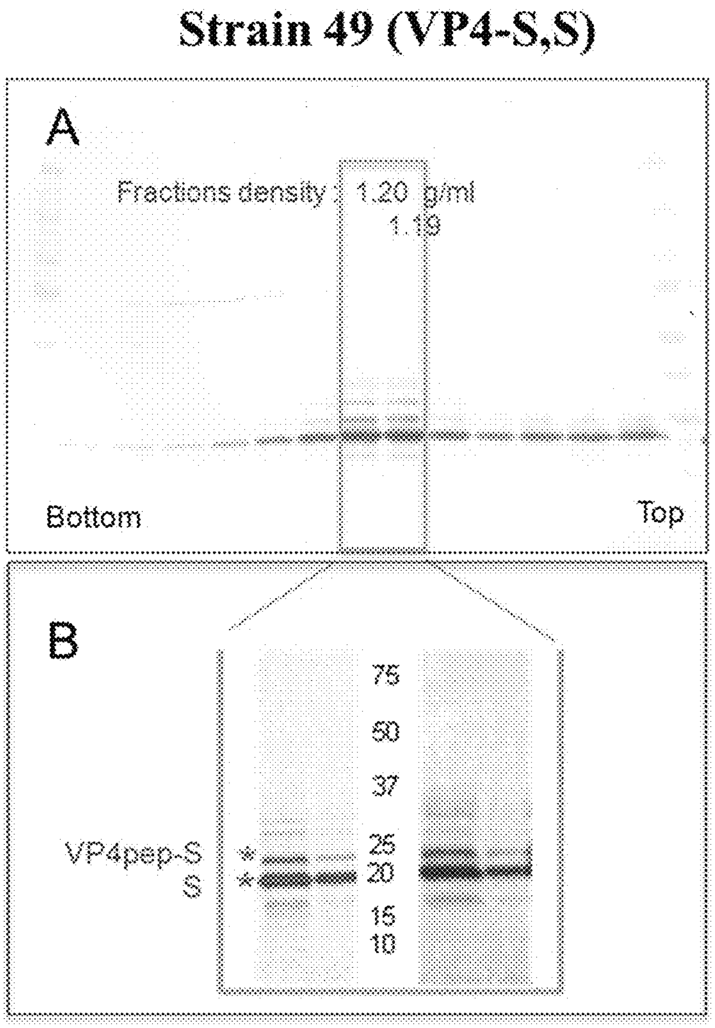

Figure 23: BMP 201 purified bulk
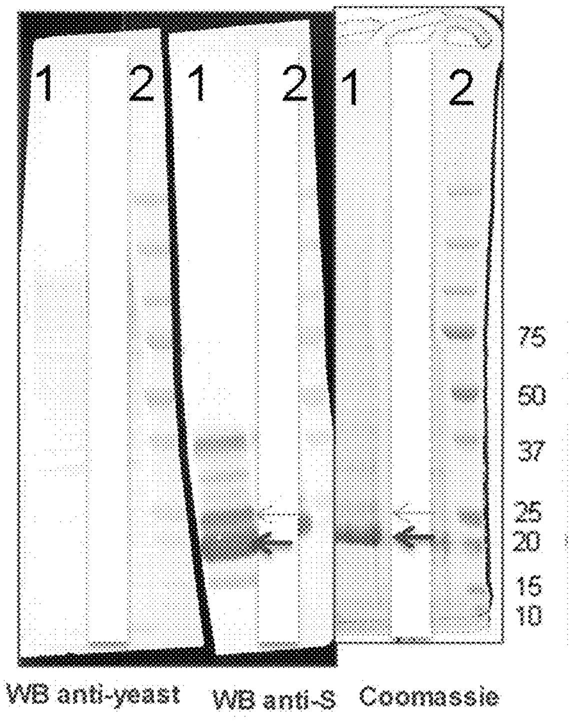
1: BMP201
2: MW markers

Figure 24: EM analysis performed on BMP201
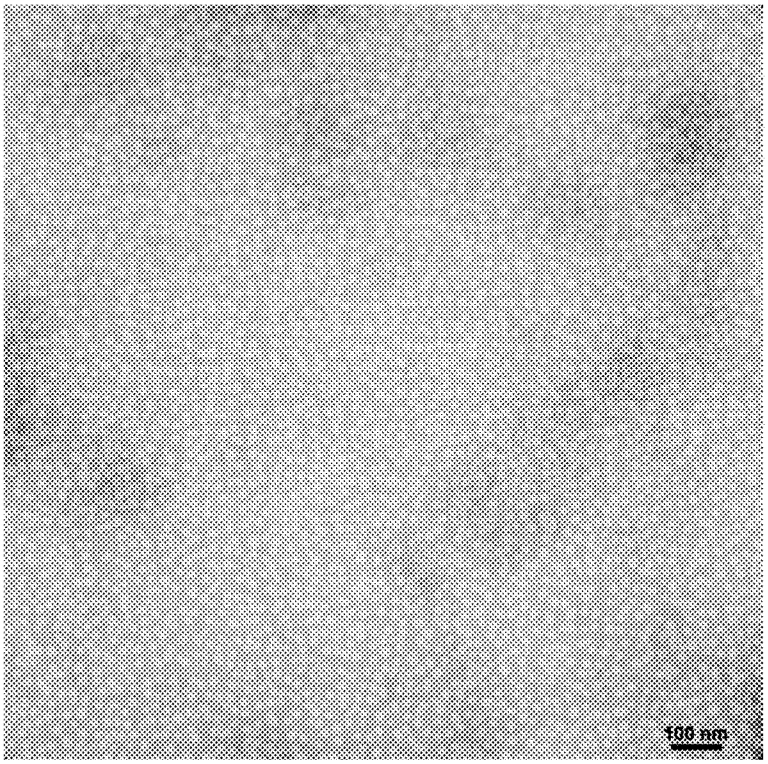
Negative staining with phosphotungstic acid

VACCINE

This application is the US National Stage of International Application No. PCT/EP2014/054947, filed 13 Mar. 2014, which claims benefit of the filing date of US Provisional Application No. 61/786,765, filed 15 Mar. 2013. Both of which are incorporated herein by reference.

SEQUENCE LISTING

The instant application contains a Sequence Listing which has been submitted electronically in ASCII format and is hereby incorporated by reference in its entirety.

BACKGROUND

The present disclosure relates to the field of human vaccines. More particularly, the present disclosure relates to pharmaceutical and immunogenic compositions, for the prevention or treatment of human picornavirus infection or disease, in particular human rhinovirus (HRV) infection or disease.

Picornaviridae is one of the largest viral families and is composed of 14 genera, six of which include human pathogens. Well known picornaviruses are enteroviruses (including polio, and rhinoviruses), foot-and-mouth disease virus (FMDV), and hepatitis A virus (HAV). Other members of the Picornaviridae family are coxsackievirus, echovirus, human parechovirus and aichi virus. Picornaviridae cause illnesses like the common cold, gastroenteritis, heptatis, pneumonia, poliomyelitis, meningitis, hand-foot-and-mouth disease. Although infections often are mild, certain strains may cause pandemic outbreaks accompanied with meningitis and/or paralysis.

Rhinoviruses are the primary cause of acute upper respiratory tract infections in humans, known as the common cold. They are also the most common viral cause of severe exacerbation of chronic respiratory diseases such as asthma and chronic obstructive pulmonary disease (COPD). Currently there are over 100 HRV serotypes. There is little or no cross-protection between serotypes due to the existence of type specific immunodominant neutralising epitopes, and no vaccine has so far been developed. A rhinovirus vaccine, which would need to be able to protect against multiple serotypes, therefore represents a large unmet medical need.

BRIEF SUMMARY

The present disclosure relates to vaccines against human picornavirus which contain antigens which provide protection against different picornaviruses, either from different serotypes or strains of the same picornavirus, or from different members of the picornavirus family. Specific embodiments relate to vaccines against human enteroviruses in particular rhinovirus containing antigens which provide protection against different enterovirus or HRV serotypes. The vaccines contain picornavirus peptides from conserved regions of the structural proteins of picornaviruses, which generate a cross-reactive or cross-neutralising response to provide cross-protection against a range of picornaviruses, for example against a range of different HRV serotypes.

The invention provides an immunogenic composition comprising a first and second peptide derived from structural protein of a picornavirus, said peptides each capable of inducing a cross-neutralising immune response against two or more picornaviruses, and a pharmaceutically acceptable diluent, excipient or carrier.

Certain novel picornavirus and rhinovirus peptides from VP4 and VP1 are further provided herein.

In a further aspect the invention provides a picornavirus peptide consisting of no more than 20 amino acids from the N terminus of VP4, which peptide includes amino acids 1-16 of VP4 or a variant of amino acids 1-16 having 1-4 amino acid additions or deletions at either end.

In a further aspect the invention provides a picornavirus peptide consisting of no more than 40 amino acids from the N terminal region of VP1, which peptide includes amino acids 32-45 or a variant of amino acids 32-45 having 1-4 amino acid additions or deletions at either end.

In a further aspect the invention provides a chimeric polypeptide particle comprising a backbone polypeptide capable of forming a particle and at least one peptide comprising an epitope of a picornavirus structural polypeptide.

In a further aspect the invention provides an immunogenic composition comprising a peptide or a chimeric polypeptide particle of the invention, together with a pharmaceutically acceptable diluent, excipient or carrier.

In a further aspect the invention provides the use of an immunogenic composition described herein, in the prevention or treatment of picornavirus infection such as HRV infection.

The invention further provides the use of an immunogenic composition described herein, in the manufacture of a medicament for the prevention or treatment of picornavirus infection such as HRV infection.

In a further aspect the invention provides a method for inducing neutralising antibodies against picornavirus such as HRV in humans comprising administering to a human an immunogenic composition as described herein.

In a further aspect the invention provides a method for inducing cross-neutralising antibodies against picornavirus such as HRV in humans comprising administering to a human an immunogenic composition described herein.

In a further aspect the invention provides a method for preventing picornavirus infection or picornavirus disease related to picornavirus infection, such as HRV infection or HRV disease related to HRV infection, which method comprises administering to a human an immunogenic composition as described herein.

In a further aspect the invention provides a method for preparing an immunogenic composition which method comprises combining (i) two or more picornavirus peptides from picornavirus structural proteins, said peptides each capable of inducing a cross-neutralising immune response against two or more picornaviruses or picornavirus serotypes, and (ii) a pharmaceutically acceptable diluent, excipient or carrier.

In a further aspect the invention provides a method for preparing an immunogenic composition which method comprises combining (i) a chimeric polypeptide particle comprising one or more picornavirus peptides derived from structural picornavirus proteins; and (ii) a pharmaceutically acceptable diluent, excipient or carrier.

BRIEF DESCRIPTION OF THE DRAWINGS

FIG. 1. shows a schematic diagram of the picornavirus genome.

FIG. 5. shows neutralising antibodies against various HRV strains, elicited in rabbits immunised with VP1 peptides conjugated to KLH.

FIG. 6. shows neutralising antibodies against various HRV strains, elicited in rabbits immunised with VP4 peptides conjugated to KLH or in a chimeric construct with HBsAg, or with full length concatamers of VP4.

FIG. 8. shows an alignment of VP1 amino acids 32-45 from different HRV clade A serotypes aligned to HRV14.

FIG. 9. shows an alignment of VP1 amino acids 32-45 from different HRV clade B serotypes aligned to HRV14.

FIG. 10. shows an alignment of VP1 amino acids 32-45 from different HRV clade C serotypes aligned to HRV14.

FIG. 11 shows an alignment of VP4 amino acids 1-16 from different HRV clade A serotypes aligned to HRV14.

FIG. 12. shows an alignment of VP4 amino acids 1-16 from different HRV clade B serotypes aligned to HRV14.

FIG. 13 shows an alignment of VP4 amino acids 1-16 from different HRV clade C serotypes aligned to HRV14.

FIGS. 14A, 14B, 14C and 14D show an alignment of the N-terminal residues of the VP1 proteins from some picornaviruses. The peptides similar to HRV14 32-45 are marked in the box.

FIG. 15 shows an alignment of the VP4 proteins from selected picornaviruses. The peptides are similar to the peptide HRV14 VP4 1-16 marked in the box.

FIG. 16A provides the VP4 synthetic DNA sequence (SEQ ID NO:171 and SEQ ID NO:172) encoding SEQ ID NO:170.

FIGS. 17A and 17B provide the nucleotide (SEQ ID NO:12) and amino acid (SEQ ID NO:13) sequences, respectively, of the VP4-S fusion, where bold letters indicate amino acids introduced by genetic construct (encoded by ATGGTT), italicized letters indicate a Human Rhinovirus strain HRV14:VP4 (capsid protein)-derived peptide of 31 amino acids, lower case letters indicate four amino acids from pre-S2, and the remaining letters indicate S protein (HBsAg).

FIGS. 18A and 18B provide the nucleotide sequence (SEQ ID NO:14) codon-optimized for expression in *Pichia pastoris*, designated the Sco gene (FIG. 18A), and coding for the S antigen (SEQ ID NO:15) (FIG. 18B).

FIG. 19—plasmid map of PHIL-D2mod vector.

FIG. 20—plasmid map of PHIL-D2mod/VP4-S recombinant vector. Integration was performed by cutting recombinant plasmid with Notl restriction enzyme, and Notl fragment containing the VP4-S expression cassette plus the selection marker were used to transform GS115 strain.

FIG. 21—plasmid map of PHIL-D2mod/S recombinant vector. Integration was performed by cutting recombinant plasmid with Notl restriction enzyme, and Notl fragment containing the S expression cassette plus the selection marker were used to transform GS115 strain.

FIG. 22A and 22B-CsC1 gradient analysis. Strain 49 (VP4-S,S).

FIG. 23—BMP 201 purified bulk. Lanes marked "1" are BMP201, lanes marked "2" are molecular weight markers.

FIG. 24—EM analysis performed on BMP201. Negative staining with phosphotungstic acid.

DETAILED DESCRIPTION

Introduction

Figure 2:
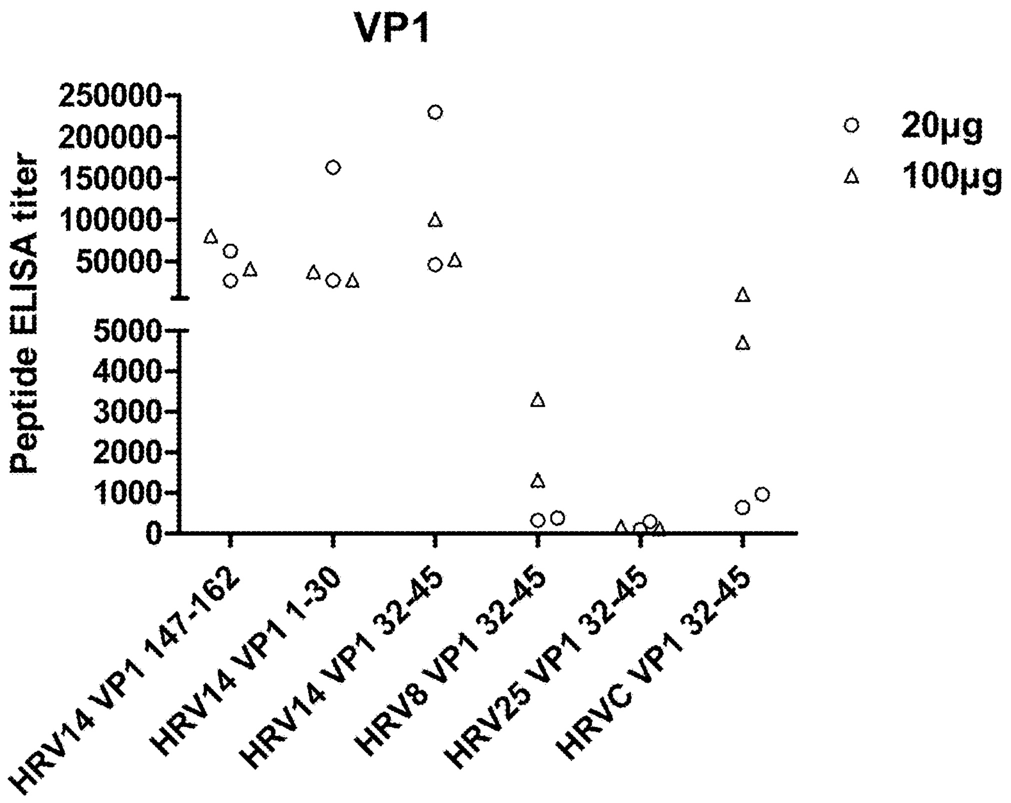
FIG. 2. shows peptide specific antibodies generated in rabbits immunised with VP1 peptides conjugated to KLH.

This disclosure concerns compositions and methods for the prevention and treatment of infection with a picornavirus, in particular a picornavirus from the genus of enteroviruses, more particularly a human enterovirus such as human rhinovirus (HRV).

Rhinoviruses are non-enveloped viruses and are composed of a capsid formed from four viral proteins VP1, VP2, VP3 and VP4. VP1, VP2, and VP3 form the major part of the protein capsid. The much smaller VP4 protein of approximately 70 amino acids in length has a more extended structure, and lies at the interface between the capsid and the RNA genome. The capsid is composed of 60 copies of each of these proteins assembled as an icosahedron.

The rhinovirus genome consists of a linear, single-stranded, positive sense RNA of between 7.2 and 8.5 kb in length. Structural proteins are encoded in the 5' region of the genome (starting from the 5' end: VP4, VP2, VP3 and VP1) and nonstructural at the 3' end, as is the case for all picornaviruses. The RNA is translated into a single polyprotein that is cleaved co-translationally and post-translationally into the four structural proteins and seven non structural proteins. The non structural genes are involved in processing the viral genome, viral replication, and shutting down the host cell protein production.

Currently there are over 100 HRV serotypes. Based on nucleotide identity and susceptibility of antiviral compounds HRVs have been classified into clades A, B, C and possibly D (Rollinger & Schmidtke, 2011; Palmenberg, Rathe & Liggett, 2010), see Table 1.

TABLE 1

| Clades | Receptor type | Serotypes numbers | Serotypes examples | Remarks |
|---|---|---|---|---|
| HRV-A | Major | 62 | 16 | |
| HRV-A | Minor | 12 | 1A, 1B, 2, 23, 25, 29, 30, 31, 44, 47, 49, 62 | |
| HRV-B | Major | 25 | 3, 14 | |
| HRV-C | ? | 7 | | New, emerging, clade |
| HRV87 | ? | 1 | | Same virus as Human Enterovirus 68, of species HEV-D (Blomqvist et al., 2002) |
| (HRV-D) | Major | 3 | 8, 45, 95 | Potentially separated clade (distinct from other clades based on VP3 and non-structural proteins but not VP1 and VP4) |

In addition host cell receptor specificity has been used to further classify these viruses into major and minor groups. Serotypes that use the intercellular adhesion molecule 1 (ICAM-1) receptor (62 HRV-A serotypes and all the B serotypes) belong to the major receptor group and the remaining 12 HRV-A serotypes use members of the low-density lipoprotein (LDL) receptor family and belong to the minor receptor group. Therefore the terms “HRV-A major”, “HRV-A minor”, and “HRV-B major” are used.

Serotypes are further classified by the antigenic sites they utilise to evade the host’s immune system. For the major receptor group four primary neutralising immunogienc (NIm) sites have been mapped to protruding regions on the external capsid proteins VP1, VP2 and VP3. These are known as NIm-IA, NIm-IB, NIm-II and NIm-III. For the minor receptor serotypes there are three distinct antigenic sites A, B and C that are located in the same vicinity as the NIm sites (reviewed in Lewis-Rogers et al 2009). It has been demonstrated that antibodies induced with recombinant HRV-14 or -89 VP1 proteins or a peptide spanning amino acids 147-162 of HRV14 VP1 exhibit specific and cross-neutralizing activity (McCray & Werner, 1998; Edlmayr et al., 2011). It has been observed that the rhinovirus capsid structure is dynamic and appears to oscillate between two different structural states: one in which the VP4 is deeply buried, and the other where the N-terminus of VP4 and VP1 are accessible to proteases (Lewis et al 1998). Antibodies raised against the 30 N terminal amino acids of VP4 but not VP1 were found to successfully neutralise viral infectivity in vitro (Katpally et al 2009). Antibodies raised against the N terminal 30 amino acids of VP4 were found to neutralise HRV14, HRV16 and HRV29. In addition, antibodies raised to a consensus sequence of the first 24 residues from rhinovirus VP4 also had some cross-neutralising activity (Katpally et al, 2009).

Other occurrences of rhinovirus peptides and/or epitopes in the literature can be found in: Niespodziana et al 2012 in which a response against an N terminal 20 mer from VP1 was not a neutralising response i.e. non protective epitope; Miao et al 2009—MAbs generated against the N terminal part of enterovirus VP1 which is highly conserved are useful in recognising a broad range of enteroviruses; WO 2006/078648 relating to peptides vaccines against HRV derived from the transiently exposed regions of VP4 in particular amino acids 1-31 or 1-24 of VP4; WO 2011/050384 relating to peptides from the N terminus of VP1 including amino acids 1-8; WO 2008/057158 relating to NIm IV of rhinovirus, in particular a peptide comprising amino acids 277-283 or 275-285 from the carboxyl terminal region of VP1, in particular from HRV-14.

The provision of a vaccine against HRV is a particular challenge due to the large number of serotypes of the virus and the lack of a protective response generated in individuals infected with one serotype against infection with another serotype. One important aspect of a vaccine against HRV that will protect against a sufficient number of HRV serotypes to provide effective protection against HRV infection, is the provision of epitopes from more than one HRV structural protein, for example from VP4 and from VP1. Another important aspect is the provision of peptides which are conserved among HRV serotypes. Another important aspect is the provision of peptides which generate a neutralising antibody response. Provided here are HRV peptides and combinations of HRV peptides from different HRV structural proteins, and constructs containing the peptides and combinations of peptides. In providing peptides which are conserved among HRV serotypes, the inventors have also discovered peptides that are remarkably conserved among picornaviruses in general.

Accordingly, this disclosure relates to peptides from picornavirus structural proteins which are selected as being capable of inducing a cross-neutralising immune response against different picornaviruses, which may be different picornaviruses or different serotypes from the same picornavirus, for example different rhinovirus serotypes. These peptides can be delivered in a number of ways including as peptides coupled or conjugated to carrier proteins such as CRM197, or in a chimeric construct with a polypeptide into which the peptide or peptides are inserted, for example a polypeptide which forms a particle such as a virus like particle, or a subviral particle.

In one embodiment, a combination of picornavirus peptides is provided which comprises first and second peptides from different picornavirus structural proteins. For example the first and second peptides can be from picornavirus VP4 and VP1. Favourably, the peptides are short peptides of no more than 20 amino acids, although they may be longer than this. In one embodiment the peptides are derived from the N terminal region of the structural proteins.

In an embodiment, the first and second peptides are from a human enterovirus and the enterovirus peptides are capable of inducing a cross-neutralising immune response against two or more enteroviruses. In a particular embodiment, one or both of the first and second peptides are from human rhinovirus and the rhinovirus peptides are capable of inducing a cross-neutralising immune response against two or more rhinovirus serotypes i.e. against the rhinovirus serotype from which the peptide is derived and at least one further rhinovirus serotype.

In one embodiment the first peptide is amino acids 32-45 from VP1 or a variant of amino acids 32-45 of VP1 having 1-4 amino acid additions or deletions at either end and/or 1-2 amino acid substitutions or additions or deletions within the peptide sequence.

In a particular embodiment the VP1 peptide is a human rhinovirus peptide and in particular with the peptide having a sequence selected from:

HRV14 (B): [SEQ ID NO: 1]
32-PILTANETGATMPV-45

HRV8 (A-M): [SEQ ID NO: 2]
32-PALDAAETGHTSSV-45

HRV25 (A-m): [SEQ ID NO: 3]
32-PILDAAETGHTSNV-45

HRV_C_026: [SEQ ID: 4]
32-QALGAVEIGATADV-45 or a variant thereof having 1-4 amino acid additions or deletions at either end and/or 1-2 amino acid substitutions or additions or deletions within the peptide sequence.

In one embodiment the second peptide is amino acids 1-16 from VP4 or a variant of amino acids 1-16 of VP4 having 1-4 amino acid additions or deletions at either end and/or 1-2 amino acid substitutions or additions or deletions within the peptide sequence.

In a particular embodiment the VP4 peptide is a human rhinovirus peptide and in particular with the peptide having a sequence selected from:

```
HRV14 (B):
                                    [SEQ ID NO: 5]
1-GAQVSTQKSGSHENQN-16

HRV100 (A-M):
                                    [SEQ ID NO: 6]
1-GAQVSRQNVGTHSTQN-16

HRV_C_026:
                                    [SEQ ID NO: 7]
1-GAQVSRQSVGSHETMI-16
```

or a variant thereof having 1-4 amino acid additions or deletions at either end and/or 1-2 amino acid substitutions or additions or deletions within the peptide sequence.

Also provided by the invention are individual picornavirus peptides for example the rhinovirus peptides with sequences given as SEQ ID NOs 1-7 and variants thereof as described herein.

Where a variant of a peptide sequence has 1-4 amino acid additions or deletions at either end and/or 1-2 amino acid substitutions or additions or deletions within the peptide sequence, this means that the variant has at least one amino acid difference compared to the reference peptide sequence, which may include between 0 and 4 amino acid additions or deletions at one end and between 0 and 4 additions or deletions at the other end and between 0 and 2 amino acid substitutions or additions or deletions within the sequence.

In one embodiment a picornavirus peptide provided herein consists of no more than 20 amino acids from the N terminus of VP4, which peptide includes amino acids 1-16 of VP4 or a variant of amino acids 1-16 having 1-4 amino acid additions or deletions at either end and/or 1-2 amino acid substitutions or additions or deletions within the peptide sequence. In a particular embodiment the VP4 peptide consists of amino acids 1-16 of VP4 or a variant having 1 or two or three or four amino acid additions or deletions or substitutions. Further specific VP4 peptides include for example amino acids 1 to [16-20], amino acids 2 to [17-21], 3 to [18-22], 4 to [19-23], 5 to [20-24] wherein it will be understood that the numbers in square brackets include all numbers in the specified range individually. Favorably, the VP4 peptide consists of no more than 16 contiguous amino acids from VP4. It should be understood that the numbering of the VP4 peptide as used herein is independent of methionine due to the startcodon.

In another embodiment a picornavirus peptide consists of no more than 40 amino acids from the N terminal region of VP1, which peptide includes amino acids 32-45 of VP1 or a variant of amino acids 32-45 having 1-4 amino acid additions or deletions at either end and/or 1-2 amino acid substitutions or additions or deletions within the peptide sequence. In a particular embodiment the VP1 peptide consists of amino acids 32-45 of VP4 or a variant having 1 or two or three or four amino acid additions or deletions or substitutions. VP1 peptides include for example amino acids [5-35] to 45, [6-35] to 46, [7-35] to 47, [8-35] to 48, [9-35] to 49 and similarly 32 to [45-72], 33 to [45-73], 34 to [45-74], 35 to [45-75] and 36 to [45-76] wherein the numbers in square brackets include all numbers in the specified range individually. Such peptides can be combined in an immunogenic composition described herein. Such peptides of picornaviruses in general, or of viruses in the genus of enteroviruses, and of rhinoviruses in particular, are a feature of the present invention individually and in combination as first and second peptides.

In one embodiment the picornavirus peptide or peptides are coupled to a carrier protein such as CRM197. Suitable carrier proteins include CRM197, protein D derived from non-typeable *Haemophilus* influenza, PhtD, PhtDE, adenylate cyclase, tetanus toxoid (TT), tetanus toxoid fragment C, non-toxic mutants of tetanus toxin, diphtheria toxoid (DT), Pneumolysin (Ply), exotoxin A (ExoA) and nanoparticles such as synthetic nanoparticles. Other suitable carrier proteins include the picornavirus e.g. HRV non-structural proteins such as viral protease, polymerase and other proteins involved in replication of the picornavirus or other viruses. Favourably the carrier protein is a non-structural protein from the picornavirus such as HRV, providing an added benefit of an immune response against the non-structural protein. The first and second peptides in the immunogenic composition described herein may be coupled to the same or different carrier proteins which may be selected from the list above. When coupled to the same carrier protein, the peptides may be coupled separately to the same carrier protein and then the coupled peptides combined, or the peptides may be mixed together first and then coupled to the carrier protein.

In an alternative embodiment the peptide or peptides are combined with or inserted into a polypeptide to provide a chimeric polypeptide construct. In such an embodiment, the immunogenic composition comprises at least one chimeric polypeptide construct comprising a backbone polypeptide and peptide or peptides. Where two or more peptides are present, these may be in the same chimeric polypeptide construct or in separate chimeric polypeptide constructs which may have the same or a different polypeptide backbone. Favourably, the chimeric polypeptide construct forms a particle such as a virus like particle. The backbone polypeptide may be any suitable polypeptide, such as structural or non-structural polypeptides from viruses such as human papillomavirus (HPV), rhinovirus, hepatitis B, EV-71, influenza or norovirus.

In certain embodiments, the peptides are present on an exposed region of the particle by being inserted into a suitable region of the backbone polypeptide, such as a surface exposed loop, for example in the "a" loop of hepatitis B surface antigen (HBsAg), or the N terminal or C terminal region of HBsAg including at one of the termini. In certain embodiments two of the same or different HRV peptides are inserted into different sites in a single polypeptide such as the "a" loop and N terminal or C terminal region of the HBsAg polypeptide, thus providing a double peptide insertion chimeric HBsAg polypeptide particle. In a particular embodiment a VP1 peptide as described herein such as a VP1 32-45 peptide or variant thereof, is inserted in to the "a" loop of HBsAg and a VP4 peptide as described herein such as a VP4 1-16 peptide or variant thereof, is inserted into the N terminal region of the same HBsAg polypeptide, or the reverse. In a further aspect of the disclosure there is provided a chimeric polypeptide particle comprising a backbone polypeptide capable of forming a particle and at least one peptide comprising an epitope of a picornavirus structural polypeptide. The backbone polypeptide may be for example HBsAg, HPV L1 or a rhinovirus structural protein, or any other viral protein favourably one which is capable of forming a particle such as a VLP.

In a particular embodiment the particle is a chimeric HBsAg comprising a HBsAg polypeptide or fragment thereof, into which is inserted one or more picornavirus VP4 or VP1 peptides as disclosed herein. In one embodiment the chimeric HBsAg comprises two or more peptides from picornavirus structural proteins, which may be the same or different. Favourably the peptides are each capable of inducing a cross-neutralising immune response against two or more different picornaviruses, for example two or more rhinovirus serotypes. Favourably the chimeric HBsAg chimeric polypeptide forms a virus like particle. In one embodiment there is provided a chimeric HBsAg particle in which a VP4 peptide as described herein, favourably a VP4 peptide which contains an epitope of a picornavirus capable of eliciting a cross-neutralising immune response, for example a VP4 peptide comprising VP4 1-16, such as VP4 1-31, or VP1-24 or VP1-16, is fused to the HBsAg at the N terminus or in the "a" loop of HBsAg. In another embodiment there is provided a chimeric HBsAg particle in which a VP1 peptide as described herein, favourably a VP4 peptide which contains an epitope of a picornavirus capable of eliciting a cross-neutralising immune response, for example a VP1 peptide comprising VP1 32-45, is fused to the HBsAg at the N terminus or in the "a" loop of HBsAg. In another embodiment there is provide a double peptide chimera in which both VP1 and VP4 peptides as described here are inserted into the HBsAg, one at the N terminus and one at the "a" loop. In one embodiment the VP1 and VP4 peptides are from rhinovirus.

Immunogenic compositions provided herein may further comprise an adjuvant which may be for example a mineral salt such as an aluminium salt e.g. aluminium hydroxide. In a further embodiment the adjuvant comprises 3-Deacylated monophosphoryl lipid A (3D-MPL). In another embodiment the adjuvant comprises QS21.

Another aspect of this disclosure relates to nucleic acid molecules that encode a peptide or chimeric polypeptide as described above. Such nucleic acids can be present in a prokaryotic or eukaryotic expression vector. Suitable expression vectors include, for example, yeast such as *Pichia pastoris*. The recombinant nucleic acids, e.g., expression vectors can be introduced (e.g., infected, transfected or transformed) into host cells. Such host cells are also a feature of this disclosure. These host cells can be used to produce the chimeric polypeptides, e.g. by replicating the host cell under conditions suitable for the expression of the recombinant polypeptide. Optionally, the polypeptide can then be isolated and/or purified, e.g., prior to formulation in an immunogenic composition.

Any of the peptides or chimeric polypeptides disclosed herein can be used in medicine, e.g., as immunogenic compositions (such as vaccines) for the prevention or treatment of infection caused by picornavirus such as HRV. These compositions are suitable for use in methods for inducing antibodies against picornavirus such as HRV in humans by administering the immunogenic composition to a human subject. Favourably, administering the immunogenic composition to the human subject elicits antibodies that prevent, ameliorate or treat picornavirus infection or disease, such as HRV infection or disease.

Thus, the present disclosure also provides immunogenic compositions for use in the prevention, amelioration or treatment of picornavirus infection or disease. Such immunogenic compositions include a chimeric polypeptide comprising one or more picornavirus peptides as described herein, which chimeric polypeptide may be in the form of a particle or VLP as described above, in combination with a pharmaceutically acceptable excipient, diluent or carrier. In some embodiments, the immunogenic composition also includes an adjuvant. Suitable adjuvants include an aluminium salt, such as aluminium hydroxide, 3D-MPL and QS21. Suitable combinations of adjuvants include aluminium hydroxide and 3D-MPL; and 3D-MPL and QS21 optionally formulated with liposomes.

Terms

In order to facilitate review of the various embodiments of this disclosure, the following explanations of terms are provided. Additional terms and explanations can be provided in the context of this disclosure.

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof.

A "polypeptide" is a polymer in which the monomers are amino acid residues which are joined together through amide bonds. A "peptide" is a short amino acid sequence e.g., approximately 10-50 or 10-40 amino acids in length. The terms "polypeptide" or "protein" or "peptide" as used herein are intended to encompass any amino acid sequence and include modified sequences such as glycoproteins. The terms "polypeptide" and "peptide" are specifically intended to cover naturally occurring proteins, as well as those which are recombinantly or synthetically produced. The term "fragment," in reference to a polypeptide, refers to a portion (that is, a subsequence) of a polypeptide. The term "immunogenic fragment" refers to all fragments of a polypeptide that retain at least one predominant immunogenic epitope of the full-length reference protein or polypeptide. Orientation within the picornavirus structural proteins and exemplary peptides is recited in an N-terminal to C-terminal direction, defined by the orientation of the amino and carboxy moieties of individual amino acids. Polypeptides and peptides are translated from the N or amino-terminus towards the C or carboxy-terminus.

"Structural proteins" of a virus such as a picornavirus are proteins which are components of the mature assembled virus particle and may include nucleocapsid core protein, enzymes packaged within the virus particle and membrane proteins. Structural proteins of picornaviruses such as HRV include VP1, VP2, VP3, VP4. Structural proteins do not include "nonstructural proteins" of the virus, which are proteins which are produced in infected cells but which are not present in the mature virus particle. The "N terminal region" of the picornavirus structural proteins refers to the N terminal half of the full length proteins, favourably a region within the N terminal half of the protein and at or close to the N terminus of the full length protein. Thus for VP4 which is only around 70 amino acids in length the N terminal region is considered to be amino acids 1 to 35 of the full length protein or a region within amino acids 1-35 at or close to the N terminus of the full length protein, amino acids 1 to 30 or 1 to 25 or 1 to 20 of the full length protein or a region within amino acids 1 to 30 or 1 to 25 or 1 to 20 at or close to the N terminus of the full length protein. For VP1 which is a longer protein of towards 300 amino acids, the N terminal region is considered to be amino acids 1-100, favourably 1-80 or 1-70 or 1-60 or 1-50 of the full length protein, or a region within the N terminal 100 or 80 or 70 or 60 or 50 amino acids and at or close to the N terminus of the protein.

The term "Picornavirus" refers to any virus in the family Picornaviridae including human and animal viruses. The term "human rhinovirus" abbreviated to HRV refers to any serotype of rhinovirus in the family Picornaviridae which is capable of infecting humans and has been identified or has yet to be identified as a rhinovirus. There are several different ways of grouping HRVs as described herein, and each grouping contains multiple virus "serotypes" or "strains" (e.g., HRV-14, HRV-8, HRV-25, etc.) categorized by genetic similarity. In the context of this disclosure the term "serotype" can be used to designate an HRV, and/or a polypeptide or peptide from a specified type of HRV.

The terms "polynucleotide" and "nucleic acid sequence" refer to a polymeric form of nucleotides at least 10 bases in length. Nucleotides can be ribonucleotides, deoxyribonucleotides, or modified forms of either nucleotide. The term includes single and double forms of DNA. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. In one embodiment, a polynucleotide encodes a polypeptide. The 5' and 3' direction of a nucleic acid is defined by reference to the connectivity of individual nucleotide units, and designated in accordance with the carbon positions of the deoxyribose (or ribose) sugar ring. The informational (coding) content of a polynucleotide sequence is read in a 5' to 3' direction.

The term "carrier protein" refers to any protein to which the peptide is coupled or attached or conjugated, typically for the purpose of enhancing or facilitating detection of the antigen by the immune system. The term is intended to cover both small peptides and large polypeptides (>10 kDa). The carrier protein may comprise one or more T-helper epitopes. The peptide may be coupled to the carrier protein by any means such as chemical conjugation.

The term "virus like particle" (VLP) refers to a viral capsid which resembles the external protein structure of the native virus but is non-infectious because it does not contain viral genetic material. The expression of viral structural proteins, known as envelope or capsid or surface proteins, can result in the self-assembly of VLPs. VLPs can be enveloped or non enveloped. VLPs generally have an icosahedral structure composed of repeated identical protein subunits known as capsomeres. Capsomeres self assemble to form VLPs. "Particles" of chimeric polypeptide constructs are structures such as amorphous aggregates, or more ordered structures, e.g. a capsomere (capsomer) or a virus like particle (VLP) or small non VLP structures. Particles, including VLPs, capsomeres and less ordered structures include Hepatitis B virus HBsAg particles composed of the small HBV surface antigen, HPV particles composed of the L1 or L1 and L2 protein of HPV, HRV particles composed of the VP1, VP2, VP3 and VP4 or VP1, VP2 and VP3 of HRV, and particles from other viruses such as influenza or norovirus or enterovirus e.g. EV-71. More recently, particles including VLPs have been produced from components of a wide variety of virus families including Parvoviridae (e.g. adeno-associated virus), Retroviridae (e.g. HIV), and Flaviviridae (e.g. Hepatitis C virus). VLPs from EV71 are described in Cheng-Yu Chung et al 2010. VLPs can be produced in a variety of cell culture systems including mammalian cell lines, insect cell lines, yeast, plant cells and *E. coli.*

The term "heterologous" with respect to a nucleic acid, a polypeptide or another cellular component, indicates that the component occurs where it is not normally found in nature and/or that it originates from a different source or species.

The terms "native" and "naturally occurring" refer to an element, such as a protein, polypeptide or nucleic acid, that is present in the same state as it is in nature. That is, the element has not been modified artificially. It will be understood, that in the context of this disclosure, there are numerous native/naturally occurring serotypes of HRV (and HRV proteins and polypeptides), e.g., obtained from different naturally occurring serotypes of HRV.

A "variant" when referring to a nucleic acid or a polypeptide (e.g., a picornavirus VP1 or VP4 nucleic acid or polypeptide) is a nucleic acid or a polypeptide that differs from a reference nucleic acid or polypeptide. Usually, the difference(s) between the variant and the reference nucleic acid or polypeptide constitute a proportionally small number of differences as compared to the referent. A variant nucleic acid can differ from the reference nucleic acid to which it is compared by the addition, deletion or substitution of one or more nucleotides, or by the substitution of an artificial nucleotide analogue. Similarly, a variant peptide or polypeptide can differ from the reference polypeptide to which it is compared by the addition, deletion or substitution of one or more amino acids, or by the substitution of an amino acid analogue. Variants of the VP1 and VP4 peptides are further and more specifically described herein.

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule). A “neutralising epitope” is one which is capable of eliciting a neutralising immune response.

An “adjuvant” is an agent that enhances the production of an immune response in a non-specific manner. Common adjuvants include suspensions of minerals (alum, aluminium hydroxide, aluminium phosphate) onto which antigen is adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

An “immunogenic composition” is a composition of matter suitable for administration to a human or animal subject (e.g., in an experimental setting) that is capable of eliciting or inducing a specific immune response, e.g., against a pathogen, such as a picornavirus. As such, an immunogenic composition includes one or more antigens (for example, polypeptide antigens) or antigenic epitopes. An immunogenic composition can also include one or more additional components capable of eliciting or inducing or enhancing an immune response, such as an excipient, carrier, and/or adjuvant. In certain instances, immunogenic compositions are administered to elicit or induce an immune response that protects the subject against symptoms or conditions induced by a pathogen. In some cases, symptoms or disease caused by a pathogen is prevented (or reduced or ameliorated) by inhibiting replication of the pathogen (e.g., picornavirus) following exposure of the subject to the pathogen. In the context of this disclosure, the term immunogenic composition will be understood to encompass compositions that are intended for administration to a subject or population of subjects for the purpose of eliciting or inducing a protective or palliative immune response against picornaviruses e.g. HRV (that is, vaccine compositions or vaccines).

An “immune response” is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an “antigen-specific response”). If the antigen is derived from a pathogen, the antigen-specific response is a “pathogen-specific response.” A “protective immune response” is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo. An immune response is a cross-neutralising immune response when it is elicited by an antigen from one picornavirus serotype and neutralises not only virus from that serotype but also virus from a different picornavirus serotype. Thus for example an HRV peptide from one HRV serotype may elicit a cross-neutralising immune response against another HRV serotype. Or a peptide from one picornavirus may elicit a cross-neutralising response against another picornavirus. Cross-neutralisation can thus be between viruses or between serotypes or strains of the same virus. A cross-neutralising immune response against two or more viruses or serotypes includes the immune response against the virus from which the antigen is derived and an immune response against one further virus or serotype. A cross-neutralising immune response may include the generation of neutralising antibodies which can be measured by a suitable neutralisation assay using virus or pseudovirus to assess neutralisation capability of the antibodies.

Peptides of picornaviruses described herein may be referred to as cross-reactive or cross-neutralising or cross-protective. Cross-reactive peptides are peptides which are capable of eliciting an immune response against additional viruses or serotypes to the one the peptide is derived from. Cross-neutralising peptides are peptides which are capable of eliciting a cross-neutralising immune response, that is an immune response that neutralises the virus against which the response was elicited and also another related virus e.g. the same virus but of a different serotype, or a different virus from the same family. A cross-protective peptide is one which elicits an immune response that can prevent against infection or disease caused by the virus against which the response was elicited and also against infection or disease caused by another related virus e.g. of a different serotype.

HRV Structural Proteins and Peptides

The present invention focuses on the need for a rhinovirus vaccine and is directed towards the use of rhinovirus structural proteins and peptides which can stimulate an immune response against a number of serotypes of HRV and thus provide protection against HRV infection and disease.

The rhinovirus proteins and peptides employed in the invention may be selected from any HRV serotype including for example HRV 1B, 2, 3, 8, 10, 14, 26, 29, 31, 39, 47, 61, 62, 63, 66, 77, 97, 100, or other serotypes which may be untyped or untypeable. Serotypes of particular interest include the clade A serotypes HRV 8, HRV 25 and HRV 100, the clade B serotype HRV 14, and the clade C serotype HRV_C_026. HRV A and C serotypes are associated with the highest severity of disease and therefore the presence of the combination of a HRV A and an HRV C serotype sequence in any composition described herein is specifically contemplated.

Several 3-dimensional (3D) structures of HRV capsids are available. For HRV 14 for example, a very detailed analysis has been published by Arnold & Rossmann (1990). The capisd has a pseudo T=3 icosahedral symmetry. The surface of the virus is defined by 12 star-shaped mesas, one at each 5-fold axis of symmetry. They are surrounded by a cleft or “canyon”, 20 Ang. deep. There are also 20 triangular protrusions, one at each 3-fold axis of symmetry. The 3D structures of HRV 1A, HRV 2, HRV 3 and HRV 16 have also been determined, sometimes in complex with receptors or antibody fragments.

HRV 14 capsid dynamics has been shown to resemble “breathing” (Lewis et al 1998). The capsid structure seems to oscillate between two different structural states, one observed in 3D structures with VP4 deeply buried and the other where the N terminus of VP4 and VP1 are accessible to proteases. This has been shown also by the accessibility of different capisd fragments over time by proteolysis and mass spectroscopy (Lewis et al 1998). This “breathing” can be halted by antiviral compounds binding in a pocket behind the canyon of the capsid.

Katpally et al (2009) showed that antibodies raised against a consensus sequence of the most likely first 24 residues from rhinovirus VP4 can cross-neutralise HRV 14 and 16, and that a peptide corresponding to the first 30 amino acids of HRV 14 VP4 generated antiserum that neutralised HRV 16 and HRV 29. However, the inventors have now found that in fact a shorter peptide is more effective.

Thus the invention provides a VP4 peptide which is no more than 20 amino acids starting from the N terminus of VP4, in particular amino acids 1-16 of VP4 and variants thereof.

Miao et al (2009) have shown that a conserved peptide from the N terminus of other enteroviruses, specifically Polio 1 and Cox B3, is recognised by monoclonal antibodies (MAbs) generated against full length VP1 proteins of different enterovirus species.

An equivalent conserved peptide from HRV VP1 is also able to generate a cross-neutralising antibody response against different HRV serotypes. The HRV VP1 peptide comes from the N terminal region of VP1, in particular amino acids 32-45 of VP1 and variants thereof. By sequence alignment of VP1 and VP4 of all picornaviruses, it has also been surprisingly discovered that there are similar peptides to HVR14 VP4 1-16 and HVR14 32-45. Thus picornaviruses other than rhinovirus also have potentially cross-neutralizing peptides equivalent to HVR14 VP4 1-16 and HVR14 32-45. These picornavirus peptides are a further aspect of the invention described herein.

Throughout the specification the VP1 and VP4 sequences of HRV 14 are used as the reference sequences to determine the region from which the VP1 and VP4 peptide sequences are derived (Palmenberg et al 2010).

The selected rhinovirus peptides are capable of inducing a cross-neutralising immune response against HRV. This means that when properly presented, the peptides generate an immune response for example an antibody response, against more than one HRV serotype. Thus for example the immune response generated neutralises the HRV serotype from which the peptide originates and at least one other HRV serotype. For instance, the cross-neutralising response may neutralise more than 2 or more than 5 or more than 10 different HRV serotypes. In one embodiment the cross-neutralising response neutralises more that 2 or more than 5 or more than 10 different HPV serotypes selected from HRV 1B, 2, 3, 8, 10, 14, 26, 29, 31, 39, 47, 61, 62, 63, 66, 77, 97, 100.

Suitably the HRV peptide is selected which shows a high level of sequence identity ("homology") between HRV serotypes that is greater than 80% between two (or more) serotypes. In some cases, the HRV peptide has greater than 85% sequence identity between serotypes, or greater than 90% sequence identity between serotypes, or greater than 95% sequence identity between serotypes. Sequence identity can also be assessed by looking at the number of amino acid differences, thus for example the HRV peptide may be selected which shows only one or only two amino acid differences, or only one or only two conservative amino acid differences, or no amino acid differences between two or more serotypes across the length of the peptide. In certain embodiments, the HRV peptide is selected to have 100% sequence identity between at least two HRV serotypes i.e. there are no amino acid differences. Such HRV peptides may be referred to herein as VP4 or VP1 "consensus" sequences.

The HRV VP4 peptide 1-16 described herein from HRV 14 has 100% sequence identity within clade B for currently known clade B serotypes. The HRV VP4 peptide described herein from HRV 100(A-M) has 100% sequence identity within clade A for currently known clade A serotypes.

In a particular embodiment, the HRV peptide is a clade A consensus sequence that is identical (i.e., has 100% sequence identity) between 2 or more HRV serotypes selected from the HRV serotypes listed in FIG. 8 or FIG. 11. In another embodiment, the HRV peptide is a clade B consensus sequence that is identical between 2 or more HRV serotypes selected from the HRV serotypes listed in FIG. 9 or FIG. 12. For example, in a specific exemplary embodiment, the consensus sequence is identical between two or more clade A or clade B serotypes shown in FIGS. 8 and 11, at amino acids 32-45 of VP1, or between two or more clade A or clade B serotypes shown in FIGS. 9 and 12, at amino acids 1-16 of VP4.

Numbering starts at amino acid 1 at the N terminus, with the N terminus at the left hand end of any sequences appearing herein and the C terminus at the right. It will be evident that there may be some variability around the peptides. Thus for example peptides may be one or two or three or four amino acids longer or shorter at either end compared to the specific peptide sequences given. Thus for example, where a VP4 peptide 1-16 is employed, it may be possible to use peptide 1-14 or 1-15 or 1-17 or 1-18, or 2-14 or 2-15 or 2-16 or 2-17 or 2-18 for example, or an equivalent peptide with one or two conservative amino acid substitutions, or one or two amino acid deletions, without altering the immunological properties of the peptide or without removing the epitope. A VP4 peptide as described herein may start for example at amino acid 1, 2, 3 or 4 and end for example at amino acid 14, 15, 16, 17, 18, 19 or 20. Similarly for VP1 peptide 32-45, it may be possible to use a longer peptide containing amino acids 32-45, such as 32-43 or 32-44 or 32-46 or 32-47, or 30-45 or 31-45 or 33-45 or 34-44, or an equivalent peptide with one or two conservative amino acid substitutions, or one or two amino acid deletions, without altering the immunological properties of the peptide or without removing the epitope. A VP1 peptide as described herein may start for example at amino acid 28, 29, 39, 31, 32, 33, 34, 35, 36, 37, 38, 39 or 40 and end for example at amino acid 40, 41, 42, 43, 44, 45, 46, 47, 48, 49 or 50, using number as for HRV14. It will be understood that such variability is within the scope of the peptides described herein and that the specific peptides described herein are given by way of example and are not limiting as to the peptides that are capable of providing a cross-neutralising immune response as described herein Cross-reactive HRV VP4 and VP1 peptides which are capable of eliciting an immune response against further HRV serotypes can be identified according to the present disclosure. As shown herein, HRV sequences from different HRV serotypes can be aligned to identify regions with high similarity between HRV serotypes. Numerous sequence programs are available to perform such alignments and identify where there is sequence homology. This can enable selection of HRV VP4 and VP1 peptides which are most similar among HRV serotypes of interest and are therefore potentially cross-reactive between some or all of those HRV serotypes.

Suitably the HRV VP4 or VP1 peptide or peptides are cross-reactive peptides, so that they are able to elicit an immune response which recognises not only the VP4 or VP1 of the HRV serotype from which the VP4 or VP1 peptide is derived, but also a VP4 or VP1 peptide or protein from an HRV serotype other than the one from which it is derived. Suitably the peptide is cross-reactive with 1 or 2 or more other serotypes, within the same or a different clade. Suitably the HRV VP4 or VP1 peptide or peptides used in the invention are capable of generating a cross-neutralising immune response, that is an immune response which is capable of neutralising HRV of a different HRV serotype than the HRV serotype from which the VP4 or VP1 peptide is derived, within the same or a different clade. Cross-neutralisation can be tested for by using assays known in the art such as the assay described in Katpally et al (2009) or Phillips et al (2011), or the assay described herein in Example 1 which is adapted from these published assays.

Suitably, the VP4 or VP1 peptide is able to provide cross-protection, and suitably comprises a cross-neutralising epitope.

Cross-protection suitably occurs when a VP4 or VP1 peptide is capable of generating a protective immune response against infection/disease caused by at least two HRV serotypes. Cross-protection can occur when a consensus VP4 or VP1 peptide is selected and presented in the context of a carrier protein such as CRM197, or as a chimeric construct in which the peptide is inserted into a polypeptide for example a HBsAg or HPV or HRV polypeptide which forms a particle such as a virus like particle.

Cross-protection can be assessed by comparing incidence of infection and/or disease for a group of HRV serotypes in individuals vaccinated with a given HRV VP4 or VP1 peptide or combination thereof compared to a non-vaccinated group. Complete cross-protection against a serotype, or group of serotypes, is not required according to the present disclosure; indeed, any level of cross-protection provides a benefit. Suitably the level of cross-protection observed is such that the vaccinated group has 5% less infection and/or disease associated with a non-vaccine HRV serotype or serotypes, than a comparable non vaccinated group, more suitably up to 10%, up to 15%, up to 20%, up to 25%, up to 30%, up to 35%, up to 40%, up to 45%, up to 50%, up to 55%, up to 60%, up to 65% up to 70%, up to 80%, up to 90% or even up to 100% less infection and/or disease.

HRV VP1 and VP4 peptides and constructs containing them can be tested for immunogenicity, cross-reactivity and cross-neutralisation by standard techniques well known in the art. For example, the peptides may be injected into animal models or humans and measurement of antibody and/or cellular immune responses can be carried out for example by ELISA or cytokine analysis/measurement respectively. Methods for screening antibodies are well known in the art. An ELISA can be used to assess cross-reactivity of antibodies. Antibodies can be tested for neutralisation and cross-neutralisation properties using an assay such as described herein in Example 1.

Cross-protection against different HRV serotypes different to the one from which the VP4 or VP1 peptide is derived, can be identified using an animal model, for example mouse models (Bartlett et at 2008).

Picornavirus peptides such as the rhinovirus VP1 and VP4 peptides herein can be chemically synthesised by standard techniques, or produced recombinantly. The peptides can be in the form of individual peptides or concatamers of peptides attached in a series of for example 2 or 3 or 4 or 5 or 6 or 7 or 8 or 9 or 10 or more peptides.

Carrier Proteins for Picornavirus Peptides

Picornavirus peptides disclosed herein, such as HRV peptides, may be coupled to a carrier protein. Coupling may be by any suitable means, for example by expression as a construct with the carrier protein, or by chemical coupling or conjugation of the peptide to the carrier protein using a chemical conjugation step. Carrier proteins include CRM197 which is well known. Carrier proteins also include KLH which can be used in an immunogenic composition for animal but not human use.

CRM197 is a non-toxic form of the diphtheria toxin but is immunologically indistinguishable from the diphtheria toxin. CRM197 is produced by *C. diphtheriae* infected by the nontoxigenic phase β197tox—created by nitrosoguanidine mutagenesis of the toxigenic carynephage b (Uchida et al Nature New Biology (1971) 233; 8-11). The CRM197 protein has the same molecular weight as the diphtheria toxin but differs from it by a single base change in the structural gene. This leads to a glycine to glutamine change of amino acid at position 52 which makes fragment A unable to bind NAD and therefore non-toxic (Pappenheimer 1977, Ann Rev, Biochem. 46; 69-94, Rappuoli Applied and Environmental Microbiology September 1983 p 560-564).

Conjugation of peptides to a protein carrier can be carried out by a number of different well-known chemistries. Examples of known chemistries include conjugation of amino groups between the peptide and carrier by amino reactive reagents such as glutaraldehyde or bis-succinimidyl ester reagent (DSG—disuccinimidyl glutarate or DSS—disuccinimidyl suberate (Greg T. Hermanson. Bioconjugate techniques. Academic Press. 1996, 218-220 and 194-196); or condensing carboxyl groups and amino groups with carbodiimide reagents (Greg T. Hermanson. Bioconjugate techniques. Academic Press. 1996, 171-173). It is also possible to use a thio-ether linkage to conjugate peptides to protein carriers. This can be achieved for example by adding a moiety with a terminal thiol group onto the peptide, for example by adding a cysteine, and then reacting the reactive thiol group with a maleimide-derivatised protein carrier (see Greg T. Hermanson. Bioconjugate techniques. Academic Press. 1996). An alternative method is to couple a thiolated carrier with a sulphydryl group on the peptide to form a disulphide bridge. Peptides can also be synthesized with an additional haloalkyl group such as iodoalkyl or bromoalkyl group. Suitably the bromoalkyl group is a bromoacetyl group. Use of bromoacetyl groups to link peptides to carriers is described in the literature (Ivanov et al., 1995, Bioconjugate chemistry, 6, 269-277).

Reductive amination can also be used to conjugate an aldehyde-containing molecule with an amine-containing molecule. Peptides can also be synthesized with an additional hydrazide group. Aldehyde-containing macromolecules can also react spontaneously with hydrazide compounds to form hydrazone linkages. Hydrazides are stronger nucleophiles and react more readily with aldehydes than do primary amines. The hydrazone bond is a form of Schiff base that is more stable than the one formed from the interaction of an aldehyde and an amine. Thus a specific conjugation can be obtained by reductive amination using peptides having an additional hydrazide (Shannessy D. J. and Wilcheck. 1990. Analytical Biochemistry 191: 1-8).

In one embodiment the peptides are coupled to CRM197 according to well known conjugation chemistry techniques, for example see Mattson et al, Mol Biol Reports, 17, 167-183, 1993. In one embodiment CRM197 is purified from *Corynebacterium* and Fermentation of CRM197 is performed as described in WO 2006/100108. In one embodiment the purification process involves three chromatographic steps (Q-sepharose-XL, hydroxyapatite type I and Octyl-Sepharose) and one ultrafiltration step. Maleimide chemistry can be used to conjugate peptides having a cysteine at the N or C-terminal, Chimeric Polypeptides Comprising Picornavirus Peptides As an alternative way of presenting the picornavirus peptides, they may be in a chimeric polypeptide construct. Favourably the chimeric polypeptide construct forms particles such as capsomers or virus like particles (VLPs) or small non VLP like structures.

In a further embodiment of the invention there is provided a chimeric polypeptide construct comprising a polypeptide which forms particles and a peptide comprising an epitope of a picornavirus structural polypeptide such as a rhinovirus structural peptide for example from VP1 or VP4. The particles can be capsomers or VLPs or small non VLP like structures.

One example of a polypeptide which may be used in a chimeric polypeptide construct with a picornavirus peptide such as an HRV peptide or peptides, is a hepatitis B surface antigen polypeptide. HBsAg has been used since the 1980s as the basis for hepatitis B vaccine. HBsAg is also employed in a candidate malaria vaccine known as RTS,S, which comprises chimeric polypeptides of HbsAg chimeric polypeptides having a stretch of 226 amino acids of the S protein of hepatitis B virus (adw serotype) fused via its N terminal end to a fragment of the *P. falciparum* circumsporozoite protein (CSP), via four amino acids, Pro Val Thr Asn, representing the four carboxy terminal residues of the hepatitis B virus (adw serotype) preS2 protein. RTS,S is described in WO 93/10152. The chimeric polypeptide is expressed in a yeast strain which already carries in its genome several copies of a hepatitis B surface antigen expression cassette. The resulting strain synthesizes two polypeptides, S and RTS, that spontaneously co-assemble into mixed (RTS, S) lipoprotein particles, which present the CSP sequences at their surface.

Favourably the picornavirus peptide/HBsAg polypeptide chimera forms a particle which resembles an HBsAg particle. In a particular embodiment the S antigen polypeptide is a contiguous sequence of 226 amino acids, specifying the S protein of hepatitis B virus (adw serotype). The chimeric picornavirus peptide/HBsAg polypeptide chimera is favourably constructed so as to spontaneously form particles. The particles may be mixed particles comprising non-chimeric HBsAg polypeptide together with chimeric picornavirus peptide/HBsAg polypeptide. Suitable sites for insertion of the picornavirus peptides such as HRV peptide or peptides include the “a” loop, the N terminus and the C terminus of the HBsAg. Peptides which may be included in a chimeric HBsAg include any of the peptides described herein, including the VP4 peptides such as 1-16 and VP1 peptides such as 32-45 and variations of either or both of these, and other peptides from structural proteins of picornavirus including VP4 and VP1, such as peptides of rhinovirus VP4 and VP1. In a particular embodiment the peptide in the chimeric polypeptide construct contains a neutralising epitope. HRV peptides containing a neutralising epitope can be found in the literature and include 1-31 of VP4 (Katpally et al 2009) and 147-162 of HRV14 VP1 (Edlmayr et al 2011).

In the case of HPV virus like particles, these are suitably HPV 16 or HPV 18 virus like particles. The L1 protein of HPV self assembles into virus like particles that typically resemble HPV viruses under the electron microscope. Typically they are made up of 72 capsomeres which in turn are made up of 5 L1 polypeptides in a pentameric unit. Suitably the L1 protein is a truncated L1 protein capable of self-assembly e.g. into capsomeres or VLPs. Suitably the L1 is truncated to remove a nuclear localisation signal. Suitably the truncation is a C-terminal truncation. Suitably the C-terminal truncation removes fewer than 50 amino acids, for example fewer than 40 amino acids. In one particular embodiment the C terminal truncation removes 34 amino acids from HPV 16 and 35 amino acids from HPV 18.

The location of the picornavirus/HRV peptide or peptides in a chimeric HPV L1 polypeptide disclosed herein is important. One location for the picornavirus peptide is in one of the exposed loops or the C terminus invading arm of the L1 protein. The loops and invading arm are found when the L1 is in the form of capsomers or virus like particles (Chen et al 2000).

In any embodiment disclosed herein the HRV peptide can be located at a position selected from the following regions of the L1 sequence, where the locations relate to the HPV 16 and HPV 18 L1 reference sequence, or at an equivalent position in another HPV L1 sequence:

(i) BC loop in amino acids 50-61

(ii) DE loop in amino acids 132-142, for example amino acids 132-141, particularly amino acids 137-138

(iii) EF loop in amino acids 172-182, for example 176-182, particularly 176-179

(iv) FG loop in amino acids 271-290, for example 272-275, particularly 272-273

(v) HI loop in amino acids 345-359, for example 347-350, particularly 349-350

(vi) C terminus arm in amino acids 429-445, for example 423-440, particularly 423-424, 431-433, or 437-438 for HPV 16, and 424-425, 432-433 or 439-440 for HPV 18.

In any embodiment disclosed herein the picornavirus peptide can be inserted into the polypeptide sequence without removing amino acids from the polypeptide. Alternatively the picornavirus peptide can be inserted into the polypeptide sequence with removal of one or more amino acids from the polypeptide sequence at the position of insertion, for example 1, 2, 3, 4, 5, 6, 7, 8, 9, 10, 11, 12, 13, 14, 15, 16, 17, 18, 19 or 20 amino acids of the polypeptide sequence can be removed at the location where the peptide is inserted. Thus the picornavirus peptide can substitute for one or more amino acids in the polypeptide sequence, for example the picornavirus peptide can replace a polypeptide sequence of equivalent length to the picornavirus peptide sequence.

Where two or more picornavirus peptides are present in a chimeric picornavirus peptide/polypeptide construct, these can be different picornavirus peptides from the same picornavirus, or they can be peptides from the same picornavirus but different serotypes in which case they can be from the corresponding region in the different picornaviruses or from different regions in the different picornaviruses. For example where HRV peptides are present in a chimeric HRV peptide/polypeptide, these can be different HRV peptides from the same HRV serotype, or they can be peptides from different HRV serotypes in which case they can be from the corresponding region in the different HRV serotypes or from different regions of the different HRV serotypes.

In an embodiment, the picornavirus peptide, such as an HRV peptide, is inserted into a site which permits assembly of a supramolecular assembly of chimeric polypeptides, for example in polypeptide particles, such as virus like particles (VLPs), or capsomers, or small non VLP like structures. For example in the case of HPV chimeric particles, to maintain VLP structure, the picornavirus peptide is inserted into the L1 polypeptide at a site that does not interfere with the sites involved in formation of disulphide bridges that are involved in maintaining inter-capsomere interactions and thus VLP conformation. Typically, the chimeric VLPs are of a similar or identical size as compared to native VLPs, that is, in the case of HPV, the chimeric VLPs are of a similar or identical size compared to VLPs in which the L1 protein is full length or truncated, but does not contain a picornavirus peptide. The chimeric HPV VLPs can be in the range of 50 nm in diameter. In alternate embodiments small non-VLP structures of between 20-35 nm are formed.

In an embodiment comprising two or more picornavirus peptides in one polypeptide, the picornavirus peptides can be inserted in the same or different sites in the polypeptide sequence. Where the picornavirus peptides are inserted at the same site, this can be in the same loop and can be in the same hypervariable region of the same loop. It may be advantageous to have a short stretch of amino acids between the picornavirus peptides for example 1, 2, 3, 4, 5, 6, 7, 8, 9, or 10 amino acids between the picornavirus peptides.

Optionally, a spacer of one or more amino acids, such as glycine residues, can also be included at the N or C terminus of the picornavirus peptide. For example the peptides can further comprise one or two or three added spacer amino acids for example one or two or three amino acid residues added at the amino or the carboxy terminus (or between linked peptides where two or more picornavirus peptides are present). Generally the spacer will have no specific biological activity other than to join the immunogenic peptide to the polypeptide sequence, or to preserve some minimum distance or other spatial relationship between them. A spacer may be needed or helpful to retain the correct conformation of the polypeptide particle and/or an effective or improved presentation of the inserted picornavirus peptide compared to absence of a spacer.

Any of the picornavirus peptides can be modified, e.g., by the insertion (addition), deletion or substitution of one or more amino acids. For example, the HRV peptides can incorporate amino acids that differ from the HRV sequence of native (that is, naturally occurring) HRV VP4 or VP1 sequence. For example the peptides can have one or two amino acid insertions or substitutions within the sequence, or a deletion of one or two or several amino acids for example 1, 2, 3, 4, 5, 6, 7, 8 or up to 10 amino acids compared to the native sequence for example to remove the occurrence of a disulphide bond between two cysteines and/or the region in between the cysteines. In specific examples, the modifications present in the HRV peptides of the present disclosure, in relation to a native HRV sequence, are limited to 1 or 2 amino acid insertions, deletions, or substitutions, and/or deletion of up to 10 contiguous amino acids between two cysteine residues.

Where modifications to the HRV sequence are made in the peptides described herein, such modification can be limited such that a substantial proportion or at least 50% or at least 70% or at least 90% or at least 95% of the amino acids in the peptide correspond to amino acids in a native HRV VP4 or VP1 sequence.

Alternatively, or additionally, any particular HRV peptide can be a chimera of two or three or more HRV peptides as described herein. In the case of any of these modifications to the HRV sequence, the immunogenic character of the HRV sequence is maintained. That is, the epitope or epitopes of HRV within the peptide which elicits the desired immune response is maintained. The purpose of the modifications can be to improve the properties of the HRV peptide for example to improve cross-reactivity with structural proteins from other HRV serotypes.

Nucleic Acids Encoding HRV Peptides, Constructs Containing them and Methods for Producing Chimeric Polypeptides Another feature of this disclosure is nucleic acid molecules that encode any of the aforementioned peptides and the chimeric polypeptides containing the peptides of HRV structural peptides.

In certain embodiments, the recombinant nucleic acids that encode the peptides or chimeric polypeptides are codon optimized for expression in a selected prokaryotic or eukaryotic host cell.

To facilitate replication and expression, the nucleic acids that encode the peptides or chimeric polypeptides can be incorporated into a vector, such as a prokaryotic or a eukaryotic expression vector.

The peptides and chimeric polypeptides disclosed herein can be produced using well established procedures for the expression and purification of recombinant proteins. Procedures sufficient to guide one of skill in the art can be found in the following references: Sambrook et al., *Molecular Cloning: A Laboratory Manual*, Cold Spring Harbor Laboratory Press, Cold Spring Harbor, N.Y., 200; and Ausubel et al. *Short Protocols in Molecular Biology*, $4^{th}$ ed., John Wiley & Sons, Inc., 999. Additional and specific details are provided hereinbelow.

Host cells that include the peptide or chimeric polypeptide-encoding nucleic acids are, thus, also a feature of this disclosure. Favourable host cells include prokaryotic (i.e., bacterial) host cells, such as *E. coli*, as well as numerous eukaryotic host cells, including fungal (e.g., yeast, such as *Saccharomyces cerevisiae* and *Picchia pastoris*) cells, insect cells, plant cells, and mammalian cells (such as CHO and HEK293 cells). Recombinant nucleic acids that encode the peptides or chimeric polypeptides are introduced (e.g., transduced, transformed or transfected) into host cells, for example, via a vector, such as an expression vector. The vector can be a plasmid, a viral particle, a phage, a baculovirus, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Trichoplusia, Drosophila, Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein, including, e.g., Freshney (1994) *Culture of Animal Cells, a Manual of Basic Technique*, third edition, Wiley-Liss, New York and the references cited therein. In addition to Sambrook, Berger and Ausubel, details regarding cell culture can be found in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Immunogenic Compositions and Methods

Another aspect of the present disclosure concerns immunogenic compositions that contain picornavirus peptides or chimeric polypeptide constructs containing them, such as polypeptides that form particles such as VLPs or subviral particles such as capsomers. The immunogenic compositions disclosed herein typically include at least one pharmaceutically acceptable diluent, excipient or carrier and optionally an adjuvant. Pharmaceutically acceptable carriers and excipients are well known and can be selected by those of skill in the art. For example, the carrier or excipient can favorably include a buffer. Optionally, the carrier or excipient also contains at least one component that stabilizes solubility and/or stability. Examples of solubilizing/stabilizing agents include detergents, for example, laurel sarcosine and/or tween. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in *Remington's Pharmaceutical Sciences*, by E. W. Martin, Mack Publishing Co., Easton, Pa., 5th Edition (975).

Accordingly, suitable excipients and carriers can be selected by those of skill in the art to produce a formulation suitable for delivery to a subject by a selected route of administration. Suitable excipients include, without limitation: glycerol, Polyethylene glycol (PEG), Sorbitol, Trehalose, N-lauroylsarcosine sodium salt, L-proline, Non detergent sulfobetaine, Guanidine hydrochloride, Urea, Trimethylamine oxide, KCl, $Ca^{2+}$, $Mg^{2+}$, $Mn^{2+}$, $Zn^{2+}$ and other divalent cation related salts, Dithiothreitol, Dithioerytrol, and β-mercaptoethanol. Other excipients can be detergents (including: Tween80, Tween20, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide).

Optionally, the immunogenic compositions also include an adjuvant. The adjuvant is selected to be safe and well tolerated in the target population. For example in the case of an adjuvant selected for safety and efficacy in young children or infants, an adjuvant dose can be selected that is a dilution (e.g., a fractional dose) of a dose typically administered to an adult subject.

One suitable adjuvant is a non-toxic bacterial lipopolysaccharide derivative. An example of a suitable non-toxic derivative of lipid A, is monophosphoryl lipid A or more particularly 3-Deacylated monophoshoryl lipid A (3D-MPL). 3D-MPL is sold under the name MPL by GlaxoSmithKline Biologicals N.A., and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB2220211 A. Chemically it is a mixture of 3-deacylated monophosphoryl lipid A with 3, 4, 5 or 6 acylated chains. In the compositions of the present invention small particle 3D-MPL can be used. Small particle 3D-MPL has a particle size such that it can be sterile-filtered through a 0.22 μm filter. Such preparations are described in WO94/21292.

A lipopolysaccharide, such as 3D-MPL, can be used at amounts between 1 and 50 μg, per human dose of the immunogenic composition. 3D-MPL can be used at a level of about 25 μg, for example between 20-30 μg, suitably between 21-29 μg or between 22 and 28 μg or between 23 and 27 μg or between 24 and 26 μg, or 25 μg. In another embodiment, the human dose of the immunogenic composition comprises 3D-MPL at a level of about 10 μg, for example between 5 and 15 μg, suitably between 6 and 14 μg, for example between 7 and 13 μg or between 8 and 12 μg or between 9 and 11 μg, or 10 μg. In a further embodiment, the human dose of the immunogenic composition comprises 3D-MPL at a level of about 5 μg, for example between 1 and 9 μg, or between 2 and 8 μg or suitably between 3 and 7 μg or 4 and μg, or 5 μg.

In other embodiments, the lipopolysaccharide can be a β(1-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references. Nonetheless, each of these references is incorporated herein by reference. In addition to the aforementioned immunostimulants (that are similar in structure to that of LPS or MPL or 3D-MPL), acylated monosaccharide and disaccharide derivatives that are a sub-portion to the above structure of MPL are also suitable adjuvants. In other embodiments, the adjuvant is a synthetic derivative of lipid A, some of which are described as TLR-4 agonists, and include, but are not limited to: OM174 (2-deoxy-6-o-[2-deoxy-2-[(R)-3-dodecanoyloxytetradecanoylamino]-4-o-phosphono-β-D-glucopyranosyl]-2-[(R)-3-hydroxytetradecanoylamino]-α-D-glucopyranosyldihydrogenphosphate), (WO 95/14026); OM 294 DP (3S,9R)-3-[(R)-dodecanoyloxytetradecanoylamino]-4-oxo-5-aza-9(R)—[(R)-3-hydroxytetradecanoylamino]decan-1,10-diol,1,10-bis(dihydrogenophosphate) (WO 99/64301 and WO 00/0462); and OM 197 MP-Ac DP (3S—,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127).

Other TLR4 ligands which can be used are alkyl Glucosaminide phosphates (AGPs) such as those disclosed in WO 98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR4 agonists, and some are TLR4 antagonists. Both are thought to be useful as adjuvants.

Other suitable TLR-4 ligands, capable of causing a signaling response through TLR-4 (Sabroe et al, JI 2003 p 1630-5) are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, and muramyl dipeptide (MDP). In one embodiment the TLR agonist is HSP 60, 70 or 90. Other suitable TLR-4 ligands are as described in WO 2003/011223 and in WO 2003/099195, such as compound I, compound II and compound III disclosed on pages 4-5 of WO2003/011223 or on pages 3-4 of WO2003/099195 and in particular those compounds disclosed in WO2003/011223 as ER803022, ER803058, ER803732, ER804053, ER804057, ER804058, ER804059, ER804442, ER804680, and ER804764. For example, one suitable TLR-4 ligand is ER804057.

Additional TLR agonists are also useful as adjuvants. The term "TLR agonist" refers to an agent that is capable of causing a signaling response through a TLR signaling pathway, either as a direct ligand or indirectly through generation of endogenous or exogenous ligand. Such natural or synthetic TLR agonists can be used as alternative or additional adjuvants. A brief review of the role of TLRs as adjuvant receptors is provided in Kaisho & Akira, Biochimica et Biophysica Acta 1589:1-13, 2002. These potential adjuvants include, but are not limited to agonists for TLR2, TLR3, TLR7, TLR8 and TLR9. Accordingly, in one embodiment, the adjuvant and immunogenic composition further comprises an adjuvant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof.

In one embodiment of the present invention, a TLR agonist is used that is capable of causing a signaling response through TLR-1. Suitably, the TLR agonist capable of causing a signaling response through TLR-1 is selected from: Tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S)-Lys (4)-OH, trihydrochloride (Pam3Cys) LP which mimics the acetylated amino terminus of a bacterial lipoprotein and OspA LP from *Borrelia burgdorferi*. In an alternative embodiment, a TLR agonist is used that is capable of causing a signaling response through TLR-2. Suitably, the TLR agonist capable of causing a signaling response through TLR-2 is one or more of a lipoprotein, a peptidoglycan, a bacterial lipopeptide from *M tuberculosis, B burgdorferi* or *T pallidum*; peptidoglycans from species including *Staphylococcus aureus*; lipoteichoic acids, mannuronic acids, *Neisseria porins*, bacterial fimbriae, Yersina virulence factors, CMV virions, measles haemagglutinin, and zymosan from yeast.

In an alternative embodiment, a TLR agonist is used that is capable of causing a signaling response through TLR-3. Suitably, the TLR agonist capable of causing a signaling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signaling response through TLR-5. Suitably, the TLR agonist capable of causing a signaling response through TLR-5 is bacterial flagellin.

In an alternative embodiment, a TLR agonist is used that is capable of causing a signaling response through TLR-6. Suitably, the TLR agonist capable of causing a signaling response through TLR-6 is mycobacterial lipoprotein, diacylated LP, and phenol-soluble modulin. Additional TLR6 agonists are described in WO 2003/043572.

In an alternative embodiment, a TLR agonist is used that is capable of causing a signaling response through TLR-7. Suitably, the TLR agonist capable of causing a signaling response through TLR-7 is a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO 2002/085905.

In an alternative embodiment, a TLR agonist is used that is capable of causing a signaling response through TLR-8. Suitably, the TLR agonist capable of causing a signaling response through TLR-8 is a single stranded RNA (ssRNA), an imidazoquinoline molecule with anti-viral activity, for example resiquimod (R848); resiquimod is also capable of recognition by TLR-7. Other TLR-8 agonists which can be used include those described in WO 2004/071459.

In an alternative embodiment, a TLR agonist is used that is capable of causing a signaling response through TLR-9. In one embodiment, the TLR agonist capable of causing a signaling response through TLR-9 is HSP90. Alternatively, the TLR agonist capable of causing a signaling response through TLR-9 is bacterial or viral DNA, DNA containing unmethylated CpG nucleotides, in particular sequence contexts known as CpG motifs. CpG-containing oligonucleotides induce a predominantly Th1 response. Such oligonucleotides are well known and are described, for example, in WO 96/02555, WO 99/33488 and U.S. Pat. Nos. 6,008,200 and 5,856,462. Suitably, CpG nucleotides are CpG oligonucleotides. Suitable oligonucleotides for use in the immunogenic compositions of the present invention are CpG containing oligonucleotides, optionally containing two or more dinucleotide CpG motifs separated by at least three, suitably at least six or more nucleotides. A CpG motif is a Cytosine nucleotide followed by a Guanine nucleotide. The CpG oligonucleotides of the present invention are typically deoxynucleotides. In a specific embodiment the internucleotide in the oligonucleotide is phosphorodithioate, or suitably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. Nos. 5,666,153, 5,278,302 and WO 95/26204.

Other adjuvants that can be used in immunogenic compositions with picornavirus peptides or chimeric polypeptide constructs, e.g., on their own or in combination with 3D-MPL, or another adjuvant described herein, are saponins, such as QS21.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree *Quillaja Saponaria* Molina), and fractions thereof, are described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1, which are incorporated herein by reference. Other saponins which have been used in systemic vaccination studies include those derived from other plant species such as *Gypsophila* and *Saponaria* (Bomford et al., Vaccine, 10(9):572-577, 1992). QS21 is an Hplc purified non-toxic fraction derived from the bark of *Quillaja Saponaria* Molina. A method for producing QS21 is disclosed in U.S. Pat. No. 5,057,540. Non-reactogenic adjuvant formulations containing QS21 are described in WO 96/33739. The aforementioned references are incorporated by reference herein. Said immunologically active saponin, such as QS21, can be used in amounts of between 1 and 50 μg, per human dose of the immunogenic composition. Advantageously QS21 is used at a level of about 25 μg, for example between 20-30 μg, suitably between 21-29 μg or between 22-28 μg or between 23-27 μg or between 24-26 μg, or 25 μg. In another embodiment, the human dose of the immunogenic composition comprises QS21 at a level of about 10 μg, for example between 5 and 15 μg, suitably between 6-14 μg, for example between 7-13 μg or between 8-12 μg or between 9-11 μg, or 10 μg. In a further embodiment, the human dose of the immunogenic composition comprises QS21 at a level of about 5 μg, for example between 1-9 μg, or between 2-8 μg or suitably between 3-7 μg or 4-6 μg, or 5 μg. Such formulations comprising QS21 and cholesterol have been shown to be successful Th1 stimulating adjuvants when formulated together with an antigen. Thus, for example, picornavirus peptides and chimeric polypeptide constructs can favorably be employed in immunogenic compositions with an adjuvant comprising a combination of QS21 and cholesterol.

Optionally, the adjuvant can also include mineral salts such as an aluminium or calcium salts, in particular aluminium hydroxide, aluminium phosphate and calcium phosphate. For example, an adjuvant containing 3D-MPL in combination with an aluminium salt (e.g., aluminium hydroxide or "alum") is suitable for formulation in an immunogenic composition containing picornavirus peptides or a chimeric polypeptide construct for administration to a human subject.

Another class of suitable Th1 biasing adjuvants for use in formulations with picornavirus peptides and chimeric polypeptide constructs includes OMP-based immunostimulatory compositions. OMP-based immunostimulatory compositions are particularly suitable as mucosal adjuvants, e.g., for intranasal administration. OMP-based immunostimulatory compositions are a genus of preparations of outer membrane proteins (OMPs, including some porins) from Gram-negative bacteria, such as, but not limited to, *Neisseria* species (see, e.g., Lowell et al., J. Exp. Med. 167:658, 1988; Lowell et al., Science 240:800, 1988; Lynch et al., Biophys. J. 45:104, 1984; Lowell, in "New Generation Vaccines" 2nd ed., Marcel Dekker, Inc., New York, Basil, Hong Kong, page 193, 1997; U.S. Pat. No. 5,726,292; U.S. Pat. No. 4,707, 543), which are useful as a carrier or in compositions for immunogens, such as bacterial or viral antigens. Some OMP-based immunostimulatory compositions can be referred to as "Proteosomes," which are hydrophobic and safe for human use. Proteosomes have the capability to auto-assemble into vesicle or vesicle-like OMP clusters of about 20 nm to about 800 nm, and to noncovalently incorporate, coordinate, associate (e.g., electrostatically or hydrophobically), or otherwise cooperate with protein antigens (Ags), particularly antigens that have a hydrophobic moiety. Any preparation method that results in the outer membrane protein component in vesicular or vesicle-like form, including multi-molecular membranous structures or molten globular-like OMP compositions of one or more OMPs, is included within the definition of Proteosome. Proteosomes can be prepared, for example, as described in the art (see, e.g., U.S. Pat. No. 5,726,292 or U.S. Pat. No. 5,985,284). Proteosomes can also contain an endogenous lipopolysaccharide or lipooligosaccharide (LPS or LOS, respectively) originating from the bacteria used to produce the OMP porins (e.g., *Neisseria* species), which generally will be less than 2% of the total OMP preparation.

Proteosomes are composed primarily of chemically extracted outer membrane proteins (OMPs) from *Neisseria menigitidis* (mostly porins A and B as well as class 4 OMP), maintained in solution by detergent (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206). Proteosomes can be formulated with a variety of antigens such as purified or recombinant proteins derived from viral sources, including the picornavirus peptides and chimeric polypeptide constructs disclosed herein, e.g., by diafiltration or traditional dialysis processes. The gradual removal of detergent allows the formation of particulate hydrophobic complexes of approximately 100-200 nm in diameter (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206).

"Proteosome: LPS or Protollin" as used herein refers to preparations of proteosomes admixed, e.g., by the exogenous addition, with at least one kind of lipo-polysaccharide to provide an OMP-LPS composition (which can function as an immunostimulatory composition). Thus, the OMP-LPS composition can be comprised of two of the basic components of Protollin, which include (1) an outer membrane protein preparation of Proteosomes (e.g., Projuvant) prepared from Gram-negative bacteria, such as *Neisseria meningitidis*, and (2) a preparation of one or more liposaccharides. A lipo-oligosaccharide can be endogenous (e.g., naturally contained with the OMP Proteosome preparation), can be admixed or combined with an OMP preparation from an exogenously prepared lipo-oligosaccharide (e.g., prepared from a different culture or microorganism than the OMP preparation), or can be a combination thereof. Such exogenously added LPS can be from the same Gram-negative bacterium from which the OMP preparation was made or from a different Gram-negative bacterium. Protollin should also be understood to optionally include lipids, glycolipids, glycoproteins, small molecules, or the like, and combinations thereof. The Protollin can be prepared, for example, as described in U.S. Patent Application Publication No. 2003/0044425.

Combinations of different adjuvants, such as those mentioned hereinabove, can also be used in compositions with the picornavirus peptides and chimeric polypeptide constructs. For example, as already noted, QS21 can be formulated together with 3D-MPL. The ratio of QS21: 3D-MPL will typically be in the order of 1:10 to 10:1; such as 1:5 to 5:1, and often substantially 1:1. Typically, the ratio is in the range of 2.5:1 to 1:1 3D-MPL: QS21. Another combination adjuvant formulation includes 3D-MPL and an aluminium salt, such as aluminium hydroxide. When formulated in combination, this combination can enhance an antigen-specific Th1 immune response.

In some instances, the adjuvant formulation includes a mineral salt, such as a calcium or aluminium (alum) salt, for example calcium phosphate, aluminium phosphate or aluminium hydroxide. Where alum is present, e.g., in combination with 3D-MPL, the amount is typically between about 100 μg and 1 mg, such as from about 100 μg, or about 200 μg to about 75 μg, such as about 500 μg per dose.

In some embodiments, the adjuvant includes an oil and water emulsion, e.g., an oil-in-water emulsion. One example of an oil-in-water emulsion comprises a metabolisable oil, such as squalene, a tocol such as a tocopherol, e.g., alpha-tocopherol, and a surfactant, such as sorbitan trioleate (Span 85™) or polyoxyethylene sorbitan monooleate (Tween 80™), in an aqueous carrier. In certain embodiments, the oil-in-water emulsion does not contain any additional immunostimulants(s), (in particular it does not contain a non-toxic lipid A derivative, such as 3D-MPL, or a saponin, such as QS21). The aqueous carrier can be, for example, phosphate buffered saline. Additionally the oil-in-water emulsion can contain span 85 and/or lecithin and/or tricaprylin.

In another embodiment of the invention there is provided a vaccine composition comprising an antigen or antigen composition and an adjuvant composition comprising an oil-in-water emulsion and optionally one or more further immunostimulants, wherein said oil-in-water emulsion comprises 0.5-10 mg metabolisable oil (suitably squalene), 0.5-11 mg tocol (suitably a tocopherol, such as alpha-tocopherol) and 0.4-4 mg emulsifying agent.

In one specific embodiment, the adjuvant formulation includes 3D-MPL prepared in the form of an emulsion, such as an oil-in-water emulsion. In some cases, the emulsion has a small particle size of less than 0.2 μm in diameter, as disclosed in WO 94/21292. For example, the particles of 3D-MPL can be small enough to be sterile filtered through a 0.22 micron membrane (as described in European Patent number 0 689 454). Alternatively, the 3D-MPL can be prepared in a liposomal formulation. Optionally, the adjuvant containing 3D-MPL (or a derivative thereof) also includes an additional immunostimulatory component.

It should be noted that regardless of the adjuvant selected, the concentration in the final formulation is calculated to be safe and effective in the target population. For example, immunogenic compositions may be for eliciting an immune response against picornavirus such as HRV in human infants (e.g., infants between birth and 1 year, such as between 0 and 6 months, at the age of initial dose). Or in another example immunogenic compositions may be for eliciting an immune response against picornavirus such as HRV in elderly humans. Or the immunogenic composition may be for administration to adults or children. It will be appreciated that the choice of adjuvant can be different in these different applications, and the optimal adjuvant and concentration for each situation can be determined empirically by those of skill in the art.

Chimeric polypeptide constructs in the form of particles for use as described herein can be adsorbed on to aluminium containing adjuvants. In the case of more than one different chimeric polypeptide construct e.g. particle such as a VLP, the adjuvant can be added to the different constructs or particles or VLPs to pre-adsorb them before mixing of the different constructs or particles or VLPs to form the final immunogenic composition.

The immunogenic composition can also comprise aluminium or an aluminium compound as a stabiliser, and the present disclosure also relates to a stabilised composition wherein the chimeric polypeptide constructs such as VLPs are adsorbed onto an aluminium salt. Suitably the VLPs are more stable over time after adsorption onto an aluminium salt than in the absence of aluminium.

The immunogenic compositions described herein can be administered as vaccines by any of a variety of routes such as oral, topical, subcutaneous, musosal, intravenous, intramuscular, intranasal, sublingual, intradermal and via suppository. Intramuscular, sublingual and intradermal deliveries are preferred.

The dosage of the peptides or chimeric polypeptide constructs such as VLPs can vary with the condition, sex, age and weight of the individual and the administration route of the vaccine. The quantity can also be varied with the number of different peptides or chimeric constructs.

An immunogenic composition typically contains an immunoprotective quantity (or a fractional dose thereof) of the antigen and can be prepared by conventional techniques. Preparation of immunogenic compositions, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.
Typically, the amount of protein in each dose of the immunogenic composition is selected as an amount which induces an immunoprotective response without significant, adverse side effects in the typical subject Immunoprotective in this context does not necessarily mean completely protective against infection; it means protection against symptoms or disease, especially severe disease associated with the virus. The amount of antigen can vary depending upon which specific immunogen is employed. Generally, it is expected that each human dose will comprise 1-1000 μg of protein, Suitably each vaccine dose comprises 1-100 μg of each peptide conjugate or chimeric polypeptide construct, suitably at least 5 μg, or at least 10 μg, for example, between 5-50 μg of each peptide conjugate or chimeric polypeptide construct, most suitably 10-50 μg of each, such as 10 μg, 15 μg, 20 μg, 40 μg or 50 μg. For example there may be 10 or 15 or 20 or 30 or 40 μg of each peptide conjugate or chimeric polypeptide construct, in a dose of vaccine. The amount utilized in an immunogenic composition is selected based on the subject population (e.g., infant or elderly). An optimal amount for a particular composition can be ascertained by standard studies involving observation of antibody titres and other responses in subjects. Following an initial vaccination, subjects can receive a boost in about 4 weeks.

The immunogenic compositions described herein suitably generate an immune response in a human or animal subject against at least 2 different picornaviruses or two different serotypes of a picornavirus such as two different HRV serotypes, suitably 2 or more, 3 or more, 4 or more, 5 or more, or 10 or more different serotypes.

The HRV compositions described herein suitably provide protection against infection and/or disease from at least 2 different HRV serotypes, suitably 2 or more, 3 or more, 4 or more, 5 or more, or 10 or more different serotypes.

Furthermore, the compositions described herein which include a carrier protein or chimeric polypeptide such as a VLP, will also generate an immune response against the carrier protein or VLP itself. This may be a protective response. Thus the immunogenic compositions may provide protection against infection or disease caused by the native virus corresponding to the VLP of the immunogenic composition. For example a chimeric HBsAg particle or VLP containing one or more peptides of a picornavirus such as HRV may protect against infection or disease caused by HBsAg as well as against infection with the picornavirus. Similarly a chimeric rhinovirus non-structural protein particle or VLP containing one or more peptides of a picornavirus such as HRV may provide a further beneficial immune response against the picornavirus non-structural protein.

Optionally the HRV immunogenic composition or vaccine can also be formulated or co-administered with other antigens such as antigens from other respiratory viruses such as influenza or RSV, or other causes of COPD such as Non-typeable *Haemophilus influenzae, Moraxella catharralis* and *Streptococcus pneumoniae.*

For all vaccines described herein, the vaccine is suitably used for the vaccination of any age group, particularly for vaccination of children and elderly populations.

Suitably the vaccine is delivered in a 2 or 3 dose regimen, for example in a 0, 1 or a 0, 2 or a 0, 3 or a 0, 4 or a 0, 5 or a 0, 6 or a 0, 12 month regimen, or 0, 1, 6 or a 0, 2, 6 or a 0, 6, 12 month regimen respectively.

Suitably the vaccine is a liquid vaccine formulation, although the vaccine can be lyophilised and reconstituted prior to administration.

EXAMPLES

Example 1

Immunogenicity of Human Rhinovirus-related Peptides and Full Length Proteins Objectives In this experiment, the following were evaluated:

(1) the immunogenicity of KLH-conjugated VP1/VP4-related peptides or full length proteins and (2) the performance of HRV peptides/-Hepatitis B surface antigen chimeric polypeptide constructs.

Peptides were selected based on bioinformatics predictions and compared to published data showing an ability of various peptides to elicit (cross-) neutralizing antibodies (McCray & Werner, 1987, 1989; Katpally et al., 2009; Miao et al., 2009; Edlmayr et al., 2011). Besides peptides, concatamers of full length clade B VP4 proteins were produced and purified. These concatamers were designed, based on amino-acid sequence analysis, to cover the whole panel of existing sequences within B clade.

Specific and cross-reactivity of rabbit sera were measured using peptide-based ELISA and cross-neutralization assays.

Material and Methods

Study Design

Immunogencity of HRV-related peptides and full length proteins was investigated in four experiments, designed similarly.

Groups of NZW rabbits (N=2-3/group) were immunized intramuscularly (in the tibialis muscle) on days 0, 14, 42 and 70 with 20 to 100 μg of antigen formulated with a water in oil adjuvant (Specol, Leonards et al, 1994). Bleeding was carried out at 14 days post $2^{nd}$, $3^{rd}$ and $4^{th}$ injections. Unless stated otherwise, the humoral response was measured 14 days post $4^{th}$ injection by ELISA and neutralization assays. Table 2 below shows the peptides that were injected and also the two full length 5×VP4 concatamer constructs that were used. Chimeric polypeptide constructs of HBsAg with rhinovirus VP4 peptides were prepared as described in Example 2.

TABLE 2

| Origin | Sequence | Carrier | Dose | Study |
|---|---|---|---|---|
| | NaCl 150 mM- CONTROL | | 20-100 μg | 20110375 |
| VP1 | HRV14: 147-VVQAMYVPPGAPNPKE-162 | KLH | | |
| VP4 | HRV14: 39-SSAGQSLSMDPSKFTEPVKDLMLKGAPALN-68 | KLH | | |
| VP1 | HRV14: 1-GLGDELEEVIVEKTKQTVASISSGPKHTQK-30 | KLH | | |
| VP1 | HRV14: 32-PILTANETGATMPV-45 | KLH | | |
| VP1 | HRV8: 32-PALDAAETGHTSSV-45 | KLH | | |
| VP1 | HRV25: 32-PILDAAETGHTSNV-45 | KLH | | |
| VP1 | HRV_C_026: 32-QALGAVEIGATADV-45 | KLH | | |
| VP4 | HRV14: 1-GAQVSTQKSGSHENQN-16 | KLH | | |
| VP4 | HRV100: 1-GAQVSRQNVGTHSTQN-16 | KLH | | |
| VP4 | HRV_C_026: 1-GAQVSRQSVGSHETMI-16 | KLH | | |
| VP4 | HRV14: 1-GAQVSTQKSGSHENQNILTNGSNQTFTVINY-31 | HB-S N Term | 20 μg | 20110765 |
| VP4 | HRV14: 1-GAQVSTQKSGSHENQNILTNGSNQTFTVINY-31 | HB-S A loop | | |
| VP4 | HRV14: 1-GAQVSTQKSGSHENQNILTNGSNQTFTVINY-31 | KLH | | |
| | NaCl 150 mM- CONTROL | | | |
| VP4 | Concatemer of VP4 full length clade B (5x) (HRV14, 26, 35, 52 and CU003) (Rhi004) | | 20 μg | 20120174 |
| VP4 | Concatemer of VP4 full length HRV14 (5x) (Rhi008) | | | |
| | NaCl- CONTROL | | | |

Peptides

HRV peptides were provided by Polypeptide Laboratories. Peptides were conjugate to KLH using m-maleimidobenzoic acid N-hydroxysuccinimide ester (MBS) after addition of cysteine at the N-terminal and amidation of the C-terminal region.

Cloning, Expression and Purification of VP4 Polyprotein Clade A (Rhi002), Clade B (Rhi004), Clade C (Rhi006) and 5×HRV14 Serotype Clade B (Rhi008) Proteins Expression Plasmid and Recombinant Strain Genes encoding proteins of full length of VP4 polyproteins (Rhi002/Rhi004/Rhi006/Rhi008) and a His tag were cloned into the pET24b(+) expression vector (Novagen) using the NdeI/XhoI restriction sites using standard procedures. Final constructs were generated by the transformation of *E. coli* strain C43 (DE3) (Rhi004/Rhi006/Rhi008) or Rosetta2 (DE3) (Rhi002) with the recombinant expression vector according to standard method with $CaCl_2$-treated cells (Hanahan D. Plasmid transformation by Simanis. In Glover, D. M. (Ed), DNA cloning. IRL Press London. (1985): p. 109-135.).

Host Strain.

C43(DE3) is a derivative of C41 strain which is a derivative of BL21. Strains having the designation (DE3) are lysogenic for a λ prophage that contains an IPTG inducible T7 RNA polymerase. λ DE3 lysogens are designed for protein expression from pET vectors This strain is also deficient in the ion and ompT proteases. The C43 strains contain genetic mutations phenotypically selected for conferring tolerance to toxic proteins. This strain has at least one mutation, which prevents cell death associated with expression of many recombinant toxic proteins and selected for resistance to a different toxic protein and can express a different set of toxic proteins.

Genotype: *E. coli* C43::DE3 strain, $F^-$ ompT $hsdS_B(r_B^- m_B^-)$ gal dcm (DE3) #

Rosetta2(DE3) is a derivative of BL21 designed to enhance the expression of eukaryotic proteins that contain codons rarely used in *E. coli*. These strains supply tRNAs for 7 rare codons (AGA, AGG, AUA, CUA, GGA, CCC and CGG). Strains having the designation (DE3) are lysogenic for a λ prophage that contains an IPTG inducible T7 RNA polymerase. λ DE3 lysogens are designed for protein expression from pET vectors This strain is also deficient in the ion and ompT proteases.

Genotype: *E. coli* Rosetta2::DE3 strain, $F^-$ ompT $hsdS_B$ $(r_B^- m_B^-)$ gal dcm (DE3) pRARE2 ($Cam^R$).

Expression of the recombinant proteins.

*E. coli* transformants were stripped from agar plates and used to inoculate 200 ml of LBT broth±1% (w/v) glucose+kanamycin (50 μg/ml) to obtain O.D.600 nm between 0.1-0.2. Cultures were incubated overnight at 37° C., 250 RPM.

These overnight cultures were diluted to 1:20 in 500 ml of LBT medium containing kanamycin (50 μg/ml) and grown at 37° C. at a stirring speed of 250 rpm until O.D.620 reached 0.5/0.6.

At O.D.600 nm around 0.6, cultures were induced for recombinants protein expression by addition of 1 mM isopropyl β-D-1-thiogalactopyranoside (IPTG; EMD Chemicals Inc., catalogue number: 5815) and incubated overnight at 37° C., 250 RPM for C43 (DE3) strain (Rhi004/Rhi006/Rhi008) or 3 h at 37° C., 250 RPM for Rosetta2(DE3) strain (Rhi002).

After overnight induction (around 16 hours) or 3 h, $O.D._{600\ nm}$ was evaluated and cultures were centrifuged at 14 000 RPM for 15 minutes and pellets were frozen at −20° C. separately.

Purification of Rhi002:

The bacterial pellet was suspended in PBS (pH 7.4). Bacteria were lysed using a French Press system 3×20 000 PSI. Soluble (supernatant) and insoluble (pellet) components were separated by centrifugation at 20 000 g for 30 min at 4° C.

The 6-His tagged-protein was purified under denaturing conditions on IMAC. The insoluble components were solubilized in 50 mM Bicine buffer pH 8.0, containing 6M Guanidine, 500 mM NaCl. Solubilized component was loaded on a 5 ml GE Histrap column (GE) preequilibrated with the same buffer used for pellet solubilisation. After loading on the column, the column was washed with a 50 mM bicine buffer pH8.0, containing, 6M urea and 500 mM NaCl. Elution was performed using a 50 mM bicine buffer pH8.0, containing, 6M urea, 500 mM NaCl and imidazole (250 mM).

After gel analysis, IMAC elution containing Rhi002 fragment was dialysed against bicine buffer (25 mM Bicine, 4M urea, 500 mM NaCl, 0.1% pluronic acid—5 mM EDTA, 1% sucrose pH9.5). Dialysed fraction was loaded on SEC chromatography for further purification step.

After SEC chromatography, more pure fractions were selected for and dialysed against PBS pH7.4 containing 1% empigen.

Protein concentration was determined using Lowry RC/DC Protein Assay of BioRad. Proteins were thus pooled, sterile-filtered on 0.22 μm, stored at −80° C.

Purification of Rhi004:

The bacterial pellet was resuspended in 20 mM bicine buffer pH 8.3 containing 500 mM NaCl-benzonase and inhibitor protease cocktail without EDTA (Roche). Bacteria were lysed using a French Press system 2×20 000 PSI. Soluble (supernatant) and insoluble (pellet) components were separated by centrifugation at 20 000 g for 30 min at 4° C.

The 6-His tagged-protein was purified under native conditions on IMAC. The soluble (supernatant) components was loaded on a 5 ml GE Histrap column (GE) preequilibrated with the same buffer used to lyse cells, without benzonase and inhibitor protease cocktail without EDTA (Roche). After loading on the column, the column was washed with a 20 mM bicine buffer pH 8.3 containing 500 mM NaCl. Elution was performed using a 20 mM bicine buffer pH8.3, containing, 500 mM NaCl and imidazole (500 mM-gradient). After gel analysis, more pure fractions were selected, concentrated and loaded on SEC superdex 75 chromatography for further purification step.

After SEC chromatography in 20 mM bicine pH 8.3 containing 150 mM NaCl, 5 mM EDTA, more pure fractions were selected for further purification step. More pure fractions were pooled and loaded on SEC G25 chromatography in 20 mM bicine pH8.3 containing 500 mM NaCl.

After gel analysis, more pure fractions were selected and loaded on 5 ml GE Histrap column (GE) preequilibrated with 20 mM bicine buffer pH 8.3 containing 500 mM NaCl. After loading on the column, the column was washed with a 20 mM bicine buffer pH 8.3 containing 500 mM NaCl. Elution was performed using a 20 mM bicine buffer pH8.3, containing, 500 mM NaCl and imidazole (500 mM-gradient). After gel analysis, more pure fractions were selected, pooled and dialysed against 20 mM Bicine buffer containing 150 mM NaCl and 5 mM EDTA.

Protein concentration was determined using Lowry DC Protein Assay of BioRad. Proteins were thus pooled, sterile-filtered on 0.22 μm, stored at −80° C.

Purification of Rhi006:

The bacterial pellet was suspended in PBS (pH 7.4). Bacteria were lysed using a French Press system 1×20 000 PSI. Soluble (supernatant) and insoluble (pellet) components were separated by centrifugation at 20 000 g for 30 min at 4° C.

The 6-His tagged-protein was purified under denaturant conditions on IMAC. The insoluble components were solubilized in 50 mM Bicine buffer pH 8.0, containing 6M Guanidine, 500 mM NaCl, complete protease inhibitor cocktail without EDTA (Roche). Solubilized component was loaded on a 5 ml GE Histrap column (GE) pre-equilibrated with the same buffer used to pellet solubilisation. After loading on the column, the column was washed with a 50 mM bicine buffer pH8.0, containing, 6M urea and 500 mM NaCl. Elution was performed using a 50 mM bicine buffer pH8.0, containing, 6M urea, 500 mM NaCl and imidazole (250 mM).

After gel analysis, IMAC elution containing Rhi06 fragment was dialysed against PBS pH 8 containing 4M urea. Dialysed fraction was loaded on SEC chromatography for further purification step. After SEC chromatography more pure fractions were selected and dialysed against PBS pH8 containing 1M urea and 5 mM EDTA.

Protein concentration was determined using Lowry RC/DC Protein Assay of BioRad. Proteins were thus pooled, sterile-filtered on 0.22 μm, stored at −80° C.

Purification of Rhi008:

The bacterial pellet was resuspended in PBS (pH 7.4) containing complete protease inhibitor cocktail—EDTA-free (Roche). Bacteria were lysed using a French Press system 2×20 000 PSI. Soluble (supernatant) and insoluble (pellet) components were separated by centrifugation at 20 000 g for 30 min at 4° C.

The 6-His tagged-protein was purified under denaturant conditions on IMAC. The insoluble components were solubilized in 50 mM Bicine buffer pH 8.3, containing 8M urea, 500 mM NaCl, complete protease inhibitor cocktail without EDTA (Roche). Solubilized component was loaded on a 10 ml NiNTA resin pre-equilibrated with the same buffer used for pellet solubilisation. After loading on the column, the column was washed with a 50 mM bicine buffer pH8.3, containing, 8M urea and 500 mM NaCl. Elution was performed using a 50 mM bicine buffer pH8.0, containing, 6M urea, 500 mM NaCl and imidazole (500 mM).

After gel analysis, IMAC elution containing Rhi08 fragment was step dialysed against 25 mM bicine buffer pH8.3 containing 4Murea and 250 mM NaCl, followed by a second step dialysis against PBS pH 7.4.

Protein concentration was determined using Lowry RC/DC Protein Assay of BioRad. Proteins were thus pooled, sterile-filtered on 0.22 μm, stored at −80° C.

HRV-HBsAg Chimeric Polypeptide Constructs are Described in Example 2.

ELISA for Detection of Antibodies to Proteins or Peptides

Quantification of anti-VP1/VP4 related peptide or protein antibodies was performed by ELISA using specific peptides or concatemers of full length proteins as coating antigen. Antigens were diluted at a final concentration of 2 μg/ml in PBS and were adsorbed overnight at 4° C. to the wells of 96-wells microtiter plates (Maxisorp Immuno-plate, Nunc, Denmark). The plates were then incubated for 1 hr at 37° C. with PBS+0.1% Tween20+1% BSA (saturation buffer). Sera diluted in saturation buffer were added to the plates and incubated for 1 hr 30 min at 37° C. The plates were washed four times with PBS 0.1% Tween20 and a biotin-conjugated anti-rabbit Ig (Amersham Biosciences, UK) diluted in saturation buffer was added to each well and incubated for 1 hr 30 at 37° C. After that the plates were washed four times with PBS 0.1% Tween20, a streptavidin-horseradish peroxydase (Roche), diluted in saturation buffer was added for an additional 30 min at 37° C. Plates were washed 4 times with PBS 0.1% Tween20 again and incubated for 20 min at room temperature with a solution of 0.04% o-phenylenediamine (Sigma) 0.03% $H_2O_2$ in 0.1% Tween20, 0.05M citrate buffer pH 4.5. The reaction was stopped with 2N $H_2SO_4$ and read at 492/620 nm. ELISA titers were calculated from a reference by SoftMaxPro (using a four parameters equation) and expressed in EU/ml.

Rhinovirus Production

HRV2, 8, 10, 14, 39 and 61 strains were purchased at ATCC and amplified on Hela-H1 cells cultured in infection medium (MEM containing 2% FCS, 30 mM MgCl2, and 1 mM glutamine). To this end, 5 million Hela-H1 cells were seeded in 75 $cm^2$ plates and grown overnight at 34° C. Plates were then infected at a multiplicity of infection of 15 and further incubated until complete lysis of cell monolayers (24 h to 48 h depending on the strain). Supernatants were collected and debris was removed by centrifugation (1,000 g-10 min). Cleared supernatants were aliquoted, stored at −80° C. and titrated on Hela-H1.

Titration of Rhinovirus Production

Hela-H1 cells were seeded in 96 well plates (5,000 cells/well) and grown overnight at 34° C. with 5% $CO_2$. Plates were then infected with serial 2-fold dilutions (starting dilution=1/1000) of rhinovirus suspensions tested in octuplicates. Three to five days after infection, presence of HRV-mediated cytopathic effects was revealed by measuring cell viability. To this end, cells were incubated with the WST-1 reagent as recommended by the manufacturer (Promega). A cut-off value was then defined for each plate as the mean−3 standard deviations of optical densities (O.D.) of wells containing non-infected cells. Wells showing O.D. below this cut-off were scored as positive for CPE. Virus concentration was calculated according to the Reed and Muench formula.

Neutralization Assay

Hela-H1 cells were plated in 96-well plate (5,000 cells/well) and incubated overnight at 37° C. with 5% $CO_2$. Sera were inactivated at 56° C. during 30 min 100 $TCID_{50}$ of HRV (of the relevant serotype, depending on whether neutralization or cross-neutralization was being assayed) were put in presence of serial dilutions (2-fold dilutions starting dilution=1/2) of rabbit serum at 37° C. for 2 h. The mixture was then overlaid on cell monolayers and plates were further incubated at 37° C. for 3 to 5 days until complete lysis of control cell monolayers had occurred. Cell viability was then measured using WST-1 reagent as recommended by the manufacturer (Promega). O.D. were then converted as a percentage of cytopathic effect and the reciprocal of the dilution giving a 50% reduction of cytopathic effect (CPE) relative to control cells. CPE was then extrapolated using non-linear regression with the GraphpadPrism Software.

Results

1. Immunogenicity of Peptides—Peptide Specific Response

The peptide specific response in rabbits that received KLH or HB-S-conjugated peptides was measured 14 days post $4^{th}$ immunization using the peptide-based ELISA described herein.

Figure 3:
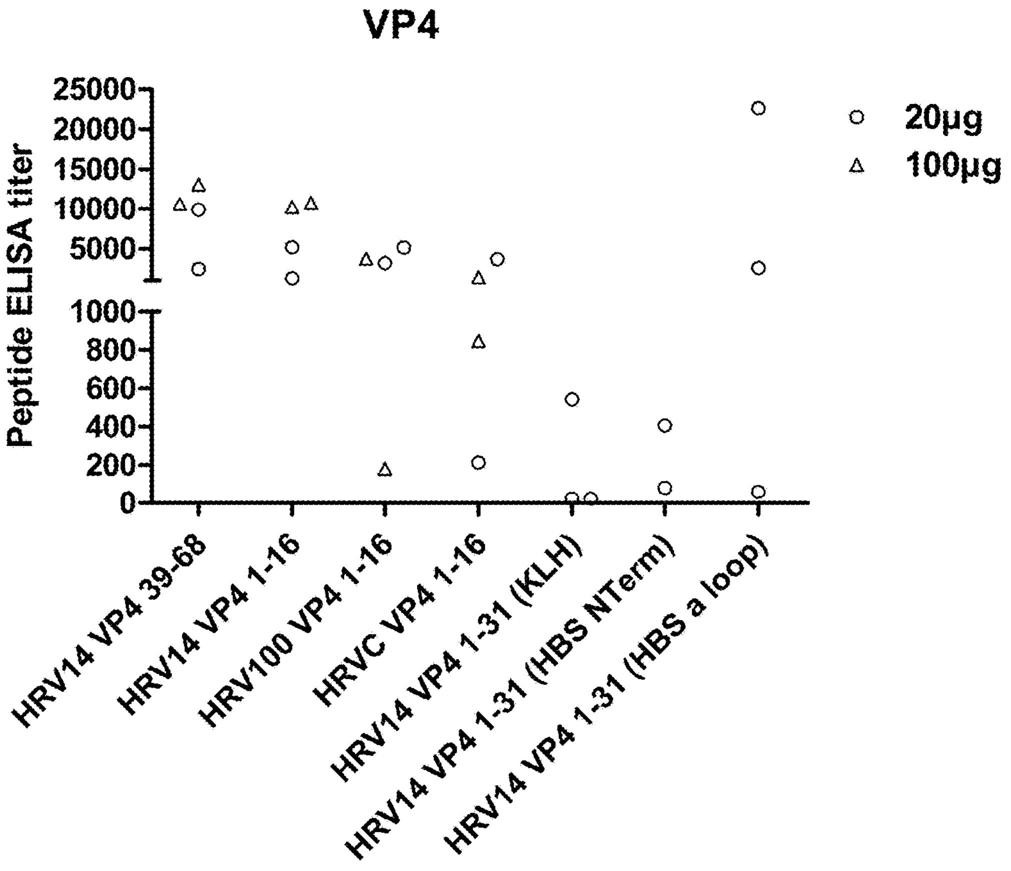
FIG. 3. shows peptide specific antibodies generated in rabbits immunised with VP4 peptides either conjugated to KLH or in hepatitis B surface antigen (HBsAg) chimeric constructs.

Results were as follows and are shown in FIGS. 2 and 3.

No response was detected in the NaCl control group.

VP1-KLH Conjugates (FIG. 2)

High levels of VP1 peptide-specific antibodies were detected in rabbits that received

HRV14 VP1 147-162,

HRV14 VP1 1-30 and

HRV14 VP1 32-45

Low levels of antibodies were elicited by

HRV8, HRV25 or HRV_C_026 VP1 32-45 peptides although increasing the antigen dose positively affected antibody titers.

VP4-KLH Conjugates (FIG. 3)

Overall, VP4-related peptides induced lower levels of antibodies than VP1 peptides. However, high titers of VP4 peptide-specific antibodies were measured in rabbits that received HRV14 VP4 39-68 or HRV14, HRV100 and HRVC VP4 1-16.

In contrast with the paper published by Katpally and colleagues (2009), the HRV14 VP4 1-31 was poorly immunogenic. However, this was possibly explained by aggregation and poor solubility of this peptide observed upon KLH conjugation.

VP4-HbsAg Chimeric Constructs (FIG. 3)

Insertion of HRV14 VP4 1-31 in the A loop but not at the N terminus of HBsAg induced high levels of peptide-specific antibodies in 2 out of 3 rabbits. Results are shown in FIG. 3.

2. Immunogenicity of Full Length Proteins—Protein Specific Response

Figure 4:
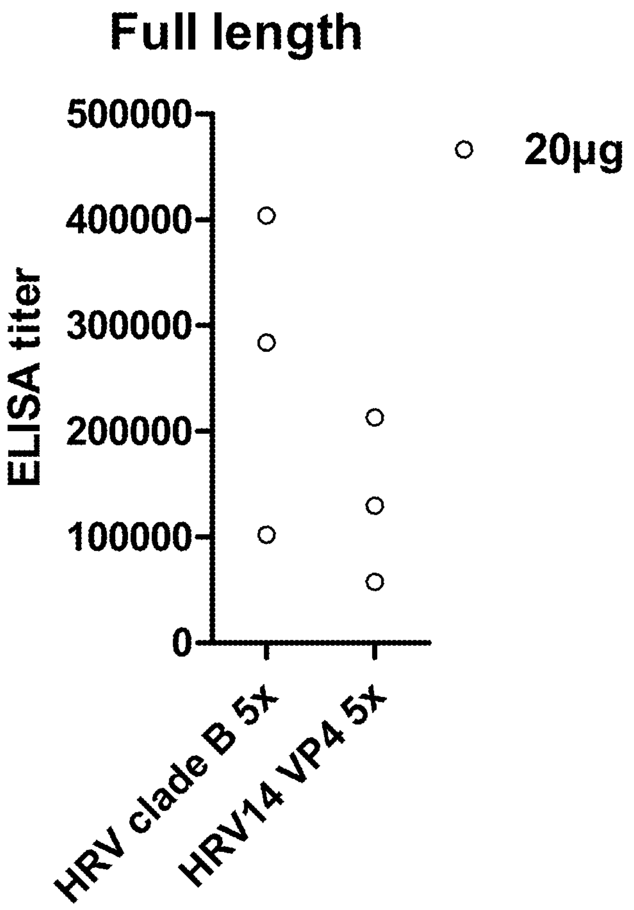
FIG. 4. shows peptide specific antibodies generated in rabbits immunised with full length VP4 in the form of a concatamer.

Immunogenicity of full length proteins in the form of concatamers was measured 14 days post 4th immunization by ELISA. Results are shown in FIG. 4.

- No response was detected in NaCl group
- High levels of VP4-directed antibodies were detected in rabbits that received the concatamers of clade B or HRV14 VP4 proteins.

3. Comparison of Neutralizing Antibody Titers Elicited by Peptides and Full Length Proteins Levels of neutralizing antibodies elicited by VP1/VP4-related peptides and proteins were measured 14 days post $4^{th}$ vaccination using a panel of HRV strains (i.e. HRV2, 8, 10, 14, 39 and 61). Results are shown in FIG. 5 and FIG. 6.

- No neutralizing antibodies were detected NaCl control group
- Specific and/or cross-neutralizing antibodies were detected in all groups that received VP1-related peptides. Importantly, the HRV14 VP1 32-45 peptide induced the broadest cross-reactivity since this particular peptide was able to neutralize all strains tested.
- Significant levels of specific and cross-neutralizing antibodies were detected in rabbits immunized with HRV14 VP4 39-68, VP4 1-16 and HRV100 VP4 1-16 peptides while inconsistent response was observed in other groups vaccinated with KLH-conjugated peptides or full length proteins. Notably, the HRV100 VP4 1-16 peptide induced the broadest cross-reactivity since this particular peptide was able to neutralize all 6 strains tested. Thus in VP4 1-16, a peptide shorter than VP4 1-31 was identified that is more conserved and is able to induce broader cross-neutralising activity.

4. Full Length VP4-Proteins Elicit Low Levels of Antibodies Specific for the 1-16 Regions.

Figure 7:
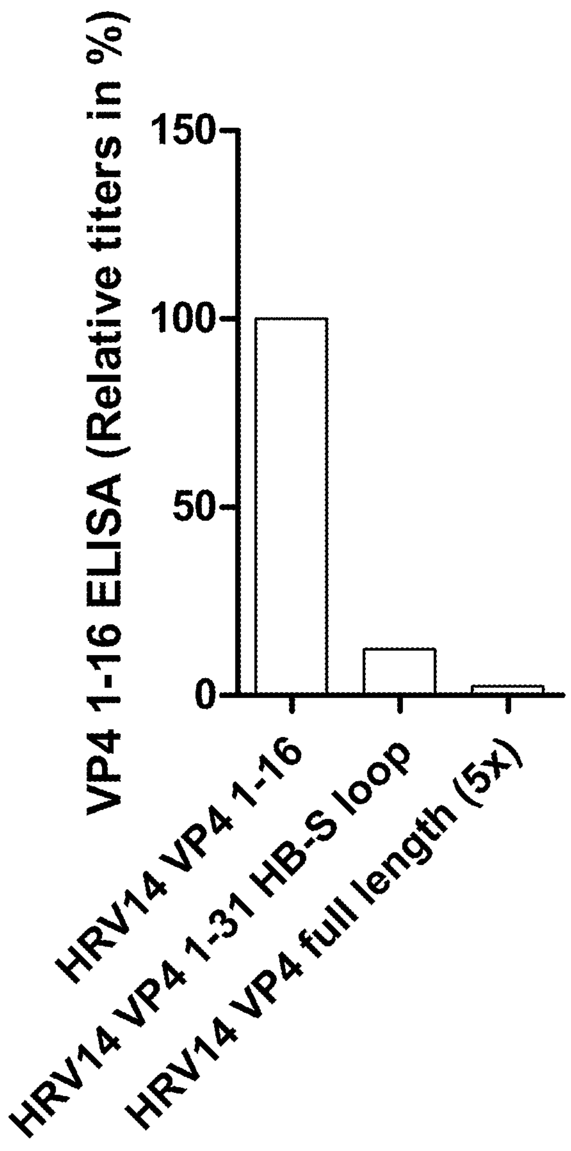
FIG. 7. shows antibodies specific for the 1-16 region of VP4 in rabbits immunised with VP4 1-31 or VP4 full length, relative to VP4 1-16.

Data collected in neutralisation assays suggested that a neutralizing epitope lies within the VP4 1-16 regions and that immunisation with longer peptide sequences (1-31) or VP4 full length protein could misdirect the immune response against non-neutralising epitopes. A similar mechanism, contributing to HRV immune escape, was described for the VP1 protein (Niespodziana et al 2012). Indeed, the major portion of antibodies were directed against the 1-30 region of VP1 after immunisation with the full-length VP1 protein, and this region is well known to elicit poorly (cross-) neutralizing antibodies (Niespodziana et al 2012) (and as observed in these experiments). It was therefore checked whether the full length protein elicited antibodies directed against the VP4 1-16 region. Rabbit sera were tested for the presence of VP4 1-16 specific antibodies by ELISA and relative (to the HRV14 VP4 1-16 vaccinated group) titers were calculated. Very low levels of VP4 1-16 antibodies were detected in rabbits that received the VP4 1-31 in HBsAg loop or the VP4 full length protein. Results are shown in FIG. 7. Overall, these results suggest that immunization with full length VP4 (or VP1) protein misdirects the immune response against non-neutralizing epitopes.

TABLE 3

Anti-HRV14 VP4 1-16 peptide antibody titers induced by HRV14 VP4 1-16 peptide, HRV14 VP4 1-31 peptide and VP4 full length protein.

| | |
|---|---|
| HRV14 VP4 1-16 | 17561.5 |
| HRV14 VP4 1-31 in HBS (a loop) | 2163 |
| 5x Full length HRV14 | 427 |
| NaCl | <25 |

5. Full Length VP4-Proteins

Rabbits: Immunogenicity of Full Length Clade A and C VP4 Proteins and HRV14 VP1 Protein In a further experiment, ELISA and neutralization assays were performed 14 days Post-IV. As shown in Table 4 below, high levels of cross-reactive anti-VP4 IgG were induced by concatemers of VP4 proteins, and to a lower extent, by the VP4-HBs chimeric construct. However, even if some neutralization of the HRV14 strain was observed, none of these constructs was able to induce antibodies that neutralize HRV39. These data confirm previous results suggesting that full length HRV VP4 proteins elicit high levels of non-neutralizing antibodies. Similarly, the HRV14 VP1 protein was highly immunogenic but failed to elicit functional antibodies.

TABLE 4

| | n° rabbit | VP4 Full clade A PIV | VP4 Full clade C PIV | VP4 full length HRV14 PIV | VP1 full length HRV14 PIV | HRV14 neutra | HRV39 neutra |
|---|---|---|---|---|---|---|---|
| VP4 Full | TA 114 | 716093 | 171617 | 133378 | | 15.17 | <2 |
| length clade | TA 115 | 474532 | 106675 | 22081 | | 11.48 | <2 |
| A concatemer | TA 116 | 755820 | 64151 | 157835 | | <2 | <2 |
| VP4 Full | TA 117 | 414859 | 992334 | 42522 | | 15.94 | <2 |
| length clade | TA 118 | 466868 | 889650 | 63881 | | 20.78 | <2 |
| C concatemer | TA 119 | 97803 | 541508 | 32296 | | <2 | <2 |
| HRV14 VP4 | TA 123 | 317 | 2217 | 69266 | | 2.542 | <2 |
| Full Length | TA 124 | 35022 | 41333 | 101670 | | 3.615 | <2 |
| (HBs) | TA 125 | 148 | 2596 | 18933 | | <2 | <2 |
| VP1 HRV14 | TA 120 | | | | 365792 | 11.5 | <2 |
| | TA 121 | | | | 597110 | <2 | <2 |
| | TA 122 | | | | 174395 | 2.542 | <2 |

CONCLUSIONS

This study demonstrates that HRV14 VP1 32-45 and HRV100 VP4 1-16 are immunogenic and elicit broadly cross-reactive antibodies. In contrast, full length VP4 proteins induced high levels of antibodies that did not prove to be functional. The data suggest that immunisation with full length VP4 proteins misdirects the immune response against non-neutralizing epitopes. This was confirmed by the fact that full length VP4 proteins did not induce antibodies directed against the VP4 1-16 region. Such a mechanism was also demonstrated for HRV14 VP1 protein and further supports the need for peptide vaccination to direct the immune response against well-conserved, cross-neutralizing antibodies.

Example 2

Construction of *Pichia pastoris* Strain Expressing VP4-S,S Mixed Particles

Introduction

A construct was generated encoding the VP4 peptide$_{1-31}$ (HRV14 serotype) genetically fused at the N-terminus of the S antigen of hepatitis B virus (HBsAg). This fusion protein (VP4-S) was co-expressed, in the yeast *Pichia pastoris*, with a 230aa wild-type HBsAg fragment (S). The resulting strain synthesises two polypeptides, S and VP4-S fusion protein, that spontaneously co-assemble into mixed lipoprotein particles (VP4-S,S).

The *Pichia pastoris* strain used for the production of these mixed particles carries separate expression cassettes for each protein. These cassettes were stably integrated into the *Pichia* genome using linear integration vectors.

Construction of VP4 peptide-pMK Recombinant Plasmid

Figure 16B:
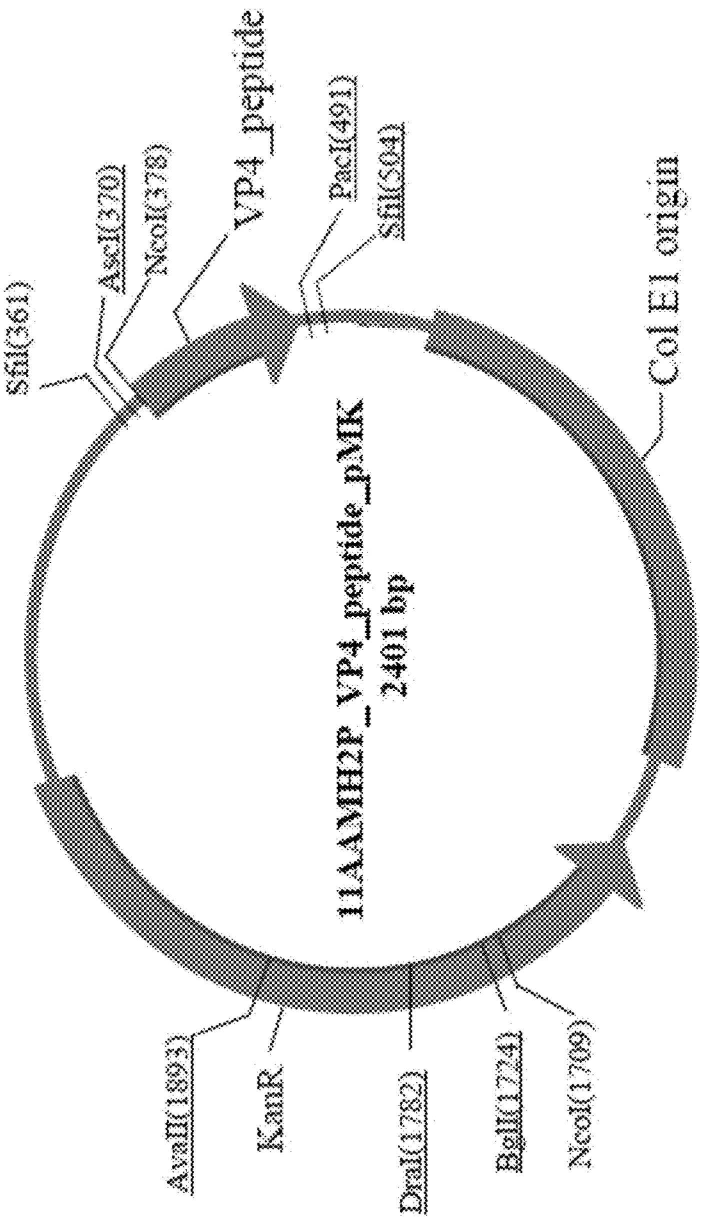
FIG. 16B shows a schematic of the VP4 peptide-Pmk plasmid map.

A synthetic DNA fragment coding for the VP4 peptide (31aa) was generated by Geneart. The fragment was cloned into pMK vector using PacI and AscI cloning sites (Geneart proprietary plasmid). The nucleotide sequence (codon-optimized for *Pichia* expression) and the corresponding amino acid sequence are illustrated in FIG. 16-A. The map of the VP4 peptide-pMK plasmid is illustrated in FIG. 16-B.

Construction of PHIL-D2mod/VP4-S Integration Vector

The VP4 synthetic DNA fragment was PCR amplified using VP4 peptide-pMK plasmid as template and the following primers pair:

```
VP4-Fw:
CTCACTATAGGGCGAATTGAAGGAAGG

VP4-Rv:
TTTGAATAGTATCCCGGGGTAGTTGATAAC
```

The PCR product was restricted with NcoI and SmaI, gel purified, and cloned into PHIL-D2mod vector, which already carries the S gene of Hepatitis B virus (PHIL-D2mod/S-fusion vector). The resulting recombinant plasmid carries the VP4-S fusion gene and was designated PHIL-D2mod/VP4-S vector. The VP4-S fusion gene and the corresponding amino acid sequence are detailed in FIG. 17.

The map of PHIL-D2mod/VP4-S vector is illustrated in FIG. 20. In this expression vector, the recombinant gene is under the control of the strong, tightly regulated methanol inducible AOX1 promoter.

The PHIL-D2-mod backbone vector is a derivative of the commercial PHIL-D2 vector (Invitrogen). The PHIL-D2 commercial vector was modified in such a way that expression of a heterologous protein starts at the native ATG start codon of the *Pichia* AOX1 gene and will potentially produce a recombinant protein with a C-terminal histidine tag. PHIL-D2-mod vector is illustrated in FIG. 19.

Construction of PHIL-D2mod/S Integration Vector

PHIL-D2mod/S vector has been designed to allow the production of S antigen alone (without any fusion partner).

A synthetic DNA fragment coding for the S antigen (227aa) was generated by Geneart. The synthetic gene was codon-optimized for expression in *Pichia pastoris* (designated Sco gene). This synthetic DNA fragment was cloned into PHIL-D2mod vector between NcoI and EcoRI sites. The recombinant plasmid containing Sco gene was designated PHIL-D2mod/S. The map of PHIL-D2mod/S vector is illustrated in FIG. 21. In this expression vector, the recombinant gene is under the control of the strong, tightly regulated methanol inducible AOX1 promoter.

Generation of *P. pastoris* Strain Co-expressing VP4-S and S Proteins

PHIL-D2mod/VP4-S and PHIL-D2mod/S expression vectors were used to transform *Pichia pastoris* GS 115 (his4) strain. Prior to transformation, the vectors were digested with NotI enzyme in order to release a DNA fragment containing the expression cassette (VP4-S or S) plus the HIS4 gene (to complement his4 in the host genome).

As both ends of the NotI DNA integrative fragment are homologous to the AOX1 region of the *Pichia* genome, it can integrate into AOX1 locus by homologous recombination. A total of 100 $His^+$ transformants were obtained and 'multicopy' integrant clones were selected by semi-quantitative DNA dot blot analysis. Some "high-copy" candidates were selected, methanol induced and their recombinant protein production was analyzed by Coomassie stained gel and Western blot. Finally transforment clone n° 49 was selected for further analysis.

Particulate Formation Evaluation

In order to determine whether VP4-S and S proteins produced in *Pichia* recombinant clone n° 49 assemble into particulate structures, soluble extract was prepared (after methanol induction) and analyzed by CsCl density gradient centrifugation. Soluble extract (15 mg of total protein) was loaded on a 10 ml 1.5M CsCl gradient (72 hours at 40000 rpm, +8° C. in a Beckman 50 Ti rotor). Fractions (0.5 ml) were collected and run on 12% SDS-PAGE, transferred to nitrocellulose membrane and analyzed using an anti-S monoclonal antibody (panel A). As shown in FIG. 22 Western blot peaks corresponding to VP4-S fusion protein and S protein appear at the same fraction of the gradient corresponding to a buoyant density (rho) of rho=1.20 suggesting that mixed particles, containing both VP4-S and S monomers, are formed in this strain.

The buoyent density (rho) of the peak fraction was calculated from a measure of its refractive index (Panel A)

Panel B: two peak fractions were analyzed by Silver-staining (left) and Coomassie-staining (right).

Purification of VP4-S,S Mixed Particles

The following method was used to VP4-S,S mixed particles from the soluble fraction of *Pichia* recombinant clone no 49.

The purification method comprises the following steps:

cell paste homogenization (French Press)

clarification by centrifugation 2 successive 1.5 M CsCl gradients 1 gel filtration step (HR300)

Concentration (Amicon)

Sterile iltration (0.22 μm)

As example, BMP201 purified bulk is illustrated in FIG. 23.

EM Analysis

Electron microscopy analysis was performed on the BMP201 purified bulk. Particles were visualized after negative staining with phosphotungstic acid. The scale is equivalent to 100 nm (FIG. 24). Many particles (20-40 nm) can clearly be identified.

LIST OF REFERENCES

Arnold E, Rossmann M G (1990). Analysis of the structure of a common cold virus, human rhinovirus 14, refined at a resolution of 3.0 A. J Mol Biol. 211(4):763-801.

Bartlett N W et al (2008) Mouse models of rhinovirus-induced disease and exacerbation of allergic airway inflammation. Nat Med. February; 14(2):199-204. doi: 10.1038/nm1713. Epub 2008 Feb. 3.

Chen et al (2000). Mol. Cell 5, 557-567.

Cheng-Yu Chung et al (2010). Vaccine 28 (2010) 6951-6957.

Edlmayr et al (2011). Antibodies induced with recombinant VP1 from human rhinovirus exhibit cross-neutralisation. Eur. Respir. J. 37:44-52.

Katpally U, Fu T M, Freed D C, Casimiro D R, Smith T J (2009). Antibodies to the buried N terminus of rhinovirus VP4 exhibit cross-serotypic neutralization. J Virol. 83(14):7040-8.

Leenaars P, Hendriksel C F, Angulo A F, Koedam M A, Claassen E. (1994) Evaluation of several adjuvants as alternatives to the use of Freund's adjuvant in rabbits. Vet Immunol Immunopathol. March; 40(3):225-41.

Lewis J K, Bothner B, Smith T J, Siuzdak G (1998). Antiviral agent blocks breathing of the common cold virus. Proc Natl Acad Sci USA. 95(12):6774-8.

Lewis-Rogers N, Bendall M L, Crandall K A (2009). Phylogenetic Relationships and Molecular Adaptation Dynamics of Human Rhinoviruses. Mol Biol. Evol. 26(5): 969-981.

Miao L Y et al (2009). Monoclonal Antibodies to VP1 Recognize a Broad Range of Enteroviruses. J. Clin. Micorbiol. Vol 47, No 10, 3108-3113.

McCray J, Werner G (1987). Different rhinovirus serotypes neutralized by antipeptide antibodies. Nature. October 22-28; 329(6141):736-8.

Niespodziana K et al (2012). Misdirected antibody responses against an N-terminal epitope on human rhinovirus VP1 as explanation for recurrent RV infections. The FASEB Journal. Vol 26, 1001-1008.

Palmenberg A C, Rathe J A, Liggett S B (2010). Analysis of the complete genome sequences of human rhinovirus. J. Allergy Clin. Immunol Vol 125, No 6, 1190-1199.

Phillips T, Jenkinson L, McCrae C, Thong B, Unitt J. (2011). Development of a high-throughput human rhinovirus infectivity cell-based assay for identifying antiviral compounds. J Virol Methods. May; 173(2):182-8.

Rollinger J M and Schmidtke M (2009). The Human Rhinovirus: Human-Pathological Impact, Mechanisms of Antirhinoviral Agents, and Strategies for Their Discovery. Medicinal Research Reviews, 31, No. 1, 42-92.

The invention claimed is:

1. An immunogenic composition comprising:

(a) a fusion protein comprising a carrier protein coupled to a human rhinovirus (HRV) peptide, said HRV peptide comprising no more than 20 amino acids from the N terminus of HRV VP4 and comprising a sequence selected from SEQ ID NO:5, SEQ ID NO:6, and SEQ ID NO:7; and (b) a pharmaceutically acceptable diluent, excipient or carrier.

2. The immunogenic composition of claim 1, wherein said HRV peptide consists of a sequence selected from:

```
HRV14 (B):
                                  [SEQ ID NO: 5]
1-GAQVSTQKSGSHENQN-16;

HRV100 (A-M):
                                  [SEQ ID NO: 6]
1-GAQVSRQNVGTHSTQN-16;
and

HRV_C_026:
                                  [SEQ ID NO: 7]
1-GAQVSRQSVGSHETMI-16.
```

3. The immunogenic composition of claim 1, wherein said carrier protein is CRM197.

4. The immunogenic composition of claim 1, further comprising an adjuvant.

5. The immunogenic composition of claim 4, wherein the adjuvant comprises at least one of: an aluminium salt; 3-O-deacylated monophosphoryl lipid A (3D-MPL); QS21; and liposomes.

6. A fusion protein comprising a carrier protein coupled to a HRV peptide, said HRV peptide comprising no more than 20 amino acids from the N terminus of VP4 and comprising a sequence selected from SEQ ID NO:5, SEQ ID NO:6, and SEQ ID NO:7.

7. The fusion protein of claim 6, wherein said HRV peptide consists of an amino acid sequence selected from:

```
HRV14 (B):
                                  [SEQ ID NO: 5]
1-GAQVSTQKSGSHENQN-16;

HRV100 (A-M):
                                  [SEQ ID NO: 6]
1-GAQVSRQNVGTHSTQN-16;
and

HRV_C_026:
                                  [SEQ ID NO: 7]
1-GAQVSRQSVGSHETMI-16.
```

8. A method for preparing an immunogenic composition which method comprises combining: a fusion protein comprising a carrier protein coupled to a human rhinovirus (HRV) peptide, said HRV peptide comprising no more than 20 amino acids from the N terminus of HRV VP4 and comprising a sequence selected from SEQ ID NO:5, SEQ ID NO:6, and SEQ ID NO:7, and a pharmaceutically acceptable diluent, excipient, or carrier.

* * * * *

SEQUENCE LISTING

```
<160> NUMBER OF SEQ ID NOS: 178

<210> SEQ ID NO 1
<211> LENGTH: 14
<212> TYPE: PRT
<213> ORGANISM: Enterovirus 70

<400> SEQUENCE: 1

Pro Ile Leu Thr Ala Asn Glu Thr Gly Ala Thr Met Pro Val
1               5                   10


<210> SEQ ID NO 2
<211> LENGTH: 14
<212> TYPE: PRT
<213> ORGANISM: Enterovirus 70

<400> SEQUENCE: 2

Pro Ala Leu Asp Ala Ala Glu Thr Gly His Thr Ser Ser Val
1               5                   10


<210> SEQ ID NO 3
<211> LENGTH: 14
<212> TYPE: PRT
<213> ORGANISM: Enterovirus 70

<400> SEQUENCE: 3

Pro Ile Leu Asp Ala Ala Glu Thr Gly His Thr Ser Asn Val
1               5                   10


<210> SEQ ID NO 4
<211> LENGTH: 14
<212> TYPE: PRT
<213> ORGANISM: Enterovirus 70

<400> SEQUENCE: 4

Gln Ala Leu Gly Ala Val Glu Ile Gly Ala Thr Ala Asp Val
1               5                   10


<210> SEQ ID NO 5
<211> LENGTH: 16
<212> TYPE: PRT
<213> ORGANISM: Enterovirus 70

<400> SEQUENCE: 5

Gly Ala Gln Val Ser Thr Gln Lys Ser Gly Ser His Glu Asn Gln Asn
1               5                   10                  15


<210> SEQ ID NO 6
<211> LENGTH: 16
<212> TYPE: PRT
<213> ORGANISM: Enterovirus 70
```

<400> SEQUENCE: 6

Gly Ala Gln Val Ser Arg Gln Asn Val Gly Thr His Ser Thr Gln Asn
1 5 10 15

<210> SEQ ID NO 7
<211> LENGTH: 16
<212> TYPE: PRT
<213> ORGANISM: Enterovirus 70

<400> SEQUENCE: 7

Gly Ala Gln Val Ser Arg Gln Ser Val Gly Ser His Glu Thr Met Ile
1 5 10 15

<210> SEQ ID NO 8
<211> LENGTH: 16
<212> TYPE: PRT
<213> ORGANISM: Enterovirus 70

<400> SEQUENCE: 8

Val Val Gln Ala Met Tyr Val Pro Pro Gly Ala Pro Asn Pro Lys Glu
1 5 10 15

<210> SEQ ID NO 9
<211> LENGTH: 30
<212> TYPE: PRT
<213> ORGANISM: Enterovirus 70

<400> SEQUENCE: 9

Ser Ser Ala Gly Gln Ser Leu Ser Met Asp Pro Ser Lys Phe Thr Glu
1 5 10 15

Pro Val Lys Asp Leu Met Leu Lys Gly Ala Pro Ala Leu Asn
20 25 30

<210> SEQ ID NO 10
<211> LENGTH: 30
<212> TYPE: PRT
<213> ORGANISM: Enterovirus 70

<400> SEQUENCE: 10

Gly Leu Gly Asp Glu Leu Glu Glu Val Ile Val Glu Lys Thr Lys Gln
1 5 10 15

Thr Val Ala Ser Ile Ser Ser Gly Pro Lys His Thr Gln Lys
20 25 30

<210> SEQ ID NO 11
<211> LENGTH: 31
<212> TYPE: PRT
<213> ORGANISM: Enterovirus 70

<400> SEQUENCE: 11

Gly Ala Gln Val Ser Thr Gln Lys Ser Gly Ser His Glu Asn Gln Asn
1 5 10 15

Ile Leu Thr Asn Gly Ser Asn Gln Thr Phe Thr Val Ile Asn Tyr
20 25 30

<210> SEQ ID NO 12
<211> LENGTH: 792
<212> TYPE: DNA
<213> ORGANISM: Enterovirus 70

<400> SEQUENCE: 12
atggttggtg ctcaagtttc cactcaaaag tctggttccc acgagaacca gaacatcttg 60

-continued

```
actaacggtt ccaaccagac tttcactgtt atcaactacc ccgtgaccaa catggaaaac    120

atcacctctg gtttcttggg tccattattg gttttacaag ctggtttctt cttgttgacc    180

agaattttaa ctattccaca atctttggac tcatggtgga cctccttgaa cttcttgggt    240

ggttctccag tttgtttggg tcaaaactcc caatccccaa cttccaacca ttctcctact    300

tcttgtccac caatctgtcc aggttacaga tggatgtgtt tgagaagatt tatcattttc    360

ttgttcatcc tattgttgtg tttgatcttc ctattggttt tgttggatta ccaaggtatg    420

ttaccagttt gtccattgat cccaggttcc actactacca acactggtcc atgtaagacc    480

tgtactactc cagctcaagg taactcaatg tttccatctt gttgttgtac caagccaacc    540

gacggtaact gtacttgtat cccaattcca tcttcctggg ctttcgctaa gtacttgtgg    600

gaatgggctt ccgttagatt ctcttggttg tctttgttgg ttccattcgt tcaatggttc    660

gttggtttgt ccccaaccgt ctggttgtct gctatctgga tgatgtggta ctggggtcca    720

tctttgtact ctatcgtctc tccattcatc ccattgttac caatcttctt ctgtttgtgg    780

gtctacattt aa                                                        792


<210> SEQ ID NO 13
<211> LENGTH: 263
<212> TYPE: PRT
<213> ORGANISM: Enterovirus 70

<400> SEQUENCE: 13

Met Val Gly Ala Gln Val Ser Thr Gln Lys Ser Gly Ser His Glu Asn
1               5                   10                  15

Gln Asn Ile Leu Thr Asn Gly Ser Asn Gln Thr Phe Thr Val Ile Asn
            20                  25                  30

Tyr Pro Val Thr Asn Met Glu Asn Ile Thr Ser Gly Phe Leu Gly Pro
        35                  40                  45

Leu Leu Val Leu Gln Ala Gly Phe Phe Leu Leu Thr Arg Ile Leu Thr
    50                  55                  60

Ile Pro Gln Ser Leu Asp Ser Trp Trp Thr Ser Leu Asn Phe Leu Gly
65                  70                  75                  80

Gly Ser Pro Val Cys Leu Gly Gln Asn Ser Gln Ser Pro Thr Ser Asn
                85                  90                  95

His Ser Pro Thr Ser Cys Pro Pro Ile Cys Pro Gly Tyr Arg Trp Met
            100                 105                 110

Cys Leu Arg Arg Phe Ile Ile Phe Leu Phe Ile Leu Leu Leu Cys Leu
        115                 120                 125

Ile Phe Leu Leu Val Leu Leu Asp Tyr Gln Gly Met Leu Pro Val Cys
    130                 135                 140

Pro Leu Ile Pro Gly Ser Thr Thr Thr Asn Thr Gly Pro Cys Lys Thr
145                 150                 155                 160

Cys Thr Thr Pro Ala Gln Gly Asn Ser Met Phe Pro Ser Cys Cys Cys
                165                 170                 175

Thr Lys Pro Thr Asp Gly Asn Cys Thr Cys Ile Pro Ile Pro Ser Ser
            180                 185                 190

Trp Ala Phe Ala Lys Tyr Leu Trp Glu Trp Ala Ser Val Arg Phe Ser
        195                 200                 205

Trp Leu Ser Leu Leu Val Pro Phe Val Gln Trp Phe Val Gly Leu Ser
    210                 215                 220

Pro Thr Val Trp Leu Ser Ala Ile Trp Met Met Trp Tyr Trp Gly Pro
225                 230                 235                 240
```

Ser Leu Tyr Ser Ile Val Ser Pro Phe Ile Pro Leu Leu Pro Ile Phe
245 250 255

Phe Cys Leu Trp Val Tyr Ile
260

<210> SEQ ID NO 14
<211> LENGTH: 684
<212> TYPE: DNA
<213> ORGANISM: Enterovirus 70

<400> SEQUENCE: 14
atggttgaga acatcacttc cggtttcttg ggaccattgt tggttttgca ggctggattc 60
ttcttattga ctagaatctt gactatccca cagtctttgg actcttggtg gacttccttg 120
aacttcttgg gaggttctcc agtttgtttg ggacaaaact cccaatctcc aacttctaac 180
cactccccaa cttcatgtcc accaatctgt ccaggttaca gatggatgtg tttgagaaga 240
ttcatcattt tcttgttcat cttgttgttg tgtttgatct tcttgttggt tttgttggac 300
taccagggaa tgttgccagt ttgtccattg attccaggtt ccactactac aaacactggt 360
ccatgtaaga cttgtactac tccagctcag ggaaactcta tgttcccatc ctgttgttgt 420
actaagccaa ctgacggtaa ctgtacttgt atcccaattc catcctcttg ggctttcgct 480
aagtacttgt gggaatgggc ttctgttaga ttctcctggt tgtccttgtt ggttccattc 540
gttcagtggt tcgttggttt gtctccaact gtttggttgt ccgctatctg gatgatgtgg 600
tactggggac catctttgta ctccatcgtt tccccattca tcccattgtt gccaatcttt 660
ttctgtttgt gggtttacat ctag 684

<210> SEQ ID NO 15
<211> LENGTH: 227
<212> TYPE: PRT
<213> ORGANISM: Enterovirus 70

<400> SEQUENCE: 15

Met Val Glu Asn Ile Thr Ser Gly Phe Leu Gly Pro Leu Leu Val Leu
1 5 10 15

Gln Ala Gly Phe Phe Leu Leu Thr Arg Ile Leu Thr Ile Pro Gln Ser
20 25 30

Leu Asp Ser Trp Trp Thr Ser Leu Asn Phe Leu Gly Gly Ser Pro Val
35 40 45

Cys Leu Gly Gln Asn Ser Gln Ser Pro Thr Ser Asn His Ser Pro Thr
50 55 60

Ser Cys Pro Pro Ile Cys Pro Gly Tyr Arg Trp Met Cys Leu Arg Arg
65 70 75 80

Phe Ile Ile Phe Leu Phe Ile Leu Leu Leu Cys Leu Ile Phe Leu Leu
85 90 95

Val Leu Leu Asp Tyr Gln Gly Met Leu Pro Val Cys Pro Leu Ile Pro
100 105 110

Gly Ser Thr Thr Thr Asn Thr Gly Pro Cys Lys Thr Cys Thr Thr Pro
115 120 125

Ala Gln Gly Asn Ser Met Phe Pro Ser Cys Cys Cys Thr Lys Pro Thr
130 135 140

Asp Gly Asn Cys Thr Cys Ile Pro Ile Pro Ser Ser Trp Ala Phe Ala
145 150 155 160

Lys Tyr Leu Trp Glu Trp Ala Ser Val Arg Phe Ser Trp Leu Ser Leu
165 170 175

```
Leu Val Pro Phe Val Gln Trp Phe Val Gly Leu Ser Pro Thr Val Trp
            180                 185                 190

Leu Ser Ala Ile Trp Met Met Trp Tyr Trp Gly Pro Ser Leu Tyr Ser
        195                 200                 205

Ile Val Ser Pro Phe Ile Pro Leu Leu Pro Ile Phe Phe Cys Leu Trp
    210                 215                 220

Val Tyr Ile
225


<210> SEQ ID NO 16
<211> LENGTH: 14
<212> TYPE: PRT
<213> ORGANISM: Enterovirus 70

<400> SEQUENCE: 16

Pro Leu Leu Asp Ala Ala Glu Thr Gly His Thr Ser Asn Val
1               5                   10


<210> SEQ ID NO 17
<211> LENGTH: 14
<212> TYPE: PRT
<213> ORGANISM: Enterovirus 70

<400> SEQUENCE: 17

Pro Ala Leu Asp Ala Ala Glu Thr Gly His Thr Ser Asn Val
1               5                   10


<210> SEQ ID NO 18
<211> LENGTH: 14
<212> TYPE: PRT
<213> ORGANISM: Enterovirus 70

<400> SEQUENCE: 18

Pro Ile Leu Asp Ala Ala Glu Thr Gly His Thr Ser Ser Val
1               5                   10


<210> SEQ ID NO 19
<211> LENGTH: 14
<212> TYPE: PRT
<213> ORGANISM: Enterovirus 70

<400> SEQUENCE: 19

Pro Ala Leu Asp Ala Ala Glu Thr Gly His Thr Ser Lys Val
1               5                   10


<210> SEQ ID NO 20
<211> LENGTH: 14
<212> TYPE: PRT
<213> ORGANISM: Enterovirus 70

<400> SEQUENCE: 20

Pro Ala Leu Asp Ala Ala Glu Thr Gly His Thr Ser Gln Thr
1               5                   10


<210> SEQ ID NO 21
<211> LENGTH: 14
<212> TYPE: PRT
<213> ORGANISM: Enterovirus 70

<400> SEQUENCE: 21

Pro Val Leu Asp Ala Ala Glu Thr Gly His Thr Asn Lys Ile
1               5                   10
```

<210> SEQ ID NO 22
<211> LENGTH: 14
<212> TYPE: PRT
<213> ORGANISM: Enterovirus 70

<400> SEQUENCE: 22

Pro Ala Leu Asp Ala Ala Glu Thr Gly His Thr Asn Gln Val
1 5 10

<210> SEQ ID NO 23
<211> LENGTH: 14
<212> TYPE: PRT
<213> ORGANISM: Enterovirus 70

<400> SEQUENCE: 23

Pro Ala Leu Asp Ala Ala Glu Thr Gly His Thr Asn Asn Val
1 5 10

<210> SEQ ID NO 24
<211> LENGTH: 14
<212> TYPE: PRT
<213> ORGANISM: Enterovirus 70

<400> SEQUENCE: 24

Thr Ala Leu Asp Ala Ala Glu Thr Gly His Thr Ser Ser Ile
1 5 10

<210> SEQ ID NO 25
<211> LENGTH: 14
<212> TYPE: PRT
<213> ORGANISM: Enterovirus 70

<400> SEQUENCE: 25

Pro Ala Leu Asp Ala Ala Glu Thr Gly His Thr Ser Asn Ile
1 5 10

<210> SEQ ID NO 26
<211> LENGTH: 14
<212> TYPE: PRT
<213> ORGANISM: Enterovirus 70

<400> SEQUENCE: 26

Pro Ala Leu Asp Ala Ala Glu Thr Gly His Thr Ser Gln Val
1 5 10

<210> SEQ ID NO 27
<211> LENGTH: 14
<212> TYPE: PRT
<213> ORGANISM: Enterovirus 70

<400> SEQUENCE: 27

Pro Ala Leu Asp Ala Ala Glu Thr Gly His Thr Ser Gln Ile
1 5 10

<210> SEQ ID NO 28
<211> LENGTH: 14
<212> TYPE: PRT
<213> ORGANISM: Enterovirus 70

<400> SEQUENCE: 28

Pro Ala Leu Asp Ala Ala Glu Thr Gly His Thr Ser Gly Ile
1 5 10

<210> SEQ ID NO 29

<211> LENGTH: 14
<212> TYPE: PRT
<213> ORGANISM: Enterovirus 70

<400> SEQUENCE: 29

Pro Val Leu Asp Ala Ala Glu Thr Gly His Thr Ser Asn Val
1 5 10

<210> SEQ ID NO 30
<211> LENGTH: 14
<212> TYPE: PRT
<213> ORGANISM: Enterovirus 70

<400> SEQUENCE: 30

Pro Ala Leu Asp Ala Ala Glu Thr Gly His Thr Ser Ala Ile
1 5 10

<210> SEQ ID NO 31
<211> LENGTH: 14
<212> TYPE: PRT
<213> ORGANISM: Enterovirus 70

<400> SEQUENCE: 31

Pro Ala Leu Asp Ala Ala Glu Thr Gly His Thr Ser Ser Ile
1 5 10

<210> SEQ ID NO 32
<211> LENGTH: 14
<212> TYPE: PRT
<213> ORGANISM: Enterovirus 70

<400> SEQUENCE: 32

Pro Val Leu Asp Ala Ala Glu Thr Gly His Thr Ser Ser Ile
1 5 10

<210> SEQ ID NO 33
<211> LENGTH: 14
<212> TYPE: PRT
<213> ORGANISM: Enterovirus 70

<400> SEQUENCE: 33

Pro Ile Leu Asp Ala Ala Glu Thr Gly His Thr Ser Lys Val
1 5 10

<210> SEQ ID NO 34
<211> LENGTH: 14
<212> TYPE: PRT
<213> ORGANISM: Enterovirus 70

<400> SEQUENCE: 34

Pro Ala Leu Asp Ala Ala Glu Thr Gly His Thr Ser Gly Val
1 5 10

<210> SEQ ID NO 35
<211> LENGTH: 14
<212> TYPE: PRT
<213> ORGANISM: Enterovirus 70

<400> SEQUENCE: 35

Pro Ala Leu Asp Ala Ala Glu Thr Gly His Thr Ser His Val
1 5 10

<210> SEQ ID NO 36
<211> LENGTH: 14
<212> TYPE: PRT

-continued

<213> ORGANISM: Enterovirus 70

<400> SEQUENCE: 36

Pro Val Leu Asp Ala Ala Glu Thr Gly His Thr Asn Gln Val
1 5 10

<210> SEQ ID NO 37
<211> LENGTH: 14
<212> TYPE: PRT
<213> ORGANISM: Enterovirus 70

<400> SEQUENCE: 37

Pro Thr Leu Asp Ala Ala Glu Thr Gly His Thr Ser Gln Val
1 5 10

<210> SEQ ID NO 38
<211> LENGTH: 14
<212> TYPE: PRT
<213> ORGANISM: Enterovirus 70

<400> SEQUENCE: 38

Pro Val Leu Asp Ala Ala Glu Thr Gly His Thr Ser Asn Ile
1 5 10

<210> SEQ ID NO 39
<211> LENGTH: 14
<212> TYPE: PRT
<213> ORGANISM: Enterovirus 70

<400> SEQUENCE: 39

Pro Ala Leu Asp Ala Ala Glu Thr Gly His Thr Ser Thr Val
1 5 10

<210> SEQ ID NO 40
<211> LENGTH: 14
<212> TYPE: PRT
<213> ORGANISM: Enterovirus 70

<400> SEQUENCE: 40

Pro Ala Leu Asp Ala Ala Glu Thr Gly His Thr Ser Asp Val
1 5 10

<210> SEQ ID NO 41
<211> LENGTH: 14
<212> TYPE: PRT
<213> ORGANISM: Enterovirus 70

<400> SEQUENCE: 41

Pro Thr Leu Asp Ala Ala Glu Thr Gly His Thr Ser Gly Ile
1 5 10

<210> SEQ ID NO 42
<211> LENGTH: 14
<212> TYPE: PRT
<213> ORGANISM: Enterovirus 70

<400> SEQUENCE: 42

Pro Val Leu Asp Ala Ala Glu Thr Gly His Thr Ser Gln Thr
1 5 10

<210> SEQ ID NO 43
<211> LENGTH: 14
<212> TYPE: PRT
<213> ORGANISM: Enterovirus 70

<400> SEQUENCE: 43

Pro Ala Leu Asp Ala Ala Glu Thr Gly His Thr Asn Gln Thr
1 5 10

<210> SEQ ID NO 44
<211> LENGTH: 14
<212> TYPE: PRT
<213> ORGANISM: Enterovirus 70

<400> SEQUENCE: 44

Pro Ala Leu Thr Ala Asn Glu Thr Gly Ala Thr Leu Pro Thr
1 5 10

<210> SEQ ID NO 45
<211> LENGTH: 14
<212> TYPE: PRT
<213> ORGANISM: Enterovirus 70

<400> SEQUENCE: 45

Pro Ser Leu Thr Ala Asn Glu Thr Gly Ala Thr Leu Pro Thr
1 5 10

<210> SEQ ID NO 46
<211> LENGTH: 14
<212> TYPE: PRT
<213> ORGANISM: Enterovirus 70

<400> SEQUENCE: 46

Pro Ile Leu Thr Ala Asn Glu Thr Gly Ala Thr Met Pro Thr
1 5 10

<210> SEQ ID NO 47
<211> LENGTH: 14
<212> TYPE: PRT
<213> ORGANISM: Enterovirus 70

<400> SEQUENCE: 47

Pro Ala Leu Ser Ala Asn Glu Thr Gly Ala Thr Leu Pro Thr
1 5 10

<210> SEQ ID NO 48
<211> LENGTH: 14
<212> TYPE: PRT
<213> ORGANISM: Enterovirus 70

<400> SEQUENCE: 48

Pro Ala Leu Thr Ala Asn Glu Thr Gly Ala Thr Met Pro Thr
1 5 10

<210> SEQ ID NO 49
<211> LENGTH: 14
<212> TYPE: PRT
<213> ORGANISM: Enterovirus 70

<400> SEQUENCE: 49

Pro Thr Leu Ser Ala Ser Glu Thr Gly Thr Thr Leu Pro Thr
1 5 10

<210> SEQ ID NO 50
<211> LENGTH: 14
<212> TYPE: PRT
<213> ORGANISM: Enterovirus 70

<400> SEQUENCE: 50

-continued

Pro Met Leu Thr Ala Asn Glu Thr Gly Ala Ser Met Pro Val
1 5 10

<210> SEQ ID NO 51
<211> LENGTH: 14
<212> TYPE: PRT
<213> ORGANISM: Enterovirus 70

<400> SEQUENCE: 51

Pro Thr Leu Thr Ala Asn Glu Thr Gly Ala Ser Met Pro Val
1 5 10

<210> SEQ ID NO 52
<211> LENGTH: 14
<212> TYPE: PRT
<213> ORGANISM: Enterovirus 70

<400> SEQUENCE: 52

Pro Thr Leu Thr Ala Asn Glu Thr Gly Ala Thr Met Pro Thr
1 5 10

<210> SEQ ID NO 53
<211> LENGTH: 14
<212> TYPE: PRT
<213> ORGANISM: Enterovirus 70

<400> SEQUENCE: 53

Pro Ala Leu Ser Ala Ser Glu Thr Gly Ala Thr Leu Pro Thr
1 5 10

<210> SEQ ID NO 54
<211> LENGTH: 14
<212> TYPE: PRT
<213> ORGANISM: Enterovirus 70

<400> SEQUENCE: 54

Pro Thr Leu Ser Ala Ser Glu Thr Gly Ala Thr Leu Gln Thr
1 5 10

<210> SEQ ID NO 55
<211> LENGTH: 14
<212> TYPE: PRT
<213> ORGANISM: Enterovirus 70

<400> SEQUENCE: 55

Pro Ser Leu Ser Ala Asn Glu Thr Gly Ala Thr Met Pro Thr
1 5 10

<210> SEQ ID NO 56
<211> LENGTH: 14
<212> TYPE: PRT
<213> ORGANISM: Enterovirus 70

<400> SEQUENCE: 56

Pro Thr Leu Ser Ala Ser Glu Thr Gly Ala Thr Leu Pro Thr
1 5 10

<210> SEQ ID NO 57
<211> LENGTH: 14
<212> TYPE: PRT
<213> ORGANISM: Enterovirus 70

<400> SEQUENCE: 57

Ser Ile Leu Gly Ala Met Glu Ile Gly Ala Ser Ser Asn Ala
1 5 10

<210> SEQ ID NO 58
<211> LENGTH: 14
<212> TYPE: PRT
<213> ORGANISM: Enterovirus 70

<400> SEQUENCE: 58

Ser Ala Leu Gly Ala Met Glu Ile Gly Ala Ser Ser Thr Thr
1 5 10

<210> SEQ ID NO 59
<211> LENGTH: 14
<212> TYPE: PRT
<213> ORGANISM: Enterovirus 70

<400> SEQUENCE: 59

Thr Ala Leu Ser Ala Met Glu Ile Gly Ala Ser Ser Asp Val
1 5 10

<210> SEQ ID NO 60
<211> LENGTH: 14
<212> TYPE: PRT
<213> ORGANISM: Enterovirus 70

<400> SEQUENCE: 60

Thr Ala Leu Gly Ala Met Glu Ile Gly Ala Ser Ser Asp Ala
1 5 10

<210> SEQ ID NO 61
<211> LENGTH: 14
<212> TYPE: PRT
<213> ORGANISM: Enterovirus 70

<400> SEQUENCE: 61

Gln Thr Leu Gly Ala Leu Glu Ile Gly Ala Thr Ala Glu Ile
1 5 10

<210> SEQ ID NO 62
<211> LENGTH: 14
<212> TYPE: PRT
<213> ORGANISM: Enterovirus 70

<400> SEQUENCE: 62

Ser Ala Leu Asn Ala Met Glu Val Gly Val Thr Pro Asp Val
1 5 10

<210> SEQ ID NO 63
<211> LENGTH: 14
<212> TYPE: PRT
<213> ORGANISM: Enterovirus 70

<400> SEQUENCE: 63

Ser Ala Leu Gly Ala Met Glu Ile Gly Ala Ser Ser Ser Val
1 5 10

<210> SEQ ID NO 64
<211> LENGTH: 14
<212> TYPE: PRT
<213> ORGANISM: Enterovirus 70

<400> SEQUENCE: 64

Thr Val Leu Asn Ala Met Glu Ile Gly Val Thr Pro Asp Ala
1 5 10

-continued

<210> SEQ ID NO 65
<211> LENGTH: 14
<212> TYPE: PRT
<213> ORGANISM: Enterovirus 70

<400> SEQUENCE: 65

Gln Ala Leu Gly Ala Leu Glu Ile Gly Ala Thr Ala Asp Val
1 5 10

<210> SEQ ID NO 66
<211> LENGTH: 14
<212> TYPE: PRT
<213> ORGANISM: Enterovirus 70

<400> SEQUENCE: 66

Gln Ala Leu Gly Ala Leu Glu Ile Gly Ala Thr Ala Asp Leu
1 5 10

<210> SEQ ID NO 67
<211> LENGTH: 16
<212> TYPE: PRT
<213> ORGANISM: Enterovirus 70

<400> SEQUENCE: 67

Gly Ala Gln Val Ser Arg Gln Asn Val Gly Thr His Leu Thr His Asn
1 5 10 15

<210> SEQ ID NO 68
<211> LENGTH: 16
<212> TYPE: PRT
<213> ORGANISM: Enterovirus 70

<400> SEQUENCE: 68

Gly Ala Gln Val Pro Arg Gln Lys Val Gly Thr His Ser Thr Gln Asn
1 5 10 15

<210> SEQ ID NO 69
<211> LENGTH: 16
<212> TYPE: PRT
<213> ORGANISM: Enterovirus 70

<400> SEQUENCE: 69

Gly Ala Gln Val Ser Thr Gln Lys Thr Gly Ser His Glu Asn Gln Asn
1 5 10 15

<210> SEQ ID NO 70
<211> LENGTH: 16
<212> TYPE: PRT
<213> ORGANISM: Enterovirus 70

<400> SEQUENCE: 70

Gly Ala Gln Val Ser Thr Gln Arg Ser Gly Ser His Glu Asn Gln Asn
1 5 10 15

<210> SEQ ID NO 71
<211> LENGTH: 16
<212> TYPE: PRT
<213> ORGANISM: Enterovirus 70

<400> SEQUENCE: 71

Gly Ala Gln Ile Ser Thr Gln Lys Ser Gly Ser His Glu Asn Gln Asn
1 5 10 15

<210> SEQ ID NO 72
<211> LENGTH: 16

<212> TYPE: PRT
<213> ORGANISM: Enterovirus 70

<400> SEQUENCE: 72

Gly Ala Gln Val Ser Arg Gln Asn Asn Gly Thr His Glu Asn Gly Val
1 5 10 15

<210> SEQ ID NO 73
<211> LENGTH: 16
<212> TYPE: PRT
<213> ORGANISM: Enterovirus 70

<400> SEQUENCE: 73

Gly Ala Gln Val Ser Lys Gln Asn Val Gly Ser His Glu Asn Ser Val
1 5 10 15

<210> SEQ ID NO 74
<211> LENGTH: 16
<212> TYPE: PRT
<213> ORGANISM: Enterovirus 70

<400> SEQUENCE: 74

Gly Ala Gln Val Ser Lys Gln Asn Val Gly Ser His Glu Ser Gly Ile
1 5 10 15

<210> SEQ ID NO 75
<211> LENGTH: 16
<212> TYPE: PRT
<213> ORGANISM: Enterovirus 70

<400> SEQUENCE: 75

Gly Ala Gln Val Ser Arg Gln Lys Val Gly Ser His Asp Asn Ala Ile
1 5 10 15

<210> SEQ ID NO 76
<211> LENGTH: 16
<212> TYPE: PRT
<213> ORGANISM: Enterovirus 70

<400> SEQUENCE: 76

Gly Ala Gln Val Ser Arg Gln Lys Val Gly Ser His Asp Asn Ala Ile
1 5 10 15

<210> SEQ ID NO 77
<211> LENGTH: 16
<212> TYPE: PRT
<213> ORGANISM: Enterovirus 70

<400> SEQUENCE: 77

Gly Ala Gln Val Ser Lys Gln Asn Thr Gly Ser His Glu Ser Ala Ile
1 5 10 15

<210> SEQ ID NO 78
<211> LENGTH: 16
<212> TYPE: PRT
<213> ORGANISM: Enterovirus 70

<400> SEQUENCE: 78

Gly Ala Gln Val Ser Lys Gln Ser Val Gly Ala His Glu Thr Met Val
1 5 10 15

<210> SEQ ID NO 79
<211> LENGTH: 91
<212> TYPE: PRT
<213> ORGANISM: Enterovirus 70

<400> SEQUENCE: 79

Gly Leu Gly Asp Glu Leu Glu Glu Val Ile Val Glu Lys Thr Lys Gln
1 5 10 15

Thr Val Ala Ser Ile Ser Ser Gly Pro Lys His Thr Gln Lys Val Pro
20 25 30

Ile Leu Thr Ala Asn Glu Thr Gly Ala Thr Met Pro Val Leu Pro Ser
35 40 45

Asp Ser Ile Glu Thr Arg Thr Thr Tyr Met His Phe Asn Gly Ser Glu
50 55 60

Thr Asp Val Glu Cys Phe Leu Gly Arg Ala Ala Cys Val His Val Thr
65 70 75 80

Glu Ile Gln Asn Lys Asp Ala Thr Gly Ile Asp
85 90

<210> SEQ ID NO 80
<211> LENGTH: 89
<212> TYPE: PRT
<213> ORGANISM: Enterovirus 70

<400> SEQUENCE: 80

Asn Pro Val Glu Asn Tyr Val Glu Gly Val Leu Asn Glu Val Leu Val
1 5 10 15

Val Pro Asn Ile Arg Glu Ser His Pro Ser Thr Ser Asn Ser Ala Pro
20 25 30

Ile Leu Asp Ala Ala Glu Thr Gly His Thr Ser Asn Val Gln Pro Glu
35 40 45

Asp Thr Val Glu Thr Arg Tyr Val Gln Thr Ser Gln Thr Arg Asp Glu
50 55 60

Met Ser Ile Glu Ser Phe Leu Gly Arg Ser Gly Cys Ile His Thr Ser
65 70 75 80

Thr Ile Thr Val Ser Lys Met Lys Asn
85

<210> SEQ ID NO 81
<211> LENGTH: 87
<212> TYPE: PRT
<213> ORGANISM: Enterovirus 70

<400> SEQUENCE: 81

Asn Pro Ile Glu Asn Tyr Val Asp Gln Val Leu Asn Glu Val Leu Val
1 5 10 15

Val Pro Asn Ile Lys Glu Ser His Pro Ser Thr Ser Asn Ser Ala Pro
20 25 30

Ile Leu Asp Ala Ala Glu Thr Gly His Thr Ser Asn Val Gln Pro Glu
35 40 45

Asp Thr Ile Glu Thr Arg Tyr Val Gln Thr Thr Gln Thr Arg Asp Glu
50 55 60

Met Ser Ile Glu Ser Phe Leu Gly Arg Ser Gly Cys Val His Thr Ser
65 70 75 80

Thr Ile Glu Thr Lys Leu Lys
85

<210> SEQ ID NO 82
<211> LENGTH: 90
<212> TYPE: PRT
<213> ORGANISM: Enterovirus 70

<400> SEQUENCE: 82

```
Asn Pro Ile Glu Gln Phe Thr Glu Ala Val Leu Asn Glu Val Leu Val
1               5                   10                  15

Val Pro Asn Thr Gln Ala Ser Asn Gly Ser Ile Ala Asn Ser Ala Pro
            20                  25                  30

Ala Leu Asp Ala Ala Glu Thr Gly His Thr Ser Ser Val Gln Pro Glu
        35                  40                  45

Asp Leu Ile Glu Thr Arg Tyr Val Ile Thr Asp Gln Thr Arg His Glu
    50                  55                  60

Thr Ser Leu Glu Ser Phe Leu Gly Arg Ala Gly Cys Ile Lys Ile Ile
65                  70                  75                  80

Ala Leu Glu Leu Asp His Asp Asn Tyr Asp
                85                  90
```

<210> SEQ ID NO 83
<211> LENGTH: 84
<212> TYPE: PRT
<213> ORGANISM: Enterovirus 70

<400> SEQUENCE: 83

```
Asn Pro Val Glu Glu Phe Val Glu His Thr Leu Lys Glu Val Leu Val
1               5                   10                  15

Val Pro Asp Thr Gln Ala Ser Gly Pro Val His Thr Thr Lys Pro Gln
            20                  25                  30

Ala Leu Gly Ala Val Glu Ile Gly Ala Thr Ala Asp Val Gly Pro Glu
        35                  40                  45

Thr Leu Ile Glu Thr Arg Tyr Val Met Asn Asp Asn Thr Asn Ala Glu
    50                  55                  60

Ala Thr Val Glu Asn Phe Leu Gly Arg Ser Ala Leu Trp Ala Asn Leu
65                  70                  75                  80

Lys Leu Asn Gln
```

<210> SEQ ID NO 84
<211> LENGTH: 105
<212> TYPE: PRT
<213> ORGANISM: Enterovirus 70

<400> SEQUENCE: 84

```
Gly Asp Gly Ile Ala Asp Met Ile Asp Gln Ala Val Thr Ser Arg Val
1               5                   10                  15

Gly Arg Ala Leu Thr Ser Leu Gln Val Glu Pro Thr Ala Ala Asn Thr
            20                  25                  30

Asn Ala Ser Glu His Arg Leu Gly Thr Gly Leu Val Pro Ala Leu Gln
        35                  40                  45

Ala Ala Glu Thr Gly Ala Ser Ser Asn Ala Gln Asp Glu Asn Leu Ile
    50                  55                  60

Glu Thr Arg Cys Val Leu Asn His His Ser Thr Gln Glu Thr Thr Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly
            100                 105
```

<210> SEQ ID NO 85
<211> LENGTH: 105
<212> TYPE: PRT
<213> ORGANISM: Enterovirus 70

<400> SEQUENCE: 85

Gly Asp Arg Val Ala Asp Val Ile Glu Ser Ser Ile Gly Asp Ser Val
1 5 10 15

Ser Arg Ala Leu Thr Arg Ala Leu Pro Ala Pro Thr Gly Gln Asp Thr
20 25 30

Gln Val Ser Ser His Arg Leu Asp Thr Gly Lys Val Pro Ala Leu Gln
35 40 45

Ala Ala Glu Ile Gly Ala Ser Ser Asn Ala Ser Asp Glu Ser Met Ile
50 55 60

Glu Thr Arg Cys Val Leu Asn Ser His Ser Thr Ala Glu Thr Thr Leu
65 70 75 80

Asp Ser Phe Phe Ser Arg Ala Gly Leu Val Gly Glu Ile Asp Leu Pro
85 90 95

Leu Glu Gly Thr Thr Asn Pro Asn Gly
100 105

<210> SEQ ID NO 86
<211> LENGTH: 94
<212> TYPE: PRT
<213> ORGANISM: Enterovirus 70

<400> SEQUENCE: 86

Ala Ala Glu Ala Ala Tyr Gln Ile Glu Ser Ile Ile Lys Thr Ala Thr
1 5 10 15

Asp Thr Val Lys Ser Glu Ile Ser Ala Glu Leu Gly Val Val Pro Ser
20 25 30

Leu Asn Ala Val Glu Thr Gly Ala Ser Ser Asn Thr Glu Pro Glu Glu
35 40 45

Ala Ile Gln Thr Arg Thr Val Ile Asn Gln His Gly Val Ser Glu Thr
50 55 60

Leu Val Glu Asn Phe Leu Ser Arg Ala Ala Leu Val Ser Lys Arg Ser
65 70 75 80

Phe Glu Tyr Lys Asn His Thr Ser Ser Lys Ala Arg Thr Asp
85 90

<210> SEQ ID NO 87
<211> LENGTH: 94
<212> TYPE: PRT
<213> ORGANISM: Enterovirus 70

<400> SEQUENCE: 87

Glu Gln Ala Ala Thr Thr Gln Ile Gly Glu Ile Val Lys Thr Val Ala
1 5 10 15

Asn Thr Val Glu Ser Asp Ile Lys Ala Glu Leu Gly Val Ile Pro Ser
20 25 30

Leu Asn Ala Val Glu Thr Gly Ala Thr Ser Asn Thr Glu Pro Glu Glu
35 40 45

Ala Ile Gln Thr Arg Thr Val Ile Asn Met His Gly Thr Ala Glu Cys
50 55 60

Leu Val Glu Asn Phe Leu Gly Arg Ser Ala Leu Val Cys Met Arg Ser
65 70 75 80

Phe Glu Tyr Lys Asn His Ser Thr Ser Thr Ser Ser Ile Gln
85 90

<210> SEQ ID NO 88
<211> LENGTH: 103

<212> TYPE: PRT
<213> ORGANISM: poliovirus

<400> SEQUENCE: 88

Gly Leu Gly Gln Met Leu Glu Ser Met Ile Asp Asn Thr Val Arg Glu
1 5 10 15

Thr Val Gly Ala Ala Thr Ser Arg Asp Ala Leu Pro Asn Thr Glu Ala
20 25 30

Ser Gly Pro Thr His Ser Lys Glu Ile Pro Ala Leu Thr Ala Val Glu
35 40 45

Thr Gly Ala Thr Asn Pro Leu Val Pro Ser Asp Thr Val Gln Thr Arg
50 55 60

His Val Val Gln His Arg Ser Arg Ser Glu Ser Ser Ile Glu Ser Phe
65 70 75 80

Phe Ala Arg Gly Ala Cys Val Thr Ile Met Thr Val Asp Asn Pro Ala
85 90 95

Ser Thr Thr Asn Lys Asp Lys
100

<210> SEQ ID NO 89
<211> LENGTH: 103
<212> TYPE: PRT
<213> ORGANISM: poliovirus

<400> SEQUENCE: 89

Gly Leu Gly Asp Leu Ile Glu Gly Val Val Glu Gly Val Thr Arg Asn
1 5 10 15

Ala Leu Thr Pro Leu Thr Pro Ala Asn Asn Leu Pro Asp Thr Gln Ser
20 25 30

Ser Gly Pro Ala His Ser Lys Glu Thr Pro Ala Leu Thr Ala Val Glu
35 40 45

Thr Gly Ala Thr Asn Pro Leu Val Pro Ser Asp Thr Val Gln Thr Arg
50 55 60

His Val Ile Gln Lys Arg Thr Arg Ser Glu Ser Thr Val Glu Ser Phe
65 70 75 80

Phe Ala Arg Gly Ala Cys Val Ala Ile Ile Glu Val Asp Asn Asp Ala
85 90 95

Pro Thr Lys Arg Ala Ser Lys
100

<210> SEQ ID NO 90
<211> LENGTH: 101
<212> TYPE: PRT
<213> ORGANISM: poliovirus

<400> SEQUENCE: 90

Gly Val Asp Asp Leu Ile Thr Glu Val Ala Gln Asn Ala Leu Ala Leu
1 5 10 15

Ser Leu Pro Lys Pro Gln Ser Asn Leu Pro Asp Thr Lys Ala Ser Gly
20 25 30

Pro Ala His Ser Lys Glu Val Pro Thr Leu Thr Ala Val Glu Thr Gly
35 40 45

Ala Thr Asn Pro Leu Val Pro Ser Asp Thr Val Gln Thr Arg His Val
50 55 60

Ile Gln Gln Arg Ser Arg Ser Glu Ser Thr Ile Glu Ser Phe Phe Ala
65 70 75 80

Arg Gly Ala Cys Val Ala Ile Ile Glu Val Asp Asn Glu Gln Pro Ala

```
                85                  90                  95

Thr Asn Val Gln Lys
            100


<210> SEQ ID NO 91
<211> LENGTH: 104
<212> TYPE: PRT
<213> ORGANISM: Coxsackievirus

<400> SEQUENCE: 91

Gly Ile Glu Glu Thr Ile Asp Thr Val Ile Ser Asn Ala Leu Gln Leu
1               5                   10                  15

Ser Gln Pro Lys Pro Gln Lys Gln Leu Thr Ala Gln Ser Thr Pro Ser
            20                  25                  30

Thr Ser Gly Val Asn Ser Gln Glu Val Pro Ala Leu Thr Ala Val Glu
        35                  40                  45

Thr Gly Val Ser Gly Gln Ala Ile Pro Ser Asp Val Ile Glu Thr Arg
    50                  55                  60

His Val Val Asn Tyr Lys Thr Arg Ser Glu Ser Thr Leu Glu Ser Phe
65                  70                  75                  80

Phe Gly Arg Ser Ala Cys Val Thr Met Leu Glu Val Glu Asn Phe Asn
                85                  90                  95

Ala Thr Thr Glu Ala Asp Lys Lys
            100


<210> SEQ ID NO 92
<211> LENGTH: 88
<212> TYPE: PRT
<213> ORGANISM: echovirus

<400> SEQUENCE: 92

Gly Asp Val Glu Glu Ala Val Asn Arg Ala Val Ala Arg Val Ala Asp
1               5                   10                  15

Thr Leu Pro Thr Gly Pro Arg Asn Ser Glu Ser Ile Pro Ala Leu Thr
            20                  25                  30

Ala Ala Glu Thr Gly His Thr Ser Gln Val Val Pro Gly Asp Thr Met
        35                  40                  45

Gln Thr Arg His Val Lys Asn Tyr His Ser Arg Thr Glu Ser Ser Val
    50                  55                  60

Glu Asn Phe Leu Cys Arg Ala Ala Cys Val Tyr Ile Thr Lys Tyr Lys
65                  70                  75                  80

Thr Lys Asp Ser Asp Pro Val Gln
                85


<210> SEQ ID NO 93
<211> LENGTH: 88
<212> TYPE: PRT
<213> ORGANISM: echovirus

<400> SEQUENCE: 93

Gly Asp Val Glu Glu Ala Ile Asp Arg Ala Val Ala Arg Val Ala Asp
1               5                   10                  15

Thr Met Pro Thr Gly Pro Arg Asn Thr Glu Ser Val Pro Ala Leu Thr
            20                  25                  30

Ala Val Glu Thr Gly His Thr Ser Gln Val Val Pro Gly Asp Thr Met
        35                  40                  45

Gln Thr Arg His Val Lys Asn Tyr His Ser Arg Thr Glu Ser Ser Ile
    50                  55                  60
```

Glu Asn Phe Leu Cys Arg Ala Ala Cys Val Tyr Ile Thr Thr Tyr Lys
65 70 75 80

Ser Ala Gly Gly Thr Pro Thr Glu
85

<210> SEQ ID NO 94
<211> LENGTH: 88
<212> TYPE: PRT
<213> ORGANISM: Coxsackievirus

<400> SEQUENCE: 94

Gly Asp Val Glu Glu Ala Ile Glu Arg Ala Arg Cys Thr Val Ala Asp
1 5 10 15

Thr Met Arg Thr Gly Pro Ser Asn Ser Ala Ser Val Pro Ala Leu Thr
20 25 30

Ala Val Glu Thr Gly His Thr Ser Gln Val Thr Pro Ser Asp Thr Met
35 40 45

Gln Thr Arg His Val Lys Asn Tyr His Ser Arg Ser Glu Ser Thr Val
50 55 60

Glu Asn Phe Leu Gly Arg Ser Ala Cys Val Tyr Met Glu Glu Tyr Lys
65 70 75 80

Thr Thr Asp Lys His Val Asn Lys
85

<210> SEQ ID NO 95
<211> LENGTH: 88
<212> TYPE: PRT
<213> ORGANISM: echovirus

<400> SEQUENCE: 95

Gly Asp Val Val Glu Ala Ile Glu Gly Ala Val Ala Arg Val Ala Asp
1 5 10 15

Thr Ile Ser Asn Gly Pro Thr Asn Ser Gln Ala Val Pro Ala Leu Thr
20 25 30

Ala Val Glu Thr Gly His Thr Ser Gln Val Val Pro Ser Asp Thr Met
35 40 45

Gln Thr Arg His Val Lys Asn Tyr His Ser Arg Ser Glu Ser Thr Ile
50 55 60

Glu Asn Phe Leu Ser Arg Ser Ala Cys Val Tyr Met Gly Glu Tyr Tyr
65 70 75 80

Thr Thr Asn Thr Asp Glu Thr Lys
85

<210> SEQ ID NO 96
<211> LENGTH: 88
<212> TYPE: PRT
<213> ORGANISM: echovirus

<400> SEQUENCE: 96

Gly Asp Val Val Lys Ala Ile Glu Gly Ala Val Ser Arg Val Ala Asp
1 5 10 15

Thr Ile Ser Ser Gly Pro Ser Asn Ser Gln Ala Val Pro Ala Leu Thr
20 25 30

Ala Val Glu Thr Gly His Thr Ser Gln Val Val Pro Ser Asp Thr Met
35 40 45

Gln Thr Arg His Val Lys Asn Tyr His Ser Arg Ser Glu Ser Ser Ile
50 55 60

```
Glu Asn Phe Leu Ser Arg Ser Ala Cys Val Tyr Met Gly Glu Tyr Lys
65                  70                  75                  80

Thr Lys Ala Ser Glu Glu Thr Lys
                85


<210> SEQ ID NO 97
<211> LENGTH: 88
<212> TYPE: PRT
<213> ORGANISM: echovirus

<400> SEQUENCE: 97

Gly Asp Thr Glu Thr Ala Ile Asp Asn Ala Ile Ala Arg Val Ala Asp
1               5                   10                  15

Thr Val Ala Ser Gly Pro Ser Asn Ser Thr Ser Ile Pro Ala Leu Thr
            20                  25                  30

Ala Val Glu Thr Gly His Thr Ser Gln Val Glu Pro Ser Asp Thr Met
        35                  40                  45

Gln Thr Arg His Val Lys Asn Tyr His Ser Arg Ser Glu Ser Thr Val
    50                  55                  60

Glu Asn Phe Leu Ser Arg Ser Ala Cys Val Tyr Ile Glu Glu Tyr Tyr
65                  70                  75                  80

Thr Lys Asp Gln Asp Asn Val Asn
                85


<210> SEQ ID NO 98
<211> LENGTH: 88
<212> TYPE: PRT
<213> ORGANISM: echovirus

<400> SEQUENCE: 98

Asn Asp Pro Ala Thr Ala Ile Glu Gly Ala Val Arg Arg Val Ala Asp
1               5                   10                  15

Thr Ile Gln Ser Gly Pro Ser Asn Ser Glu Arg Val Pro Ala Leu Thr
            20                  25                  30

Ala Val Glu Thr Gly His Thr Ala Gln Val Thr Pro Ser Asp Thr Met
        35                  40                  45

Gln Thr Arg His Val His Asn Phe His Thr Arg Ser Glu Ser Ser Ile
    50                  55                  60

Glu Asn Phe Leu Ser Arg Ala Ala Cys Val Tyr Ile Gly Lys Tyr Ser
65                  70                  75                  80

Ser Asn Ala Thr Thr Gln Asp Glu
                85


<210> SEQ ID NO 99
<211> LENGTH: 86
<212> TYPE: PRT
<213> ORGANISM: Coxsackievirus

<400> SEQUENCE: 99

Gly Pro Val Glu Glu Ser Val Glu Arg Ala Met Val Arg Val Ala Asp
1               5                   10                  15

Thr Val Ser Ser Lys Pro Thr Asn Ser Glu Ser Ile Pro Ala Leu Thr
            20                  25                  30

Ala Ala Glu Thr Gly His Thr Ser Gln Val Val Pro Ser Asp Thr Met
        35                  40                  45

Gln Thr Arg His Val Lys Asn Tyr His Ser Arg Ser Glu Ser Ser Ile
    50                  55                  60

Glu Asn Phe Leu Cys Arg Ser Ala Cys Val Tyr Tyr Ala Thr Tyr Asn
```

```
65                  70                  75                  80

Asn Asn Ser Glu Lys Gly
                85


<210> SEQ ID NO 100
<211> LENGTH: 86
<212> TYPE: PRT
<213> ORGANISM: Coxsackievirus

<400> SEQUENCE: 100

Gly Pro Val Glu Asp Ala Ile Thr Ala Ala Ile Gly Arg Val Ala Asp
1               5                   10                  15

Thr Val Gly Thr Gly Pro Thr Asn Ser Glu Ala Ile Pro Ala Leu Thr
            20                  25                  30

Ala Ala Glu Thr Gly His Thr Ser Gln Val Val Pro Gly Asp Thr Met
        35                  40                  45

Gln Thr Arg His Val Lys Asn Tyr His Ser Arg Ser Glu Ser Thr Ile
    50                  55                  60

Glu Asn Phe Leu Cys Arg Ser Ala Cys Val Tyr Phe Thr Glu Tyr Lys
65                  70                  75                  80

Asn Ser Gly Ala Lys Arg
                85


<210> SEQ ID NO 101
<211> LENGTH: 87
<212> TYPE: PRT
<213> ORGANISM: Coxsackievirus

<400> SEQUENCE: 101

Gly Pro Pro Gly Glu Ala Val Glu Arg Ala Ile Ala Arg Val Ala Asp
1               5                   10                  15

Thr Ile Ser Ser Gly Pro Val Asn Ser Glu Ser Ile Pro Ala Leu Thr
            20                  25                  30

Ala Ala Glu Thr Gly His Thr Ser Gln Val Val Pro Ala Asp Thr Met
        35                  40                  45

Gln Thr Arg His Val Lys Asn Tyr His Ser Arg Ser Glu Ser Thr Val
    50                  55                  60

Glu Asn Phe Leu Cys Arg Ser Ala Cys Val Tyr Tyr Thr Thr Tyr Lys
65                  70                  75                  80

Asn His Gly Thr Asp Gly Asp
                85


<210> SEQ ID NO 102
<211> LENGTH: 87
<212> TYPE: PRT
<213> ORGANISM: Coxsackievirus

<400> SEQUENCE: 102

Ser Pro Val Glu Gly Ala Ile Glu Arg Ala Ile Ala Arg Val Ala Asp
1               5                   10                  15

Thr Met Pro Ser Gly Pro Thr Asn Ser Glu Ala Val Pro Ala Leu Thr
            20                  25                  30

Ala Val Glu Thr Gly His Thr Ser Gln Val Val Pro Ser Asp Asn Met
        35                  40                  45

Gln Thr Arg His Val Lys Asn Tyr His Ser Arg Ser Glu Thr Ser Val
    50                  55                  60

Glu Asn Phe Leu Cys Arg Ser Ala Cys Val Tyr Phe Thr Thr Tyr Lys
65                  70                  75                  80
```

```
Asn Gln Thr Gly Ala Thr Asn
                85


<210> SEQ ID NO 103
<211> LENGTH: 89
<212> TYPE: PRT
<213> ORGANISM: Coxsackievirus

<400> SEQUENCE: 103

Ser Pro Val Glu Glu Ser Ile Glu Arg Ser Ile Gly Arg Val Ala Asp
1               5                   10                  15

Thr Ile Gly Ser Gly Pro Ser Asn Ser Glu Ala Ile Pro Val Leu Thr
            20                  25                  30

Ala Val Glu Thr Gly His Thr Ser Gln Val Thr Pro Ser Asp Thr Met
        35                  40                  45

Gln Thr Arg His Val His Asn Tyr His Ser Arg Ser Glu Ser Ser Val
    50                  55                  60

Glu Asn Phe Leu Ala Arg Ser Ala Cys Val Phe Tyr Thr Thr Tyr Thr
65                  70                  75                  80

Asn Ser Lys Asn Ala Ala Lys Glu Lys
                85


<210> SEQ ID NO 104
<211> LENGTH: 88
<212> TYPE: PRT
<213> ORGANISM: Coxsackievirus

<400> SEQUENCE: 104

Gly Pro Thr Glu Glu Ser Val Glu Arg Ala Met Gly Arg Val Ala Asp
1               5                   10                  15

Thr Ile Ala Arg Gly Pro Ser Asn Ser Glu Gln Ile Pro Ala Leu Thr
            20                  25                  30

Ala Val Glu Thr Gly His Thr Ser Gln Val Asp Pro Ser Asp Thr Met
        35                  40                  45

Gln Thr Arg His Val His Asn Tyr His Ser Arg Ser Glu Ser Ser Ile
    50                  55                  60

Glu Asn Phe Leu Cys Arg Ser Ala Cys Val Ile Tyr Ile Lys Tyr Ser
65                  70                  75                  80

Ser Ala Glu Ser Asn Asn Leu Lys
                85


<210> SEQ ID NO 105
<211> LENGTH: 83
<212> TYPE: PRT
<213> ORGANISM: echovirus

<400> SEQUENCE: 105

Gly Asp Lys Ala Ser Glu Val Thr Val Ser Asp Thr Gln Pro Ser Gly
1               5                   10                  15

Pro Ser Asn Ser Val Ser Ile Pro Met Leu Thr Ala Ala Glu Thr Gly
            20                  25                  30

His Thr Ser Gln Ala Val Pro Ser Asp Thr Ile Gln Thr Arg Cys Val
        35                  40                  45

Leu Asn Arg His Lys Arg Ser Glu Ser Ser Ile Glu Asn Phe Leu Cys
    50                  55                  60

Arg Ser Ala Cys Val Tyr Tyr Thr Thr Tyr Asp Thr His Gly Asp Ala
65                  70                  75                  80
```

Ala Asp Ala

<210> SEQ ID NO 106
<211> LENGTH: 83
<212> TYPE: PRT
<213> ORGANISM: Enterovirus 69

<400> SEQUENCE: 106

```
Asn Asp Gln His Asn Gly Ala Ile Val Ala Asn Thr Thr Ala Ser Gly
1               5                   10                  15

Pro Ser Asn Ser Glu Ser Ile Pro Ala Leu Thr Ala Ala Glu Thr Gly
            20                  25                  30

His Thr Ser Gln Val Val Pro Ser Asp Thr Ile Gln Thr Arg His Val
        35                  40                  45

Lys Asn Tyr His Ser Arg Ser Glu Ser Thr Ile Glu Asn Phe Leu Cys
    50                  55                  60

Arg Ser Ala Cys Val Tyr Tyr Thr Thr Tyr Asn Thr Gln Gly Glu Gln
65                  70                  75                  80

Ala His Asp
```

<210> SEQ ID NO 107
<211> LENGTH: 89
<212> TYPE: PRT
<213> ORGANISM: echovirus

<400> SEQUENCE: 107

```
Asn Asp Pro Ala Gln Ala Val Leu Ser Ala Ile Gly Arg Val Ala Asp
1               5                   10                  15

Thr Val Ala Ser Gly Pro Ser Asn Ser Glu Arg Val Pro Val Leu Thr
            20                  25                  30

Ala Ala Glu Thr Gly His Thr Ser Gln Val Val Pro Ser Asp Thr Ile
        35                  40                  45

Gln Thr Arg His Val Val Asn Phe His Thr Arg Ser Glu Ser Thr Ile
    50                  55                  60

Glu Asn Phe Met Cys Arg Ser Ala Cys Val Tyr Ile Ala Arg Tyr Gly
65                  70                  75                  80

Thr Glu Lys Gln Gly Glu Gln Ile Ser
                85
```

<210> SEQ ID NO 108
<211> LENGTH: 89
<212> TYPE: PRT
<213> ORGANISM: echovirus

<400> SEQUENCE: 108

```
Asn Asp Pro Glu Ser Ala Leu Asn Arg Ala Val Gly Arg Val Ala Asp
1               5                   10                  15

Thr Ile Ala Ser Gly Pro Val Asn Thr Glu Gln Ile Pro Ala Leu Thr
            20                  25                  30

Ala Val Glu Thr Gly His Thr Ser Gln Val Val Pro Ser Asp Thr Met
        35                  40                  45

Gln Thr Arg His Val Val Asn Tyr His Thr Arg Ser Glu Ser Ser Ile
    50                  55                  60

Glu Asn Phe Met Gly Arg Ala Ala Cys Val Tyr Ile Ala Gln Tyr Ala
65                  70                  75                  80

Thr Glu Lys Val Asn Asp Glu Leu Asp
                85
```

<210> SEQ ID NO 109
<211> LENGTH: 88
<212> TYPE: PRT
<213> ORGANISM: echovirus

<400> SEQUENCE: 109

Asn Asp Pro Ala Thr Ala Ile Val Arg Ser Val Glu Arg Val Ala Asp
1 5 10 15

Thr Ile Ala Ser Gly Pro Met Asn Ser Glu Arg Val Pro Ala Leu Thr
20 25 30

Ala Val Glu Thr Gly His Thr Ser Gln Val Val Pro Ser Asp Thr Met
35 40 45

Gln Thr Arg His Val Val Asn His His Ile Arg Ser Glu Ser Ser Ile
50 55 60

Glu Asn Phe Leu Ser Arg Ser Ala Cys Val Tyr Ile Asp Val Tyr Gly
65 70 75 80

Thr Lys Glu Asn Gly Asp Ile Lys
85

<210> SEQ ID NO 110
<211> LENGTH: 88
<212> TYPE: PRT
<213> ORGANISM: echovirus

<400> SEQUENCE: 110

Asn Glu Pro Ser Ser Ala Ile Glu Arg Ala Ile Val Arg Val Ala Asp
1 5 10 15

Thr Met Ala Ser Gly Pro Ala Asn Ser Glu Gln Ile Pro Ala Leu Thr
20 25 30

Ala Ala Glu Thr Gly His Thr Ser Gln Val Val Pro Ser Asp Thr Met
35 40 45

Gln Thr Arg His Val Cys Asn Tyr His Thr Arg Ser Glu Ser Ser Ile
50 55 60

Glu Asn Phe Leu Cys Arg Ala Ala Cys Val Tyr Ile Val Ser Tyr Lys
65 70 75 80

Thr Gln Gly Asp Glu Gln Thr Asp
85

<210> SEQ ID NO 111
<211> LENGTH: 88
<212> TYPE: PRT
<213> ORGANISM: echovirus

<400> SEQUENCE: 111

Asn Asp Val Gln Asn Ala Val Glu Arg Ser Ile Val Arg Val Ala Asp
1 5 10 15

Thr Leu Pro Ser Gly Pro Ser Asn Ser Glu Ser Ile Pro Ala Leu Thr
20 25 30

Ala Ala Glu Thr Gly His Thr Ser Gln Val Val Pro Ser Asp Thr Ile
35 40 45

Gln Thr Arg His Val Arg Asn Phe His Val Arg Ser Glu Ser Ser Val
50 55 60

Glu Asn Phe Leu Ser Arg Ser Ala Cys Val Tyr Ile Val Glu Tyr Lys
65 70 75 80

Thr Gln Asp Thr Thr Pro Asp Lys
85

<210> SEQ ID NO 112
<211> LENGTH: 88
<212> TYPE: PRT
<213> ORGANISM: echovirus

<400> SEQUENCE: 112

```
Gly Asp Val His Asp Ala Val Val Gly Ala Met Thr Arg Val Ala Asp
1               5                   10                  15

Thr Ile Ser Ser Gly Pro Ser Asn Ser Glu Ser Val Pro Ala Leu Thr
            20                  25                  30

Ala Ala Glu Thr Gly His Thr Ser Gln Val Val Pro Ser Asp Thr Met
        35                  40                  45

Gln Thr Arg His Val Arg Asn Phe His Thr Arg Ser Glu Ser Ser Ile
    50                  55                  60

Glu Asn Phe Met Ser Arg Ser Ala Cys Val Tyr Tyr Thr Lys Tyr Lys
65                  70                  75                  80

Thr Lys Asp Pro Asp Pro Thr Glu
                85
```

<210> SEQ ID NO 113
<211> LENGTH: 88
<212> TYPE: PRT
<213> ORGANISM: echovirus

<400> SEQUENCE: 113

```
Gly Asp Val Cys Glu Glu Val Glu Arg Ala Ile Thr Arg Val Ala Asp
1               5                   10                  15

Thr Val Gly Arg Gly Pro Ala Asn Thr Glu Ser Val Pro Ala Leu Thr
            20                  25                  30

Ala Val Glu Thr Gly His Thr Ser Gln Val Val Pro Gly Asp Thr Met
        35                  40                  45

Gln Thr Arg His Val Lys Asn Phe His Thr Arg Ser Glu Ser Ser Val
    50                  55                  60

Glu Asn Phe Met Cys Arg Ala Ala Cys Val Tyr Tyr Val Asp Tyr His
65                  70                  75                  80

Thr Gln Asn Asp Ser Glu Asp Glu
                85
```

<210> SEQ ID NO 114
<211> LENGTH: 88
<212> TYPE: PRT
<213> ORGANISM: echovirus

<400> SEQUENCE: 114

```
Gly Asp Val Gln Asp Ala Val Thr Gly Ala Ile Val Arg Val Ala Asp
1               5                   10                  15

Thr Leu His Thr Gly Pro Thr Asn Asn Glu Ala Ile Pro Asn Leu Thr
            20                  25                  30

Ala Val Glu Thr Gly His Thr Ser Gln Val Thr Pro Gly Asp Thr Met
        35                  40                  45

Gln Thr Arg His Val Ile Asn Met His Thr Arg Ser Glu Ser Ser Ile
    50                  55                  60

Glu Asn Phe Leu Ala Arg Ala Ala Cys Val Tyr Tyr Leu Asn Tyr Gln
65                  70                  75                  80

Thr Gly Ser Gly Pro Gly Thr Gln
                85
```

<210> SEQ ID NO 115

<211> LENGTH: 88
<212> TYPE: PRT
<213> ORGANISM: echovirus

<400> SEQUENCE: 115

Gly Glu Pro Gly Lys Ala Ile Glu Ser Ala Ile Ser Arg Val Ala Asp
1 5 10 15

Thr Ile Ser Ser Gly Pro Thr Asn Ser Glu Gln Val Pro Ala Leu Thr
20 25 30

Ala Ala Glu Thr Gly His Thr Ser Gln Val Val Pro Gly Asp Thr Ile
35 40 45

Gln Thr Arg His Val Lys Asn Tyr His Ser Arg Ser Glu Ser Thr Ile
50 55 60

Glu Asn Phe Leu Cys Arg Ser Ala Cys Val His Ile Ala Arg Tyr Glu
65 70 75 80

Ala Gly Ala Asn Ala Asn Asn Glu
85

<210> SEQ ID NO 116
<211> LENGTH: 88
<212> TYPE: PRT
<213> ORGANISM: echovirus

<400> SEQUENCE: 116

Gly Asp Thr Glu His Ala Val Glu Ser Ala Ile Ser Arg Val Ala Asp
1 5 10 15

Thr Ile Ser Ser Gly Pro Ser Asn Thr Val Ala Ile Pro Ala Leu Thr
20 25 30

Ala Ala Glu Thr Gly His Thr Ser Gln Val Thr Pro Ser Asp Asn Leu
35 40 45

Gln Thr Arg His Val Lys Asn Tyr His Ser Arg Ser Glu Ser Thr Ile
50 55 60

Glu Asn Phe Leu Cys Arg Ser Ala Cys Val His Ile Ala Ser Tyr Asn
65 70 75 80

Ala Tyr Gly Asp Val Gly Ser Asp
85

<210> SEQ ID NO 117
<211> LENGTH: 88
<212> TYPE: PRT
<213> ORGANISM: echovirus

<400> SEQUENCE: 117

Asn Asp Pro Glu Gln Ala Ile Asp Arg Ala Leu Ala Arg Val Ala Asp
1 5 10 15

Thr Val Arg Ser Gly Pro Ser Asn Ser Glu Gln Ile Pro Ala Leu Thr
20 25 30

Ala Val Glu Thr Gly His Thr Ser Gln Val Val Pro Ser Asp Thr Met
35 40 45

Gln Thr Arg His Val Lys Asn Tyr His Ser Arg Ser Glu Ser Thr Ile
50 55 60

Glu Asn Phe Leu Cys Arg Ser Ala Cys Val His Ile Ala Thr Tyr Lys
65 70 75 80

Ala Lys Gly Gly Ala Gly Asp Val
85

<210> SEQ ID NO 118
<211> LENGTH: 84

<212> TYPE: PRT
<213> ORGANISM: echovirus

<400> SEQUENCE: 118

Gly Asp Asp Gln His Lys Thr Asn Thr Val Thr Asp Thr Glu Gln Ser
1               5                   10                  15

Gly Pro Ser Asn Ser Glu Arg Val Pro Ala Leu Thr Ala Val Glu Thr
            20                  25                  30

Gly His Thr Ser Gln Val Val Pro Ser Asp Thr Val Gln Thr Arg His
        35                  40                  45

Val Arg Asn Tyr His Ser Arg Thr Glu Ser Thr Leu Glu Asn Phe Leu
    50                  55                  60

Gly Arg Ser Ala Cys Val His Ile Asp Thr Tyr Lys Ala Lys Gly Glu
65                  70                  75                  80

Lys Gly Ser Ser

<210> SEQ ID NO 119
<211> LENGTH: 84
<212> TYPE: PRT
<213> ORGANISM: echovirus

<400> SEQUENCE: 119

Gly Asp Glu Val Lys His Glu Pro Thr Val Ala Asn Thr Thr Ala Ser
1               5                   10                  15

Gly Pro Ser Asn Ser Gln Gln Val Pro Ala Leu Thr Ala Val Glu Thr
            20                  25                  30

Gly His Thr Ser Gln Val Val Pro Ser Asp Thr Ile Gln Thr Arg His
        35                  40                  45

Val His Asn Tyr His Ser Arg Thr Glu Ser Thr Leu Glu Asn Phe Leu
    50                  55                  60

Gly Arg Ser Ala Cys Val His Ile Asp Ser Tyr Lys Thr Lys Gly Val
65                  70                  75                  80

Thr Gly Glu Ser

<210> SEQ ID NO 120
<211> LENGTH: 82
<212> TYPE: PRT
<213> ORGANISM: echovirus

<400> SEQUENCE: 120

Gly Asp Asn Gln Asp Arg Thr Val Ala Asn Thr Gln Pro Ser Gly Pro
1               5                   10                  15

Ser Asn Ser Thr Glu Ile Pro Ala Leu Thr Ala Val Glu Thr Gly His
            20                  25                  30

Thr Ser Gln Val Asp Pro Ser Asp Thr Ile Gln Thr Arg His Val Val
        35                  40                  45

Asn Phe His Ser Arg Ser Glu Ser Thr Ile Glu Asn Phe Met Gly Arg
    50                  55                  60

Ala Ala Cys Val Phe Met Asp Gln Tyr Lys Ile Asn Gly Glu Glu Thr
65                  70                  75                  80

Ser Thr

<210> SEQ ID NO 121
<211> LENGTH: 88
<212> TYPE: PRT
<213> ORGANISM: echovirus

<400> SEQUENCE: 121

```
Gly Asp Val Glu Asp Ser Val Asn Arg Ala Val Val Arg Val Ala Asp
1               5                   10                  15

Thr Met Pro Ser Gly Pro Ser Asn Ser Gln Ala Val Pro Ala Leu Thr
            20                  25                  30

Ala Ala Glu Thr Gly His Thr Ser Gln Val Val Pro Gly Asp Asn Ile
        35                  40                  45

Gln Thr Arg His Val His Asn Tyr His Ser Arg Thr Glu Ser Ser Ile
    50                  55                  60

Glu Asn Phe Phe Gly Arg Ser Ala Cys Val Val Val Lys Thr Tyr Lys
65                  70                  75                  80

Met Gly Gln Lys Val Val Ala Thr
                85


<210> SEQ ID NO 122
<211> LENGTH: 81
<212> TYPE: PRT
<213> ORGANISM: echovirus

<400> SEQUENCE: 122

Gly Asp Asp Ala Arg Thr Val Ser Asn Thr Gln Lys Ser Gln Pro Ser
1               5                   10                  15

Asn Ser Glu Gln Val Pro Ala Leu Thr Ala Val Glu Thr Gly His Thr
            20                  25                  30

Ser Gln Val Glu Pro Ser Asp Thr Val Gln Thr Arg His Val Val Asn
        35                  40                  45

Ser His Ser Arg Thr Glu Ser Thr Ile Glu Asn Phe Phe Gly Arg Ala
    50                  55                  60

Ala Cys Val Arg Val Arg Glu Tyr Ser Ile Gly His Asp Leu Ala Ala
65                  70                  75                  80

Asp


<210> SEQ ID NO 123
<211> LENGTH: 88
<212> TYPE: PRT
<213> ORGANISM: echovirus

<400> SEQUENCE: 123

Gly Asp Asp Pro Pro His Ser Ile Ser Asn Thr Val Ala Asn Thr Asn
1               5                   10                  15

Pro Ser Gly Pro Thr Asn Ser Glu Arg Ile Pro Ala Leu Thr Ala Ala
            20                  25                  30

Glu Thr Gly His Thr Ser Gln Val Val Pro Ser Asp Thr Val Gln Thr
        35                  40                  45

Arg Cys Val Lys Asn Phe His Thr Arg Ser Glu Ser Ser Ile Glu Asn
    50                  55                  60

Phe Leu Cys Arg Ser Ala Cys Ala His Met Ser Ser Tyr Glu Ala Phe
65                  70                  75                  80

Pro Thr Thr Thr Gln Asp Gly Thr
                85


<210> SEQ ID NO 124
<211> LENGTH: 89
<212> TYPE: PRT
<213> ORGANISM: echovirus

<400> SEQUENCE: 124

Gly Asp Val Gln Asn Ala Val Glu Gly Ala Met Val Arg Val Ala Asp
```

-continued

```
1               5                   10                  15

Thr Val Ser Thr Ser Ala Thr Asn Ser Glu Gln Val Pro Asn Leu Thr
            20                  25                  30

Ala Val Glu Thr Gly His Thr Ser Gln Val Val Pro Gly Asp Thr Met
        35                  40                  45

Gln Thr Arg His Val Val Asn Lys His Val Arg Ser Glu Ser Thr Ile
    50                  55                  60

Glu Asn Phe Leu Ala Arg Ser Ala Cys Val Tyr Phe Leu Glu Tyr Glu
65                  70                  75                  80

Thr Gly Thr Lys Thr Asp Ser Asn Ala
                85


<210> SEQ ID NO 125
<211> LENGTH: 69
<212> TYPE: PRT
<213> ORGANISM: Human rhinovirus

<400> SEQUENCE: 125

Met Gly Ala Gln Val Ser Thr Gln Lys Ser Gly Ser His Glu Asn Gln
1               5                   10                  15

Asn Ile Leu Thr Asn Gly Ser Asn Gln Thr Phe Thr Val Ile Asn Tyr
            20                  25                  30

Tyr Lys Asp Ala Ala Ser Thr Ser Ser Ala Gly Gln Ser Leu Ser Met
        35                  40                  45

Asp Pro Ser Lys Phe Thr Glu Pro Val Lys Asp Leu Met Leu Lys Gly
    50                  55                  60

Ala Pro Ala Leu Asn
65


<210> SEQ ID NO 126
<211> LENGTH: 69
<212> TYPE: PRT
<213> ORGANISM: Human rhinovirus

<400> SEQUENCE: 126

Met Gly Ala Gln Val Ser Arg Gln Asn Val Gly Thr His Ser Thr Gln
1               5                   10                  15

Asn Thr Val Ser Asn Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln
65


<210> SEQ ID NO 127
<211> LENGTH: 69
<212> TYPE: PRT
<213> ORGANISM: Human rhinovirus

<400> SEQUENCE: 127

Met Gly Ala Gln Val Ser Arg Gln Asn Val Gly Thr His Ser Thr Gln
1               5                   10                  15

Asn Ser Val Ser Asn Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45
```

Asp Pro Ser Lys Phe Thr Asp Pro Val Lys Asp Val Leu Glu Lys Gly
    50                  55                  60

Ile Pro Thr Leu Gln
65

<210> SEQ ID NO 128
<211> LENGTH: 69
<212> TYPE: PRT
<213> ORGANISM: Human rhinovirus

<400> SEQUENCE: 128

Met Gly Ala Gln Val Ser Arg Gln Asn Val Gly Thr His Ser Thr Gln
1               5                   10                  15

Asn Ala Val Ser Gly Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Thr Lys Gly
    50                  55                  60

Ile Pro Thr Leu Gln
65

<210> SEQ ID NO 129
<211> LENGTH: 67
<212> TYPE: PRT
<213> ORGANISM: Human rhinovirus

<400> SEQUENCE: 129

Met Gly Ala Gln Val Ser Arg Gln Ser Val Gly Ser His Glu Thr Met
1               5                   10                  15

Ile His Ala Gly Thr Gly Ala Val Val Lys Tyr Phe Asn Val Asn Tyr
            20                  25                  30

Tyr Lys Asp Ala Ala Ser Ser Gly Leu Thr Lys Gln Asp Phe Ser Gln
        35                  40                  45

Asp Pro Ser Lys Phe Thr Gln Pro Val Ala Asp Ile Leu Ser Asn Pro
    50                  55                  60

Ala Leu Met
65

<210> SEQ ID NO 130
<211> LENGTH: 69
<212> TYPE: PRT
<213> ORGANISM: Coxsackievirus

<400> SEQUENCE: 130

Met Gly Ser Gln Val Ser Thr Gln Arg Ser Gly Ser His Glu Asn Ser
1               5                   10                  15

Asn Ser Ala Ser Glu Gly Ser Thr Ile Asn Tyr Thr Thr Ile Asn Tyr
            20                  25                  30

Tyr Lys Asp Ala Tyr Ala Ala Ser Ala Gly Arg Gln Asp Met Ser Gln
        35                  40                  45

Asp Pro Lys Lys Phe Thr Asp Pro Val Met Asp Val Ile His Glu Met
    50                  55                  60

Ala Pro Pro Leu Lys
65

<210> SEQ ID NO 131
<211> LENGTH: 69

<212> TYPE: PRT
<213> ORGANISM: Enterovirus 71

<400> SEQUENCE: 131

Met Gly Ser Gln Val Ser Thr Gln Arg Ser Gly Ser His Glu Asn Ser
1               5                   10                  15

Asn Ser Ala Thr Glu Gly Ser Thr Ile Asn Tyr Thr Thr Ile Asn Tyr
            20                  25                  30

Tyr Lys Asp Ser Tyr Ala Ala Thr Ala Gly Lys Gln Ser Leu Lys Gln
        35                  40                  45

Asp Pro Asp Lys Phe Ala Asn Pro Val Lys Asp Ile Phe Thr Glu Met
    50                  55                  60

Ala Ala Pro Leu Lys
65

<210> SEQ ID NO 132
<211> LENGTH: 69
<212> TYPE: PRT
<213> ORGANISM: Enterovirus 68

<400> SEQUENCE: 132

Met Gly Ala Gln Val Thr Arg Gln Gln Thr Gly Thr His Glu Asn Ala
1               5                   10                  15

Asn Ile Ala Thr Asn Gly Ser His Ile Thr Tyr Asn Gln Ile Asn Phe
            20                  25                  30

Tyr Lys Asp Ser Tyr Ala Ala Ser Ala Ser Lys Gln Asp Phe Ser Gln
        35                  40                  45

Asp Pro Ser Lys Phe Thr Glu Pro Val Val Glu Gly Leu Lys Ala Gly
    50                  55                  60

Ala Pro Val Leu Lys
65

<210> SEQ ID NO 133
<211> LENGTH: 69
<212> TYPE: PRT
<213> ORGANISM: Enterovirus 70

<400> SEQUENCE: 133

Met Gly Ala Gln Val Ser Arg Gln Gln Thr Gly Thr His Glu Asn Ala
1               5                   10                  15

Asn Val Ala Thr Gly Gly Ser Ser Ile Thr Tyr Asn Gln Ile Asn Phe
            20                  25                  30

Tyr Lys Asp Ser Tyr Ala Ala Ser Ala Ser Lys Gln Asp Phe Ser Gln
        35                  40                  45

Asp Pro Ser Lys Phe Thr Glu Pro Val Ala Glu Ala Leu Lys Ala Gly
    50                  55                  60

Ala Pro Val Leu Lys
65

<210> SEQ ID NO 134
<211> LENGTH: 69
<212> TYPE: PRT
<213> ORGANISM: poliovirus

<400> SEQUENCE: 134

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

```
Tyr Arg Asp Ser Ala Ser Asn Ala Ala Ser Lys Gln Asp Phe Ser Gln
        35                  40                  45

Asp Pro Ser Lys Phe Thr Glu Pro Ile Lys Asp Val Leu Ile Lys Thr
    50                  55                  60

Ala Pro Met Leu Asn
65
```

<210> SEQ ID NO 135
<211> LENGTH: 69
<212> TYPE: PRT
<213> ORGANISM: poliovirus

<400> SEQUENCE: 135

```
Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ala Gln
        35                  40                  45

Asp Pro Ser Lys Phe Thr Glu Pro Ile Lys Asp Val Leu Ile Lys Thr
    50                  55                  60

Ala Pro Thr Leu Asn
65
```

<210> SEQ ID NO 136
<211> LENGTH: 69
<212> TYPE: PRT
<213> ORGANISM: poliovirus

<400> SEQUENCE: 136

```
Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Lys Asp Ser Ala Ser Asn Ala Ala Ser Lys Gln Asp Tyr Ser Gln
        35                  40                  45

Asp Pro Ser Lys Phe Thr Glu Pro Leu Lys Asp Val Leu Ile Lys Thr
    50                  55                  60

Ala Pro Ala Leu Asn
65
```

<210> SEQ ID NO 137
<211> LENGTH: 69
<212> TYPE: PRT
<213> ORGANISM: Coxsackievirus

<400> SEQUENCE: 137

```
Met Gly Ala Gln Val Ser Ser Gln Lys Val Gly Ala His Glu Asn Thr
1               5                   10                  15

Asn Val Ala Thr Gly Gly Ser Thr Val Asn Tyr Thr Thr Ile Asn Tyr
            20                  25                  30

Tyr Lys Asp Ser Ala Ser Asn Ala Ala Ser Lys Leu Asp Phe Ser Gln
        35                  40                  45

Asp Pro Ser Lys Phe Thr Glu Pro Val Lys Asp Ile Met Leu Lys Ser
    50                  55                  60

Ala Pro Ala Leu Asn
65
```

<210> SEQ ID NO 138
<211> LENGTH: 69
<212> TYPE: PRT
<213> ORGANISM: echovirus

<400> SEQUENCE: 138

Met Gly Ala Gln Val Ser Thr Gln Lys Thr Gly Ala His Glu Thr Gly
1 5 10 15

Leu Ser Ala Ser Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Gly Lys Tyr Thr Glu Pro Val Lys Asp Ile Met Ile Lys Ser
50 55 60

Met Pro Ala Leu Asn
65

<210> SEQ ID NO 139
<211> LENGTH: 69
<212> TYPE: PRT
<213> ORGANISM: echovirus

<400> SEQUENCE: 139

Met Gly Ala Gln Val Ser Thr Gln Lys Thr Gly Ala His Glu Thr Gly
1 5 10 15

Leu Thr Ala Ser Gly Asn Ser Thr Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Ser Lys Phe Thr Glu Pro Met Lys Asp Val Met Ile Lys Ser
50 55 60

Leu Pro Ala Leu Asn
65

<210> SEQ ID NO 140
<211> LENGTH: 69
<212> TYPE: PRT
<213> ORGANISM: Coxsackievirus

<400> SEQUENCE: 140

Met Gly Ala Gln Val Ser Thr Gln Lys Thr Gly Ala His Glu Thr Ser
1 5 10 15

Leu Ser Ala Ala Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Ser Lys Phe Thr Glu Pro Val Lys Asp Val Met Ile Lys Ser
50 55 60

Leu Pro Ala Leu Asn
65

<210> SEQ ID NO 141
<211> LENGTH: 69
<212> TYPE: PRT
<213> ORGANISM: echovirus

<400> SEQUENCE: 141

Met Gly Ala Gln Val Ser Thr Gln Lys Thr Gly Ala His Glu Thr Gly
1 5 10 15

```
Leu Asn Ala Ser Gly Ser Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60

Met Pro Ala Leu Asn
65


<210> SEQ ID NO 142
<211> LENGTH: 69
<212> TYPE: PRT
<213> ORGANISM: echovirus

<400> SEQUENCE: 142

Met Gly Ala Gln Val Ser Thr Gln Lys Thr Gly Ala His Glu Thr Gly
1               5                   10                  15

Leu Asn Ala Ser Gly Asn Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60

Met Pro Ala Leu Asn
65


<210> SEQ ID NO 143
<211> LENGTH: 69
<212> TYPE: PRT
<213> ORGANISM: echovirus

<400> SEQUENCE: 143

Met Gly Ala Gln Val Ser Thr Gln Lys Thr Gly Ala His Glu Thr Gly
1               5                   10                  15

Leu Asn Ala Ser Gly Asn Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Thr
    50                  55                  60

Met Pro Ala Leu Asn
65


<210> SEQ ID NO 144
<211> LENGTH: 69
<212> TYPE: PRT
<213> ORGANISM: echovirus

<400> SEQUENCE: 144

Met Gly Ala Gln Val Ser Thr Gln Lys Thr Gly Ala His Glu Thr Gly
1               5                   10                  15

Leu Ser Ala Ser Gly Ser Ser Ile Ile His Tyr Thr Asn Ile Asn Tyr
            20                  25                  30

Tyr Lys Asp Ala Ala Ser Asn Ser Ala Asn Arg Gln Asp Phe Ser Gln
        35                  40                  45

Asp Pro Ser Lys Phe Thr Glu Pro Val Lys Asp Ile Met Ile Lys Ser
    50                  55                  60
```

Met Pro Ala Leu Asn
65

<210> SEQ ID NO 145
<211> LENGTH: 69
<212> TYPE: PRT
<213> ORGANISM: Coxsackievirus

<400> SEQUENCE: 145

Met Gly Ala Gln Val Ser Thr Gln Lys Thr Gly Ala His Glu Thr Arg
1 5 10 15

Leu Asn Ala Ser Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Gly Lys Phe Thr Glu Pro Val Lys Asp Ile Met Ile Lys Ser
50 55 60

Leu Pro Ala Leu Asn
65

<210> SEQ ID NO 146
<211> LENGTH: 69
<212> TYPE: PRT
<213> ORGANISM: Coxsackievirus

<400> SEQUENCE: 146

Met Gly Ala Gln Val Ser Thr Gln Lys Thr Gly Ala His Glu Thr Gly
1 5 10 15

Leu Arg Ala Ser Gly Asn Ser Ile Ile His Tyr Thr Asn Ile Asn Tyr
20 25 30

Tyr Lys Asp Ala Ala Ser Asn Ser Ala Asn Arg Gln Glu Phe Ala Gln
35 40 45

Asp Pro Gly Lys Phe Thr Glu Pro Val Lys Asp Ile Met Ile Lys Ser
50 55 60

Met Pro Ala Leu Asn
65

<210> SEQ ID NO 147
<211> LENGTH: 69
<212> TYPE: PRT
<213> ORGANISM: Coxsackievirus

<400> SEQUENCE: 147

Met Gly Ala Gln Val Ser Thr Gln Lys Thr Gly Ala His Glu Thr Ala
1 5 10 15

Leu Asn Ala Gln Gly Asn Ser Val Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Ser Lys Phe Thr Glu Pro Val Lys Asp Val Met Ile Lys Ser
50 55 60

Leu Pro Ala Leu Asn
65

<210> SEQ ID NO 148
<211> LENGTH: 69
<212> TYPE: PRT
<213> ORGANISM: Coxsackievirus

<400> SEQUENCE: 148

Met Gly Ala Gln Val Ser Thr Gln Lys Thr Gly Ala His Glu Thr Gly
1 5 10 15

Leu Ser Ala Ser Gly Gly Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Gly Lys Phe Thr Glu Pro Val Lys Asp Ile Met Ile Lys Ser
50 55 60

Met Pro Ala Leu Asn
65

<210> SEQ ID NO 149
<211> LENGTH: 69
<212> TYPE: PRT
<213> ORGANISM: Coxsackievirus

<400> SEQUENCE: 149

Met Gly Ala Gln Val Ser Thr Gln Lys Thr Gly Ala His Glu Thr Ser
1 5 10 15

Leu Ser Ala Thr Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Ser Lys Phe Thr Glu Pro Val Lys Asp Val Met Ile Lys Ser
50 55 60

Leu Pro Ala Leu Asn
65

<210> SEQ ID NO 150
<211> LENGTH: 69
<212> TYPE: PRT
<213> ORGANISM: echovirus

<400> SEQUENCE: 150

Met Gly Ala Gln Val Ser Thr Gln Lys Thr Gly Ala His Glu Thr Gly
1 5 10 15

Leu Asn Ala Ser Gly Asn Ser Val Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Ser Lys Phe Ala Glu Pro Met Lys Asp Val Met Ile Lys Thr
50 55 60

Leu Pro Ala Leu Asn
65

<210> SEQ ID NO 151
<211> LENGTH: 69
<212> TYPE: PRT
<213> ORGANISM: Enterovirus 69

<400> SEQUENCE: 151

Met Gly Ala Gln Val Ser Thr Gln Lys Thr Gly Ala His Glu Thr Gly
1 5 10 15

Leu Asn Ala Ser Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

```
Asp Pro Ser Lys Phe Ala Glu Pro Met Lys Asp Val Met Ile Lys Thr
    50                  55                  60

Leu Pro Ala Leu Asn
65


<210> SEQ ID NO 152
<211> LENGTH: 69
<212> TYPE: PRT
<213> ORGANISM: echovirus

<400> SEQUENCE: 152

Met Gly Ala Gln Val Ser Thr Gln Lys Thr Gly Ala His Glu Thr Ser
1               5                   10                  15

Leu Asn Ala Ser Gly Asn Ser Val Ile His Tyr Thr Asn Ile Asn Tyr
            20                  25                  30

Tyr Lys Asp Ser Ala Ser Asn Ser Ala Asn Arg Gln Asp Phe Thr Gln
        35                  40                  45

Asp Pro Ser Lys Phe Thr Glu Pro Val Lys Asp Val Met Ile Lys Ser
    50                  55                  60

Leu Pro Ala Leu Asn
65


<210> SEQ ID NO 153
<211> LENGTH: 69
<212> TYPE: PRT
<213> ORGANISM: echovirus

<400> SEQUENCE: 153

Met Gly Ala Gln Val Ser Thr Gln Lys Thr Gly Ala His Glu Thr Gly
1               5                   10                  15

Leu Asn Ala Ser Gly Asn Ser Thr Ile His Tyr Thr Asn Ile Asn Tyr
            20                  25                  30

Tyr Lys Asp Ser Ala Ser Asn Ser Leu Asn Arg Gln Asp Phe Thr Gln
        35                  40                  45

Asp Pro Ser Lys Phe Thr Glu Pro Val Lys Asp Val Met Val Lys Thr
    50                  55                  60

Leu Pro Ala Leu Asn
65


<210> SEQ ID NO 154
<211> LENGTH: 69
<212> TYPE: PRT
<213> ORGANISM: echovirus

<400> SEQUENCE: 154

Met Gly Ala Gln Val Ser Thr Gln Lys Thr Gly Ala His Glu Thr Gly
1               5                   10                  15

Leu Ser Ala Asn Gly Asn Ser Val Ile His Tyr Thr Asn Ile Asn Tyr
            20                  25                  30

Tyr Lys Asp Ala Ala Ser Asn Ser Ala Asn Arg Gln Asp Phe Ser Gln
        35                  40                  45

Asp Pro Ser Lys Phe Thr Glu Pro Met Lys Asp Val Met Ile Lys Ser
    50                  55                  60

Leu Pro Ala Leu Asn
65


<210> SEQ ID NO 155
<211> LENGTH: 69
<212> TYPE: PRT
```

<213> ORGANISM: echovirus

<400> SEQUENCE: 155

Met Gly Ala Gln Val Ser Thr Gln Lys Thr Gly Ala His Glu Thr Gly
1 5 10 15

Leu Asn Ala Ser Gly Asn Ser Ile Ile His Tyr Thr Asn Ile Asn Tyr
20 25 30

Tyr Lys Asp Ala Ala Ser Asn Ser Ala Asn Arg Gln Asp Phe Ser Gln
35 40 45

Asp Pro Ser Lys Phe Thr Glu Pro Val Lys Asp Val Met Ile Lys Thr
50 55 60

Leu Pro Ala Leu Asn
65

<210> SEQ ID NO 156
<211> LENGTH: 69
<212> TYPE: PRT
<213> ORGANISM: echovirus

<400> SEQUENCE: 156

Met Gly Ala Gln Val Ser Thr Gln Lys Thr Gly Ala His Glu Thr Gly
1 5 10 15

Leu Ser Ala Ser Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Gly Lys Phe Thr Glu Pro Val Lys Asp Ile Met Ala Lys Thr
50 55 60

Leu Pro Ala Leu Asn
65

<210> SEQ ID NO 157
<211> LENGTH: 69
<212> TYPE: PRT
<213> ORGANISM: echovirus

<400> SEQUENCE: 157

Met Gly Ala Gln Val Ser Thr Gln Lys Thr Gly Ala His Glu Thr Gly
1 5 10 15

Leu Asn Ala Ser Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Ser Lys Phe Thr Glu Pro Val Lys Asp Val Met Ile Lys Ser
50 55 60

Leu Pro Ala Leu Asn
65

<210> SEQ ID NO 158
<211> LENGTH: 69
<212> TYPE: PRT
<213> ORGANISM: echovirus

<400> SEQUENCE: 158

Met Gly Ala Gln Val Ser Thr Gln Lys Thr Gly Ala His Glu Thr Ser
1 5 10 15

Leu Ser Ala Ser Gly Asn Ser Ile Ile His Tyr Thr Asn Ile Asn Tyr
20 25 30

```
Tyr Lys Asp Ala Ala Ser Asn Ser Ala Asn Arg Gln Asp Phe Ser Gln
        35                  40                  45

Asp Pro Ser Lys Phe Thr Glu Pro Met Lys Asp Ile Met Val Lys Ser
    50                  55                  60

Leu Pro Ala Leu Asn
65


<210> SEQ ID NO 159
<211> LENGTH: 69
<212> TYPE: PRT
<213> ORGANISM: echovirus

<400> SEQUENCE: 159

Met Gly Ala Gln Val Ser Thr Gln Lys Thr Gly Ala His Glu Thr Gly
1               5                   10                  15

Leu Asn Ala Ser Gly Ser Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Ser Lys Phe Thr Glu Pro Val Lys Asp Ile Met Ile Lys Ser
    50                  55                  60

Leu Pro Ala Leu Asn
65


<210> SEQ ID NO 160
<211> LENGTH: 69
<212> TYPE: PRT
<213> ORGANISM: echovirus

<400> SEQUENCE: 160

Met Gly Ala Gln Val Ser Thr Gln Lys Thr Gly Ala His Glu Thr Leu
1               5                   10                  15

Leu Glu Ala Ala Gln Gly Ala Thr Ile Asn Tyr Thr Asn Ile Asn Tyr
            20                  25                  30

Tyr Lys Asp Ala Ala Ser Asn Ser Ala Asn Arg Gln Asp Phe Ser Gln
        35                  40                  45

Asp Pro Ser Lys Phe Thr Glu Pro Val Lys Asp Ile Met Ile Lys Ser
    50                  55                  60

Met Pro Ala Leu Asn
65


<210> SEQ ID NO 161
<211> LENGTH: 69
<212> TYPE: PRT
<213> ORGANISM: echovirus

<400> SEQUENCE: 161

Met Gly Ala Gln Val Ser Thr Gln Lys Thr Gly Ala His Glu Thr Leu
1               5                   10                  15

Leu Glu Ala Ala Gln Gly Ala Thr Ile Asn Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Leu Met Ile Lys Ser
    50                  55                  60

Met Pro Ala Leu Asn
65
```

<210> SEQ ID NO 162
<211> LENGTH: 69
<212> TYPE: PRT
<213> ORGANISM: echovirus

<400> SEQUENCE: 162

Met Gly Ala Gln Val Ser Thr Gln Lys Thr Gly Ala His Glu Thr Gly
1 5 10 15

Leu Asn Ala Gln Gly Asn Ser Val Ile His Tyr Thr Asn Ile Asn Tyr
20 25 30

Tyr Lys Asp Ala Ala Ser Asn Ser Ala Asn Arg Gln Asp Phe Gln Gln
35 40 45

Asp Pro Gly Lys Phe Thr Glu Pro Met Lys Asp Ile Met Ile Lys Ser
50 55 60

Leu Pro Ala Leu Asn
65

<210> SEQ ID NO 163
<211> LENGTH: 69
<212> TYPE: PRT
<213> ORGANISM: echovirus

<400> SEQUENCE: 163

Met Gly Ala Gln Val Ser Thr Gln Lys Thr Gly Ala His Glu Thr Ser
1 5 10 15

Leu Asn Thr Gly Asn Ser Ser Ile Ile His Tyr Thr Asn Ile Asn Tyr
20 25 30

Tyr Lys Asp Ala Ala Ser Asn Ser Ser Asn Arg Gln Asp Met Asp Gln
35 40 45

Asp Pro Ser Lys Phe Thr Glu Pro Val Met Asp Ile Met Val Lys Ser
50 55 60

Leu Pro Ala Leu Asn
65

<210> SEQ ID NO 164
<211> LENGTH: 69
<212> TYPE: PRT
<213> ORGANISM: echovirus

<400> SEQUENCE: 164

Met Gly Ala Gln Val Ser Ser Gln Lys Val Gly Ala His Glu Thr Lys
1 5 10 15

Leu Asn Thr Gly Asn Asn Ser Thr Ile Asn Tyr Thr Asn Ile Asn Tyr
20 25 30

Tyr Lys Asp Ala Ala Ser Asn Ser Ser Asn Arg Gln Thr Leu Glu Gln
35 40 45

Asp Pro Ser Lys Phe Thr Glu Pro Val Leu Asp Val Met Val Lys Ser
50 55 60

Leu Pro Ala Leu Asn
65

<210> SEQ ID NO 165
<211> LENGTH: 69
<212> TYPE: PRT
<213> ORGANISM: echovirus

<400> SEQUENCE: 165

Met Gly Ala Gln Val Ser Thr Gln Lys Thr Gly Ala His Glu Thr Ser
1 5 10 15

-continued

```
Leu Ser Ala Lys Gly Asn Ser Ile Ile His Tyr Thr Asn Ile Asn Phe
            20                  25                  30

Tyr Lys Asp Ala Ala Ser Ser Ala Ser Asn Arg Gln Asp Ile Gln Gln
        35                  40                  45

Asp Pro Gly Lys Phe Thr Asp Pro Val Lys Asp Leu Met Ile Lys Thr
    50                  55                  60

Leu Pro Ala Leu Asn
65
```

```
<210> SEQ ID NO 166
<211> LENGTH: 69
<212> TYPE: PRT
<213> ORGANISM: echovirus

<400> SEQUENCE: 166

Met Gly Ala Gln Val Ser Thr Gln Lys Thr Gly Ala His Glu Thr Gly
1               5                   10                  15

Leu Asn Ala Ser Gly Asn Ser Val Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Ser Lys Phe Thr Glu Pro Val Lys Asp Ile Met Ile Lys Ser
    50                  55                  60

Met Pro Ala Leu Asn
65
```

```
<210> SEQ ID NO 167
<211> LENGTH: 69
<212> TYPE: PRT
<213> ORGANISM: echovirus

<400> SEQUENCE: 167

Met Gly Ala Gln Val Ser Thr Gln Lys Thr Gly Ala His Glu Thr Ser
1               5                   10                  15

Val Asn Ala Thr Gly Ser Ser Ile Val His Tyr Thr Asn Ile Asn Phe
            20                  25                  30

Tyr Lys Asp Ala Ala Ser Asn Ser Ser Asn Arg Gln Asp Met Ser Gln
        35                  40                  45

Asp Pro Ala Lys Phe Thr Glu Pro Val Lys Asp Ile Met Leu Lys Ser
    50                  55                  60

Leu Pro Ala Leu Asn
65
```

```
<210> SEQ ID NO 168
<211> LENGTH: 69
<212> TYPE: PRT
<213> ORGANISM: echovirus

<400> SEQUENCE: 168

Met Gly Ala Gln Val Ser Thr Gln Lys Thr Gly Ala His Glu Thr Ser
1               5                   10                  15

Leu Asn Ala Ser Gly Ser Ser Val Ile His Tyr Thr Asn Ile Asn Phe
            20                  25                  30

Tyr Lys Asp Ala Ala Ser Asn Ser Ala Asn Arg Gln Asp Phe Ser Gln
        35                  40                  45

Asp Pro Ser Lys Phe Thr Glu Pro Leu Lys Asp Val Met Ile Lys Ser
    50                  55                  60

Leu Pro Ala Leu Asn
```

65

<210> SEQ ID NO 169
<211> LENGTH: 69
<212> TYPE: PRT
<213> ORGANISM: echovirus

<400> SEQUENCE: 169

Met Gly Ala Gln Val Ser Thr Gln Lys Thr Gly Ala His Glu Thr Gly
1 5 10 15

Leu Asn Ala Asn Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Gly Lys Phe Thr Glu Pro Val Lys Asp Val Met Ile Lys Thr
50 55 60

Leu Pro Ala Leu Asn
65

<210> SEQ ID NO 170
<211> LENGTH: 35
<212> TYPE: PRT
<213> ORGANISM: Human rhinovirus

<400> SEQUENCE: 170

Met Val Gly Ala Gln Val Ser Thr Gln Lys Ser Gly Ser His Glu Asn
1 5 10 15

Gln Asn Ile Leu Thr Asn Gly Ser Asn Gln Thr Phe Thr Val Ile Asn
20 25 30

Tyr Leu Met
35

<210> SEQ ID NO 171
<211> LENGTH: 206
<212> TYPE: DNA
<213> ORGANISM: Human rhinovirus

<400> SEQUENCE: 171
ctcactatag ggcgaattga aggaaggccg tcaaggccta ggcgcgccac catggttggt 60
gctcaagttt ccactcaaaa gtctggttcc cacgagaacc agaacatctt gactaacggt 120
tccaaccaga ctttcactgt tatcaactac ctcatgaatt aattaactgg cctcatgggc 180
cttcctttca ctgcccgctt tccagt 206

<210> SEQ ID NO 172
<211> LENGTH: 206
<212> TYPE: DNA
<213> ORGANISM: Human rhinovirus

<400> SEQUENCE: 172
gagtgatatc ccgcttaact tccttccggc agttccggat ccgcgcggtg gtaccaacca 60
cgagttcaaa ggtgagtttt cagaccaagg gtgctcttgg tcttgtagaa ctgattgcca 120
aggttggtct gaaagtgaca atagttgatg gagtacttaa ttaattgacc ggagtacccg 180
gaaggaaagt gacgggcgaa aggtca 206

<210> SEQ ID NO 173
<211> LENGTH: 12
<212> TYPE: DNA
<213> ORGANISM: Pichia pastoris

<400> SEQUENCE: 173
ttcgaaacga tg 12

<210> SEQ ID NO 174
<211> LENGTH: 20
<212> TYPE: DNA
<213> ORGANISM: Artificial Sequence
<220> FEATURE:
<223> OTHER INFORMATION: EcoRI Cloning site

<400> SEQUENCE: 174
ttcgaaacga ggaattcatg 20

<210> SEQ ID NO 175
<211> LENGTH: 58
<212> TYPE: DNA
<213> ORGANISM: artificial
<220> FEATURE:
<223> OTHER INFORMATION: MCS polylinker in PHIL-D2 vector

<400> SEQUENCE: 175
ttcgaaacca tggccgcgga ctagtggcca ccatcaccat caccattaac gcgaattc 58

<210> SEQ ID NO 176
<211> LENGTH: 9
<212> TYPE: PRT
<213> ORGANISM: artificial
<220> FEATURE:
<223> OTHER INFORMATION: C terminal histidine tag

<400> SEQUENCE: 176

Thr Ser Gly His His His His His His
1 5

<210> SEQ ID NO 177
<211> LENGTH: 16
<212> TYPE: PRT
<213> ORGANISM: Human rhinovirus

<400> SEQUENCE: 177

Gly Thr Gln Val Ser Arg Gln Asn Val Gly Thr His Ser Thr Gln Asn
1 5 10 15

<210> SEQ ID NO 178
<211> LENGTH: 16
<212> TYPE: PRT
<213> ORGANISM: Human rhinovirus

<400> SEQUENCE: 178

Gly Ala Gln Val Ser Arg Gln Asn Val Gly Thr His Thr Thr Gln Asn
1 5 10 15